United States Patent
Tammabattula

(10) Patent No.: US 10,966,515 B2
(45) Date of Patent: Apr. 6, 2021

(54) SKINCARE DEVICE

(71) Applicant: Qyk Brands, LLC, Santa Ana, CA (US)

(72) Inventor: Rakesh Tammabattula, Santa Ana, CA (US)

(73) Assignee: Qyk Brands, LLC, Garden Grove, CA (US)

( * ) Notice: Subject to any disclaimer, the term of this patent is extended or adjusted under 35 U.S.C. 154(b) by 0 days.

(21) Appl. No.: 16/687,428

(22) Filed: Nov. 18, 2019

(65) Prior Publication Data

US 2020/0154874 A1 May 21, 2020

Related U.S. Application Data

(63) Continuation-in-part of application No. 29/699,184, filed on Jul. 23, 2019, now Pat. No. Des. 872,939, and
(Continued)

(30) Foreign Application Priority Data

Nov. 19, 2018 (IN) .............................. 201841043445

(51) Int. Cl.
*A46B 13/02* (2006.01)
*A61N 1/32* (2006.01)
(Continued)

(52) U.S. Cl.
CPC .......... *A46B 13/023* (2013.01); *A46B 5/0008* (2013.01); *A46B 15/0006* (2013.01);
(Continued)

(58) Field of Classification Search
CPC ... A46B 13/023; A46B 13/02; A46B 15/0075; A46B 15/0016; A46B 15/0022;
(Continued)

(56) References Cited

U.S. PATENT DOCUMENTS

| | | | | |
|---|---|---|---|---|
| 1,705,249 A | 3/1929 | Henry | | |
| 6,490,760 B1 * | 12/2002 | Lauer | ....................... | A46B 5/00 16/110.1 |

(Continued)

FOREIGN PATENT DOCUMENTS

| | | |
|---|---|---|
| CN | 303109591 S | 2/2015 |
| CN | 303193705 S | 5/2015 |

(Continued)

OTHER PUBLICATIONS

Wikipedia, Steel, https://en.wikipedia.org/wiki/Steel (Year: 2018).*
(Continued)

*Primary Examiner* — Orlando E Aviles
*Assistant Examiner* — Robert F Neibaur
(74) *Attorney, Agent, or Firm* — Eric Kelly

(57) ABSTRACT

The invention is of various portable, handheld, electronic skincare devices with exterior regions that are configured to engage human skin in a manner that provides a benefit to the skin and/or to tissue proximate to the skin. The exterior regions are configured to vibrate, heat, cool, sense, and/or stimulate the skin. The generated and applied vibrations may be of predetermined and different waveforms configured to achieve a particular result, such as, applying a skincare product to the skin or loosening an element from the skin. The exterior regions may be: a plurality of touch-points, a smooth-plate, and/or a rounded and smooth base. The benefit may be of: cleansing, massaging, soothing, relaxing, loosening of sinus pressure, application of skincare product to skin, removal of skincare product from the skin, opening of skin pores, closing of skin pores, heating, cooling, wrinkle reduction, massaged lymphatic tissue, and/or drained lymphatic tissue.

21 Claims, 37 Drawing Sheets

Related U.S. Application Data a continuation-in-part of application No. 29/699,186, filed on Jul. 23, 2019, now Pat. No. Des. 872,372, and a continuation-in-part of application No. 29/699,187, filed on Jul. 23, 2019, now Pat. No. Des. 872,940.

(51) Int. Cl.
    *A46B 15/00* (2006.01)
    *A46B 5/00* (2006.01)

(52) U.S. Cl.
    CPC ...... *A46B 15/0075* (2013.01); *A46B 15/0097* (2013.01); *A61N 1/328* (2013.01); *A46B 2200/102* (2013.01)

(58) Field of Classification Search
    CPC . A46B 15/003; A46B 2200/102; A46B 9/005; A46B 9/028; A61N 1/328; A61H 7/005; A61H 7/002; A61H 7/003; A61H 2201/105; A61H 2201/02; A61H 2201/10; A61H 2201/0285; A61H 23/02; A61H 23/00; A61H 23/006
    USPC .............................. 15/22.1, 188; 62/3.1–3.7
    See application file for complete search history.

(56) References Cited

U.S. PATENT DOCUMENTS

| | | | |
|---|---|---|---|
| 7,500,282 | B1 | 3/2009 | Park |
| 8,517,623 | B2* | 8/2013 | Cavaiani ............ A46B 11/0041 401/264 |
| 9,434,064 | B2* | 9/2016 | Rostami ............... A46B 5/0095 |
| 9,889,065 | B2 | 2/2018 | Sedic |
| 9,907,439 | B2 | 3/2018 | Sedic |
| 10,028,884 | B2 | 7/2018 | Sedic |
| 10,213,064 | B2 | 2/2019 | Sedic |
| 2004/0153014 | A1 | 8/2004 | Sage |
| 2007/0118963 | A1 | 5/2007 | Snyder |
| 2014/0194900 | A1 | 7/2014 | Sedic |
| 2015/0105802 | A1 | 4/2015 | Sedic |
| 2016/0135582 | A1 | 5/2016 | Yen |
| 2018/0028395 | A1 | 2/2018 | Roth |
| 2018/0168913 | A1 | 6/2018 | Sedic |
| 2018/0185236 | A1* | 7/2018 | Levi ........................ A61N 1/325 |
| 2019/0290531 | A1* | 9/2019 | Bosma ..................... A61H 7/00 |

FOREIGN PATENT DOCUMENTS

| | | | |
|---|---|---|---|
| CN | 303499920 | S | 12/2015 |
| CN | 303686058 | S | 5/2016 |
| CN | 304035193 | S | 2/2017 |
| CN | 304049527 | S | 2/2017 |
| CN | 304091539 | S | 3/2017 |
| CN | 304451921 | S | 1/2018 |
| CN | 304490046 | S | 2/2018 |
| CN | 304495658 | S | 2/2018 |
| CN | 304506943 | S | 2/2018 |
| CN | 304520914 | S | 2/2018 |
| CN | 304851542 | S | 10/2018 |
| EM | 006064218-0001 | S | 1/2019 |
| KR | 101711448 | B1 * | 3/2017 |
| KR | 300949593.0000 | S | 3/2018 |
| WO | WO-2019184575 | A1 * | 10/2019 ............. A46B 11/00 |

OTHER PUBLICATIONS

Kim Hyun Dong, Machine Translation of KR101711448, Mar. 13, 2017 (Year: 2017).*

Screenshots of QYK Sonic's ZOE Sonic Skincare Device from YouTube.com, video posted by a Brianna Stanko on Aug. 13, 2018 [online]. Retrieved from the Internet Jul. 17, 2019. URL: https://www.youtube.com/watch?v=fMmJLA6Q8kU (Year: 2018).

Silicon Deep Clean Facial Cleanser [online]. Retrieved from the Internet May 27, 2018. URL: https://sites.google.com/a/d.toctai.net/us310/silicon-deep-clean-facial-cleanser-vibration-cleaning-pulsating-brushes-electric-face-massager-for-skin-care (Year: 2018).

Sonic Cleansing Brush with Medical Grade Silica Gel [online]. Retrieved from the Internet Jul. 17, 2019. URL: https://web.archive.org/web/20150317084955/https://www.ibeautymachine.com/sonic-cleansing-brush-with-medical-grade-silicone.html (Year: 2018).

* cited by examiner

SKINCARE DEVICE

The present patent application is a continuation-in-part (CIP) of U.S. non-provisional patent applications: application Ser. No. 29/699,184 filed on Jul. 23, 2019; application Ser. No. 29/699,186 filed on Jul. 23, 2019; and application Ser. No. 29/699,187 filed on Jul. 23, 2019; wherein this present patent application claims priority to both said U.S. non-provisional patent applications under 35 U.S.C. § 120. The above-identified parent U.S. non-provisional patent applications are incorporated herein by reference in their entirety as if fully set forth below.

PRIORITY NOTICE

The present application claims priority under 35 U.S.C. § 119(a) to foreign filed Indian Patent Application Serial No. 201841043445 filed on Nov. 19, 2018, in the name of inventor Rakesh Tammabattula, and entitled, "SKIN CLEANSER," the disclosure of which is incorporated herein by reference in its entirety.

TECHNICAL FIELD OF THE INVENTION

The present invention relates in general to skincare devices and more specifically to portable handheld skincare devices with various electronics that are configured to one or more of: vibrate, heat, cool, sense, stimulate, combinations thereof, and/or the like a given region of skin.

COPYRIGHT AND TRADEMARK NOTICE

A portion of the disclosure of this patent application may contain material that is subject to copyright protection. The owner has no objection to the facsimile reproduction by anyone of the patent document or the patent disclosure, as it appears in the Patent and Trademark Office patent file or records, but otherwise reserves all copyrights whatsoever.

Certain marks referenced herein may be common law or registered trademarks of third parties affiliated or unaffiliated with the applicant or the assignee. Use of these marks is by way of example and should not be construed as descriptive or to limit the scope of this invention to material associated only with such marks.

BACKGROUND OF THE INVENTION

Human skin, a tissue, is the outer covering of the human body which guards the underlying tissues, such as, but not limited to, muscles, lymphatic tissue, sinus tissue, blood, bones, ligaments, internal organs, and the like. Typically, the human skin has up to seven layers, out of which, the outer layer, is known as the "epidermis", which provides the first and often primary protection from the outer environment to the given human. The middle skin layer, also known as "dermis", provides structure and support, and a third layer known as the "subcutaneous fat Layer" provides insulation and acts as a shock absorber.

Further, the epidermis may be subdivided into three sub-layers, the outermost being the "stratum cornium." The outermost layer, this stratum cornium or the outer layer of the epidermis may be prone to hyperpigmentation and/or exhibit hyperpigmentation, such as, but not limited to, freckles, blotches, spots, sun spots, darkening, wrinkling, and/or other chronic changes, typically associated with skin aging and/or environmental exposure (e.g., repeated exposure to sunlight, dry air, high altitude air, excessively damp/wet air, etc.). Depending upon the given individual, some hyperpigmentation and/or skin conditions may be undesired, such as skin wrinkles.

A number of techniques exist for conditioning of skin, particularly, for facial skin, to minimize or eliminate hyperpigmentation and/or other undesired skin conditions, such as, but not limited to, wrinkling and/or other chronic skin changes. Some of these techniques involve application of one or more skincare products to the skin, such as, but not limited to, cosmetics/makeup, packs/masks, vitamins/minerals/supplements, lotions, ointments, gels, chemical peeling, medicines, pharmaceuticals, and laser treatments. Other techniques utilize diet and/or massage. Many such techniques require an expert/specialist for execution, such as, but not limited to, a prescription from a licensed physician for a particular treatment. Further, many of these techniques are time-intensive and/or expensive as well.

Accordingly, many people rely on manual cleaning and massaging of the facial skin, for example, by using, hands, a brush, face wash liquids, foams, and/or lotions. However, such measures often help in removing dust/dirt particles only, and are not effective in cleaning impurities/contaminants (e.g., undesired bacteria), for example, present inside pores of the skin. Therefore, these skin washing/massaging techniques using hands/brushes and typical skin cleaners are fragmented in their approach and often largely ineffective as well. Moreover, manually performing these operations is a cumbersome task and demands significant efforts from a given person. Accordingly, such manual cleaning of the skin on a daily basis may not achieve desired or needed results.

There is a need in the art for various portable, handheld, electronic skincare devices with one or more exterior regions that are configured to engage a region of human skin in a manner that may provide a benefit to that region of human skin and/or to tissue proximate to that region of human skin.

There is a need in the art for such skincare devices that may provide at least one benefit to a region of skin and/or to tissue proximate to that region of skin, wherein that benefit to the region of human (and/or to the tissue proximate to that region of human skin) may be one or more of: cleansing, massaging, soothing, relaxing, loosening of sinus pressure, application of skincare product to skin, removal of skincare product from the skin, opening of skin pores, closing of skin pores, heating, cooling, wrinkle reduction, massaged lymphatic tissue, drained lymphatic tissue, combinations thereof, and/or the like.

It is to these ends that the present invention has been developed.

BRIEF SUMMARY OF THE INVENTION

To minimize the limitations in the prior art, and to minimize other limitations that will be apparent upon reading and understanding the present specification, the present invention describes various portable, handheld, electronic skincare devices with one or more exterior regions that are configured to engage a region of human skin in a manner that may provide a benefit to that region of human skin and/or to tissue proximate to that region of human skin. The one or more exterior regions may be configured to one or more of: vibrate (e.g., via one or more motors), heat (e.g., via a Peltier device/circuit), cool (e.g., via a Peltier device/circuit), sense (i.e., measuring a characteristic of human skin using one or more sensors), stimulate (e.g., as in e-stem via electrodes applied to the region of human skin), combinations thereof, and/or the like—all with respect to that region of human skin. In some embodiments, the generated and applied vibrations may be of predetermined and different waveforms configured to achieve a particular result, such as, applying a skincare product to the skin or loosening an element from the skin. The one or more exterior regions of the given skincare device may be selected from one or more of: at least one plurality of touch-points, at least one smooth-plate, at least one rounded and smooth base, combinations thereof, and/or the like. The benefit to the region of human (and/or to the tissue proximate to that region of human skin) may be one or more of: cleansing, massaging, soothing, relaxing, loosening of sinus pressure, application of skincare product to skin, removal of skincare product from the skin, opening of skin pores, closing of skin pores, heating, cooling, wrinkle reduction, massaged lymphatic tissue, drained lymphatic tissue, combinations thereof, and/or the like.

In some embodiments, the given skincare device may be comprised of a main-body and a base. In some embodiments, the main-body may be a closed three-dimensional shape, enclosing a volume. In some embodiments, the main-body may comprise two opposing major-sides, a first-major-side and a second-major-side, respectively. In some embodiments, the first-major-side may be joined to the second-major-side along a shared boundary that runs along an outer peripheral edge of the main-body such that the volume is substantially enclosed by the first-major-side joined to the second-major-side. In some embodiments, disposed at least partially between the first-major-side and the second-major-side and at least partially inside the volume of the main-body are a plurality of electronic components. In some embodiments, the plurality of electronic components may be selected from one or more of: at least one processor/controller/microcontroller/CPU, at least one memory, at least one power-source, at least one motor, at least one heater/cooler, at least one sensor (e.g., for sensing at least one characteristic of the skin), at least one communication module (e.g., for wireless and/or wired communications), at least one input/output (I/O) means, other circuitry, combinations thereof, and/or the like.

In some embodiments, the first-major-side may comprise a first-pad on an upper portion of the first-major-side. In some embodiments, the second-major-side may comprise a second-pad on an upper portion of the second-major-side. In some embodiments, the first-pad and/or the second-pad may each have their own respective outer exterior portion (e.g., the one or more exterior regions of the given skincare device) that is configured for physically pressing against the region of human skin.

In some embodiments, the plurality of electronic components of the given skincare device may minimally comprise the at least one motor and the at least one power-source. In some embodiments, the at least one power-source may be operatively linked to the at least one motor so as to provide electrical power to the at least one motor. In some embodiments, the at least one motor may be operatively linked to at least the first-pad, such that when the at least one motor is activated vibrations are transmitted to the first-pad, which may then be transmitted to region of human skin for a desired benefit to that region of human skin.

It is an objective of the present invention to provide a portable, handheld, electronic skincare device with one or more exterior regions that are configured to engage a region of human skin in a manner that may provide a benefit to that region of human skin and/or to tissue proximate to that region of human skin.

It is another objective of the present invention to provide a portable, handheld, electronic skincare device with one or more of: at least one plurality of touch-points (e.g., located on a given pad of the given skincare device), at least one smooth-plate, at least one rounded and smooth base, combinations thereof, and/or the like It is another objective of the present invention to provide a portable, handheld, electronic skincare device with a plurality of electronic components.

It is another objective of the present invention to provide a portable, handheld, electronic skincare device with one or more of: at least one processor/controller/microcontroller/CPU, at least one memory, at least one power-source, at least one motor, at least one heater/cooler, at least one sensor (e.g., for sensing at least one characteristic of the skin), at least one communication module (e.g., for wireless and/or wired communications), at least one input/output (I/O) means, other circuitry, combinations thereof, and/or the like.

It is another objective of the present invention to provide a portable, handheld, electronic skincare device that through is at least motor may generate a variety of predetermined and different waveforms, wherein each such waveform may be configured for a particular use, such as, but not limited to, applying a skincare product to the skin or removing/loosening an element (e.g., dirt, contaminant, old makeup, bacteria, etc.) from the skin.

It is another objective of the present invention to provide a portable, handheld, electronic skincare device that may receive user inputs at controls found an exterior of the given skincare device.

It is another objective of the present invention to provide a portable, handheld, electronic skincare device that receive user inputs from a separate and different computing-device that may be in communication (e.g., via wireless and/or wired communications) with the given skincare device.

It is another objective of the present invention to provide a portable, handheld, electronic skincare device with electronic components (such as, but not limited to, gyroscopes, accelerometers, GPS modules, combinations thereof, and/or the like) for mapping a topographical contour of a region of human skin.

It is another objective of the present invention to provide a portable, handheld, electronic skincare device with at least one visual indicator, such as, but not limited to, a LED light ring, that may indicate status, change of status, combinations thereof, and/or the like of the given skincare device.

It is another objective of the present invention to provide a portable, handheld, electronic skincare device with a smooth-plate that is configured for heating and/or cooling the region of human skin (e.g., the smooth-plate may be operatively linked to one or more Peltier heating/cooling solid state circuits).

It is another objective of the present invention to provide a portable, handheld, electronic skincare device with one or more sensors for measuring at least one characteristic of human skin.

It is another objective of the present invention to provide a portable, handheld, electronic skincare device with one or more electrodes for generating and/or applying an electrical pulse/micro-current to the region of human skin to stimulate that region of skin and/or to stimulate tissue that may be proximate to that region of human skin (such as muscle tissue beneath that region of skin).

It is another objective of the present invention to provide a portable, handheld, electronic skincare device that may provide at least one benefit to that region of skin and/or to tissue proximate to that region of skin (tissue proximate may be muscle tissue, lymphatic tissue, and/or sinus tissue beneath the region of human skin), wherein that benefit to the region of human (and/or to the tissue proximate to that region of human skin) may be one or more of: cleansing, massaging, soothing, relaxing, loosening of sinus pressure, application of skincare product to skin, removal of skincare product from the skin, opening of skin pores, closing of skin pores, heating, cooling, wrinkle reduction, massaged lymphatic tissue, drained lymphatic tissue, combinations thereof, and/or the like.

It is another objective of the present invention to provide a portable, handheld, electronic skincare device with a removable/detachable base.

It is another objective of the present invention to provide a portable, handheld, electronic skincare device with a base that has at least one electronic component housed at least substantially within that base.

It is yet another objective of the present invention portable, handheld, electronic skincare device with a base that may be configured to vibrate, heat, cool, sense, stimulate (e.g., via electrical pulse), combinations thereof, and/or the like—with respect to the region of human skin.

These and other advantages and features of the present invention are described herein with specificity so as to make the present invention understandable to one of ordinary skill in the art, both with respect to how to practice the present invention and how to make the present invention.

BRIEF DESCRIPTION OF THE SEVERAL VIEWS OF THE DRAWINGS

Elements in the figures have not necessarily been drawn to scale in order to enhance their clarity and improve understanding of these various elements and embodiments of the invention. Furthermore, elements that are known to be common and well understood to those in the industry are not depicted in order to provide a clear view of the various embodiments of the invention.

Figure 1:
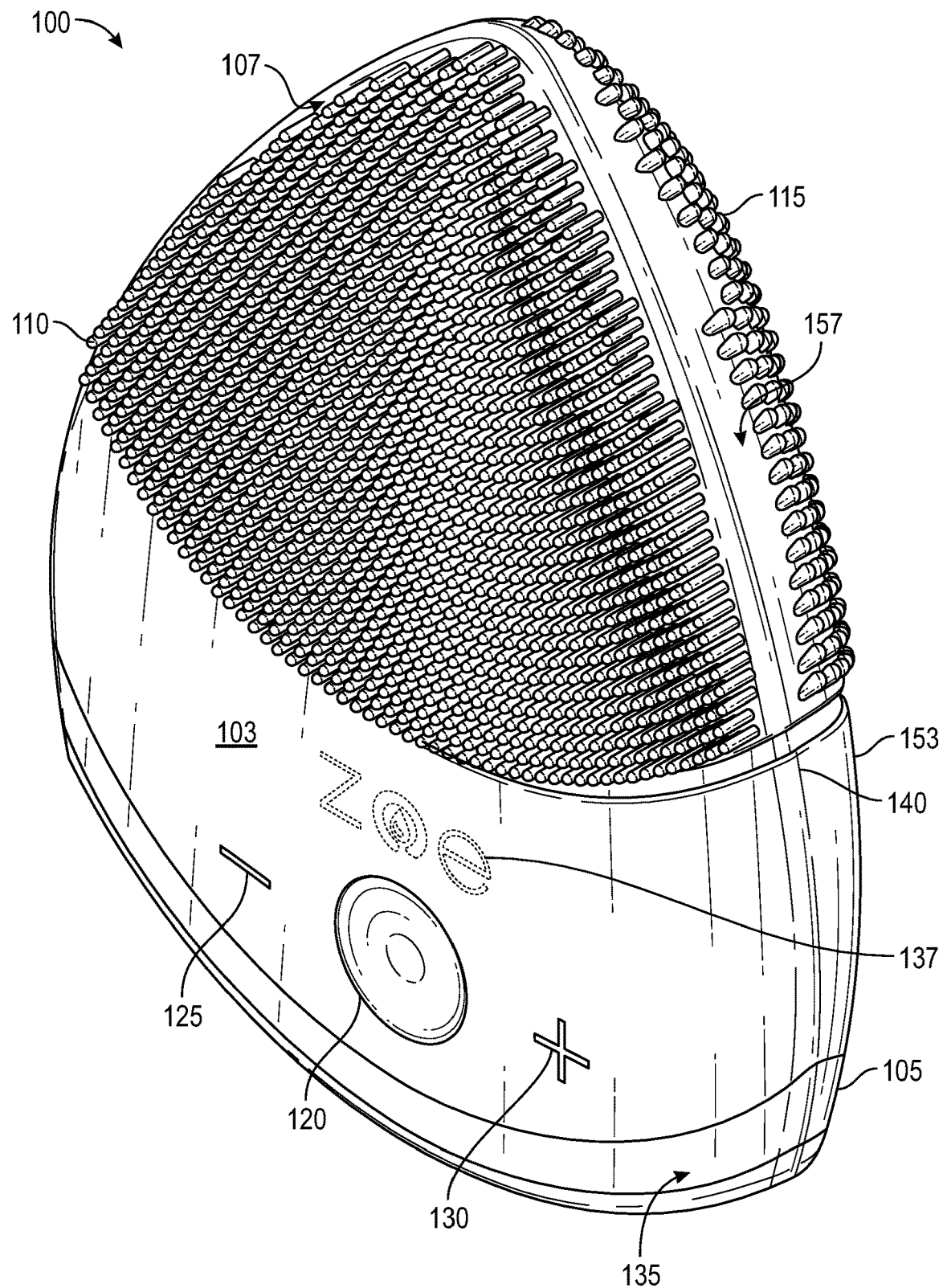
FIG. 1 depicts a perspective view of a portable, handheld, electronic skincare device, according to a first embodiment.

REFERENCE NUMERAL SCHEDULE 100 skincare device 100
103 first-major-side 103
105 base 105
107 first-pad 107
110 touch-point 110
115 touch-point 115
120 control 120
125 control 125
130 control 130
135 indicator 135
137 graphic 137
140 boundary 140
153 second-major-side 153
157 second-pad 157
203 main-body 203
211 top 211
219 bottom 219

229 bottom 229
301 connector 301
705 exterior-surface-of-base 705
800 skincare device 800
803 first-major-side 803
805 base 805
807 first-pad 807
840 boundary 840
853 second-major-side 853
857 second-pad 857
903 main-body 903
911 top 911
919 bottom 919
929 bottom 929
1001 first-electrode 1001
1003 second-electrode 1003
1405 exterior-surface-of-base 1405
1500 skincare device 1500
1501 smooth-plate 1501
2200 skincare device 2200
2801 fastener 2801
2805 surface-of-bottom 2805
2900 skincare device 2900
3600 skincare device 3600
3603 first-major-side 3603
3607 first-pad 3607
3640 boundary 3640
3653 second-major-side 3653
3657 second-pad 3657
3707 bottom 3707
3703 main-body 3703
3807 bottom 3807
4301 connector 4301
4305 top-surface 4305
4501 upper-base-portion 4501
4503 lower-base-portion 4503
4701 microcontroller 4701
4703 memory 4703
4705 power-source 4705
4707 motor 4707
4709 heater/cooler 4709
4711 sensor 4711
4713 communications module 4713
4715 I/O means 4715
4717 other circuitry 4717
4801 skincare device 4801
4802 communication-pathway 4802
4803 computing-device 4803
4804 communication-pathway 4804
4805 Internet/WAN/LAN/Network 4805
4806 communication-pathway 4806
4900 method of using skincare device on skin 4900
4901 step of receiving user input to turn on skincare device 4901
4903 step of receiving user input of selected operational mode for skincare device 4903
4905 step of pressing skincare device against skin 4905
4907 step of applying skincare product to skin 4907
4909 step of achieving result 4909

DETAILED DESCRIPTION OF THE INVENTION

In the following discussion that addresses a number of embodiments and applications of the present invention, reference is made to the accompanying drawings that form a part thereof, where depictions are made, by way of illustration, of specific embodiments in which the invention may be practiced. It is to be understood that other embodiments may be utilized and changes may be made without departing from the scope of the invention.

The terms "comprises," "comprising," or any other variations thereof, are intended to cover a non-exclusive inclusion, such that a process or method that comprises a list of steps does not necessarily include only those steps but may include other steps not expressly listed or inherent to such a process or a method. Similarly, one or more devices or sub-systems or elements or structures or components preceded by "comprises . . . a" does not, without more constraints, preclude the existence of other devices, other sub-systems, other elements, other structures, other components, additional devices, additional sub-systems, additional elements, additional structures, or additional components. Appearances of the phrase "in an embodiment," "in another embodiment," and similar language throughout this specification may, but do not necessarily, all refer to the same embodiment.

Unless otherwise defined, all terms associated with reference numerals, as well as technical and scientific terms used herein have the same meaning as commonly understood by one of ordinary skill in the art to which this disclosure belongs. The system, methods, and examples provided herein are illustrative only and not intended to be limiting.

The present disclosure discloses various handheld (mobile) electronic skincare devices which may be used for cleaning, massaging, vibrating, applying skin products (topically) to the skin, removing products from the skin, combinations thereof, and/or the like. And hence to accomplish daily hygienic skin care, in particular for the care and cleanliness of facial skin in an efficient, thorough, comprehensive, and/or reproducible manner. These skincare devices may also be referred to as skin cleansers. Note, the skin products may be selected from one or more of: ointments, lotions, creams, serums, gels, medicines, pharmaceuticals, medicaments, soaps, surfactants, vitamins, supplements, herbs, plants, vegetables, meats, cleansers, cleaners, de-oilers, de-greasers, masks, makeup, cosmetics, face/skin/body paint, treatments, combinations thereof, and/or like.

This patent application discloses and describes six main embodiments of skincare devices, identified herein as skincare device 100, skincare device 800, skincare device 1500, skincare device 2200, skincare device 2900, and skincare device 3600.

Figure 7:
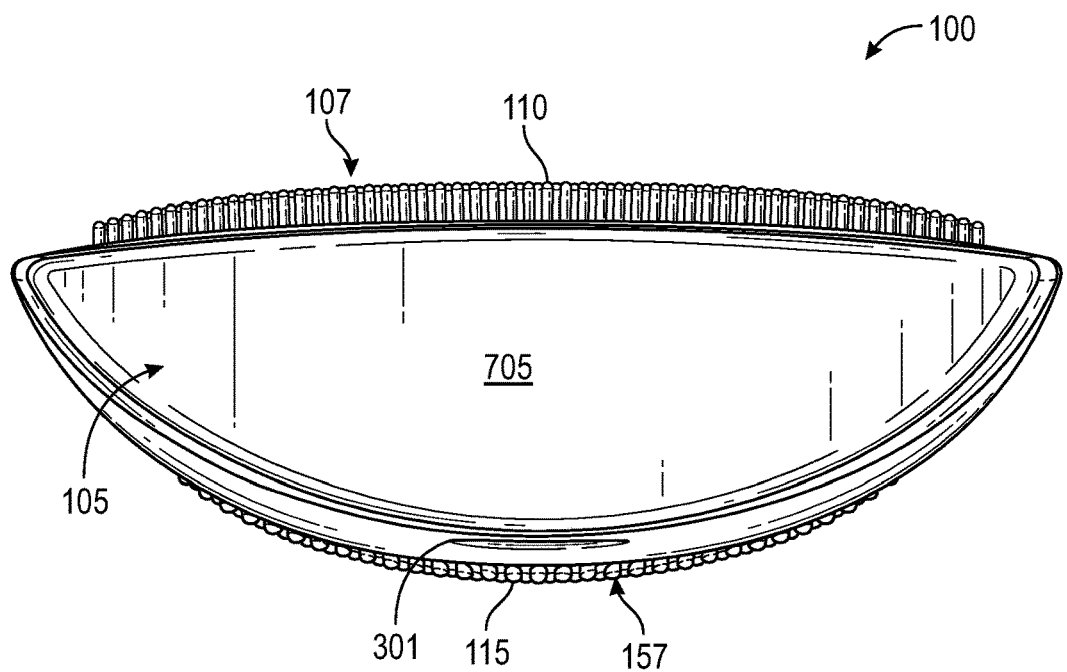
FIG. 7 depicts a bottom view thereof.
Figure 8:
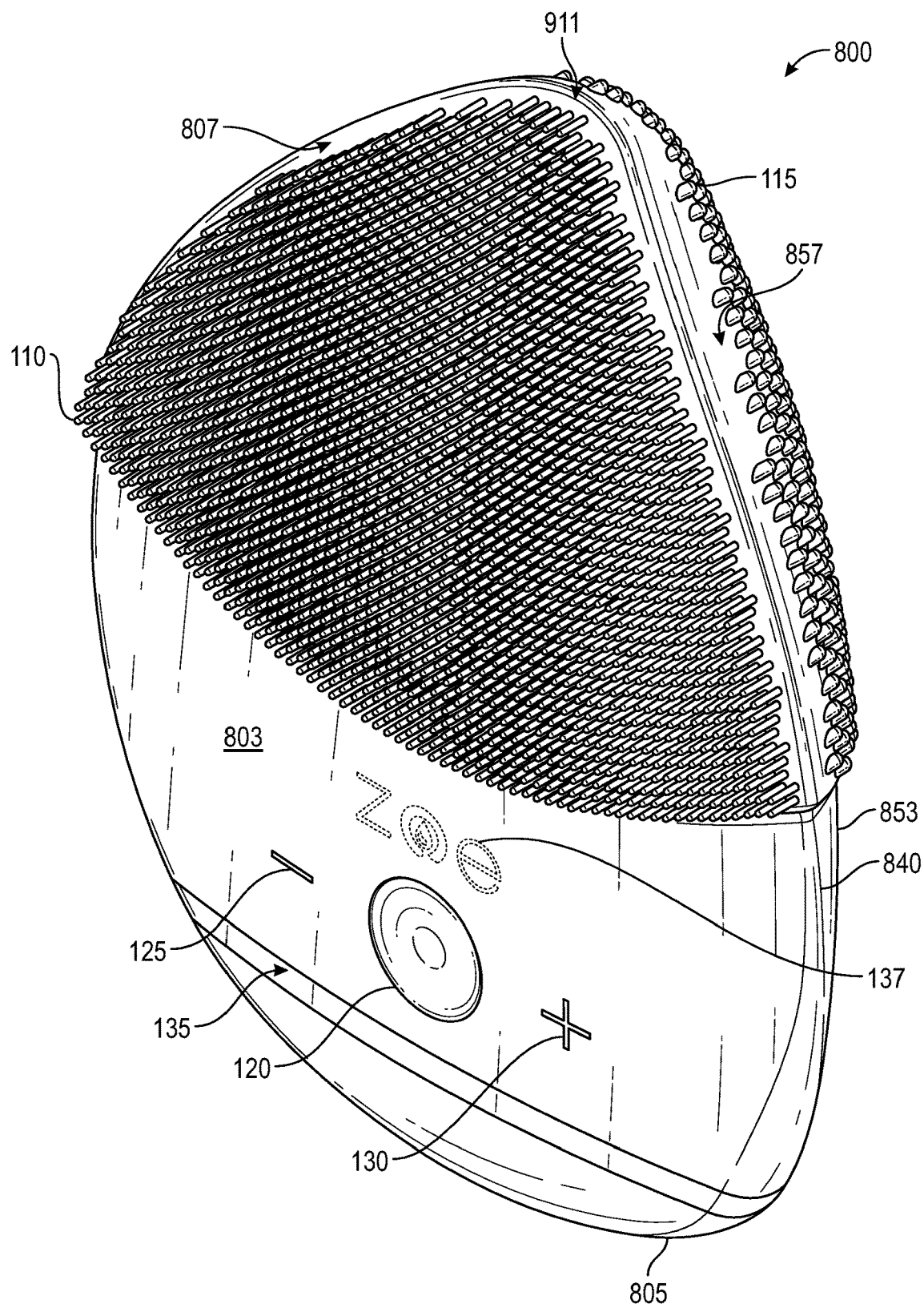
FIG. 8 depicts a perspective view of a portable, handheld, electronic skincare device, according to a second embodiment.
Figure 14:
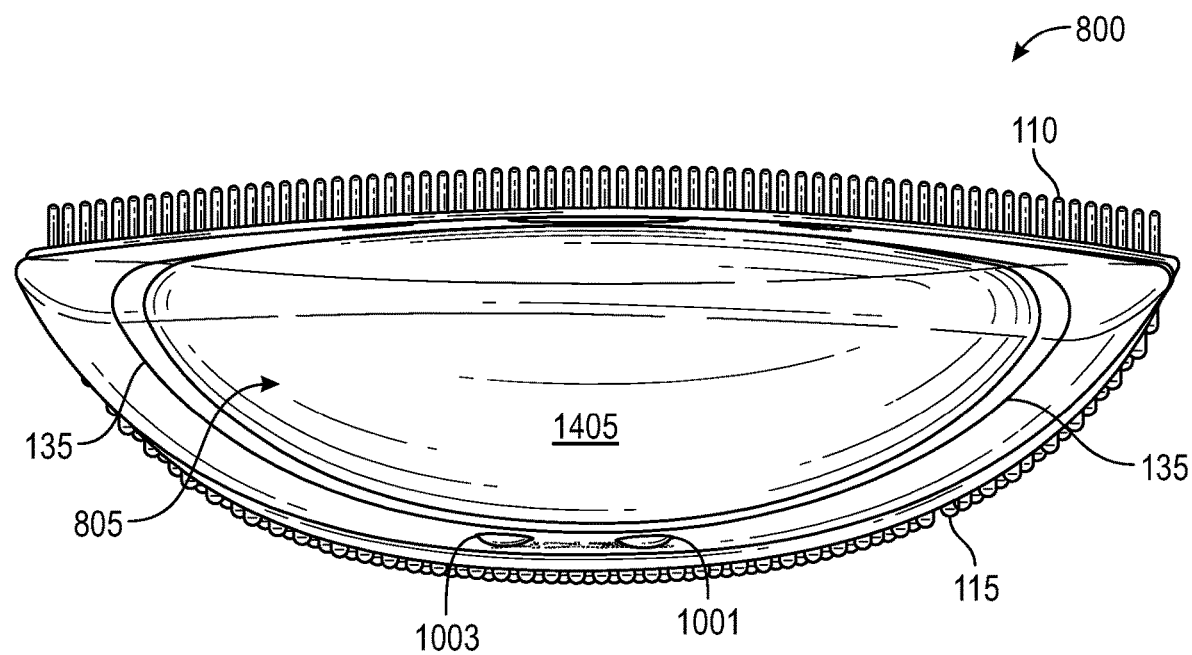
FIG. 14 depicts a bottom view of the second embodiment.
Figure 15:
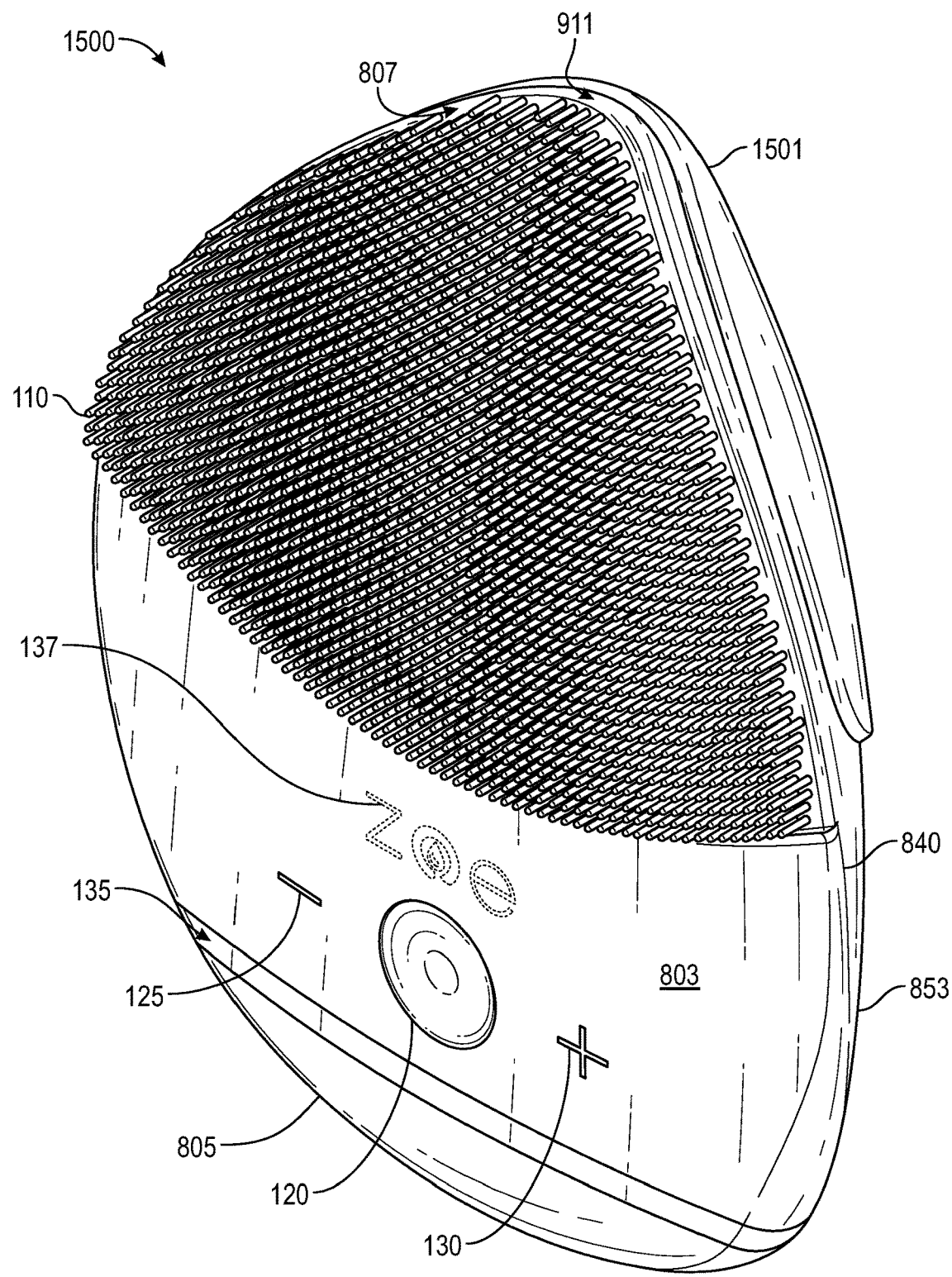
FIG. 15 depicts a perspective view of a portable, handheld, electronic skincare device, according to a third embodiment.
Figure 21:
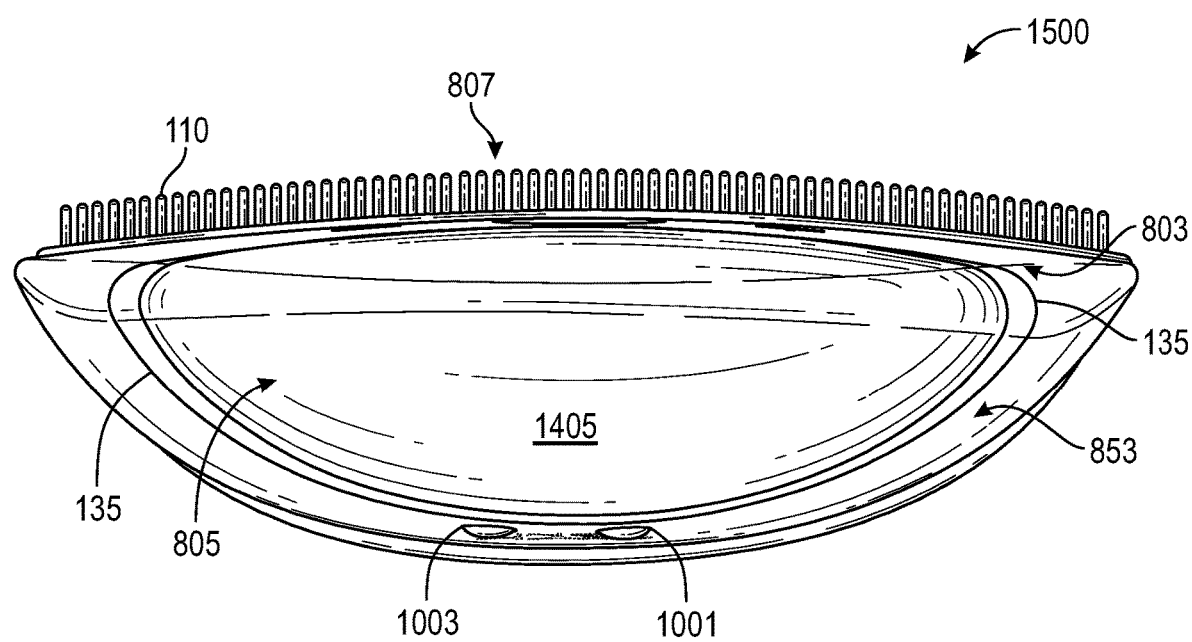
FIG. 21 depicts a bottom view of the third embodiment.
Figure 22:
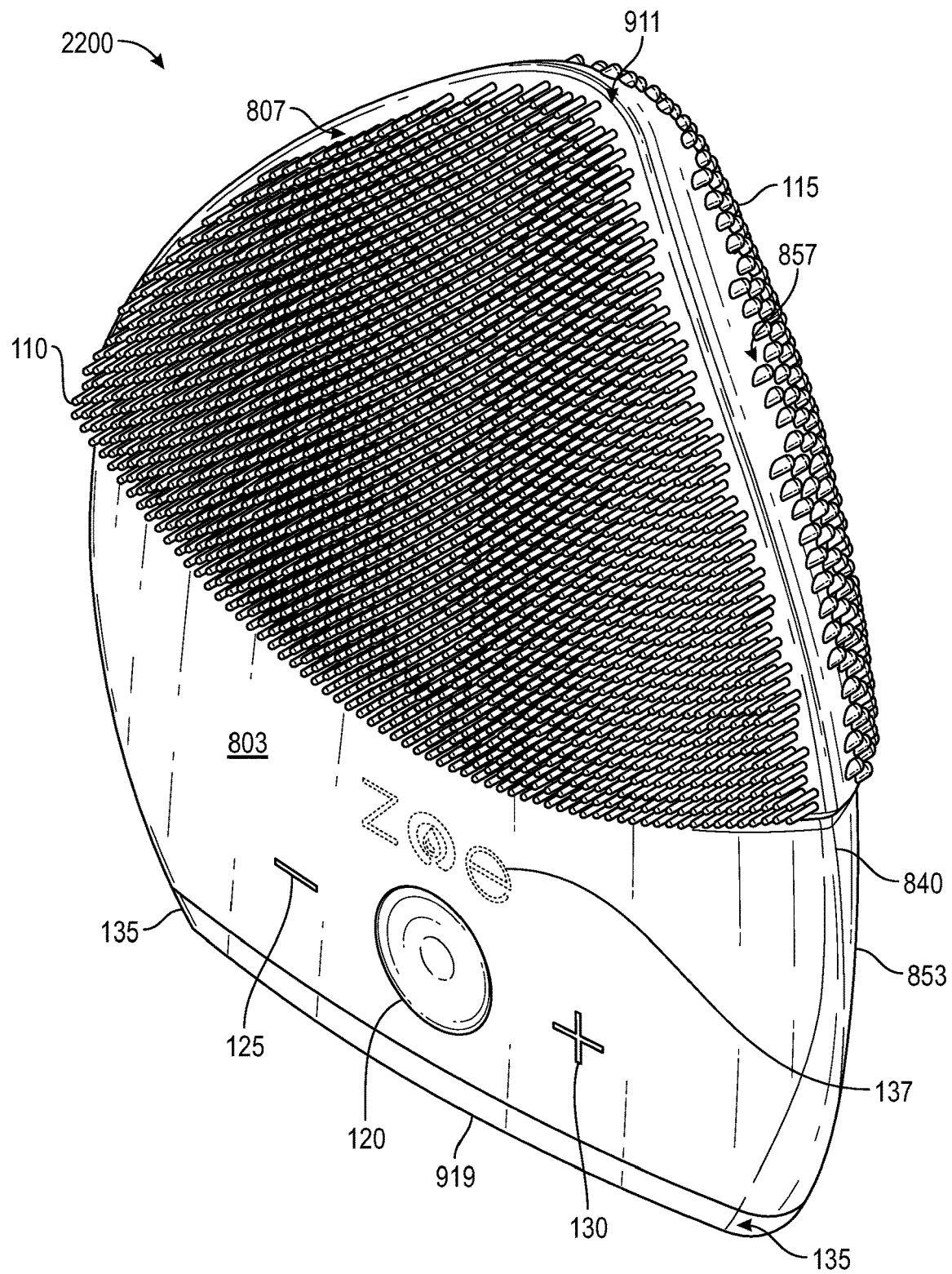
FIG. 22 depicts a perspective view of a portable, handheld, electronic skincare device, according to a fourth embodiment.
Figure 28:
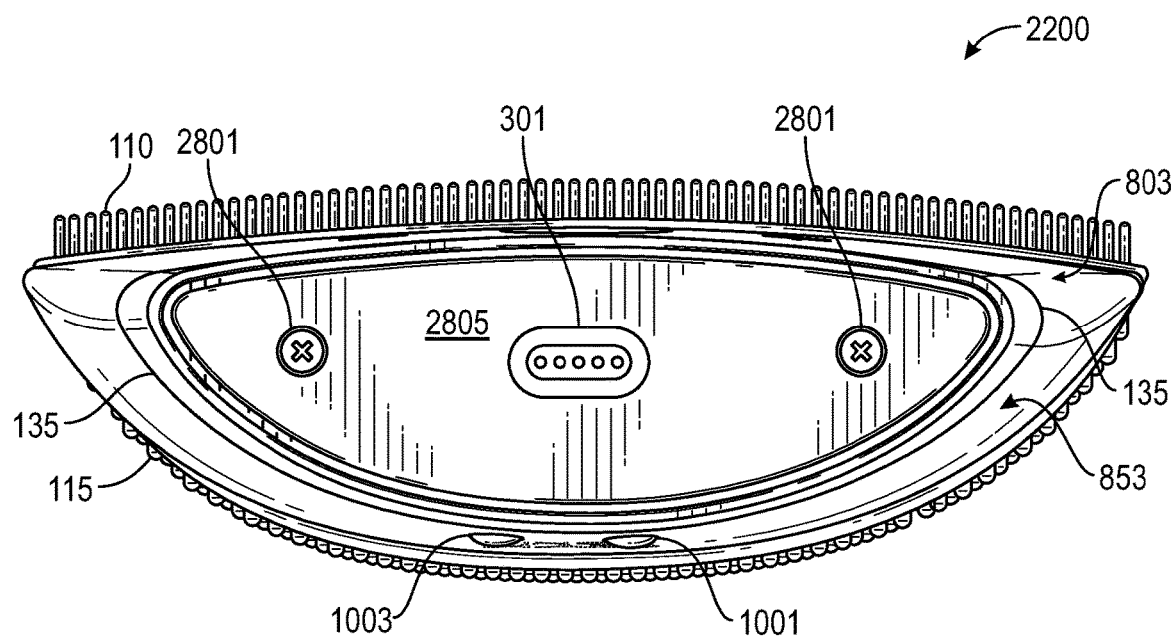
FIG. 28 depicts a bottom view of the fourth embodiment.
Figure 29:
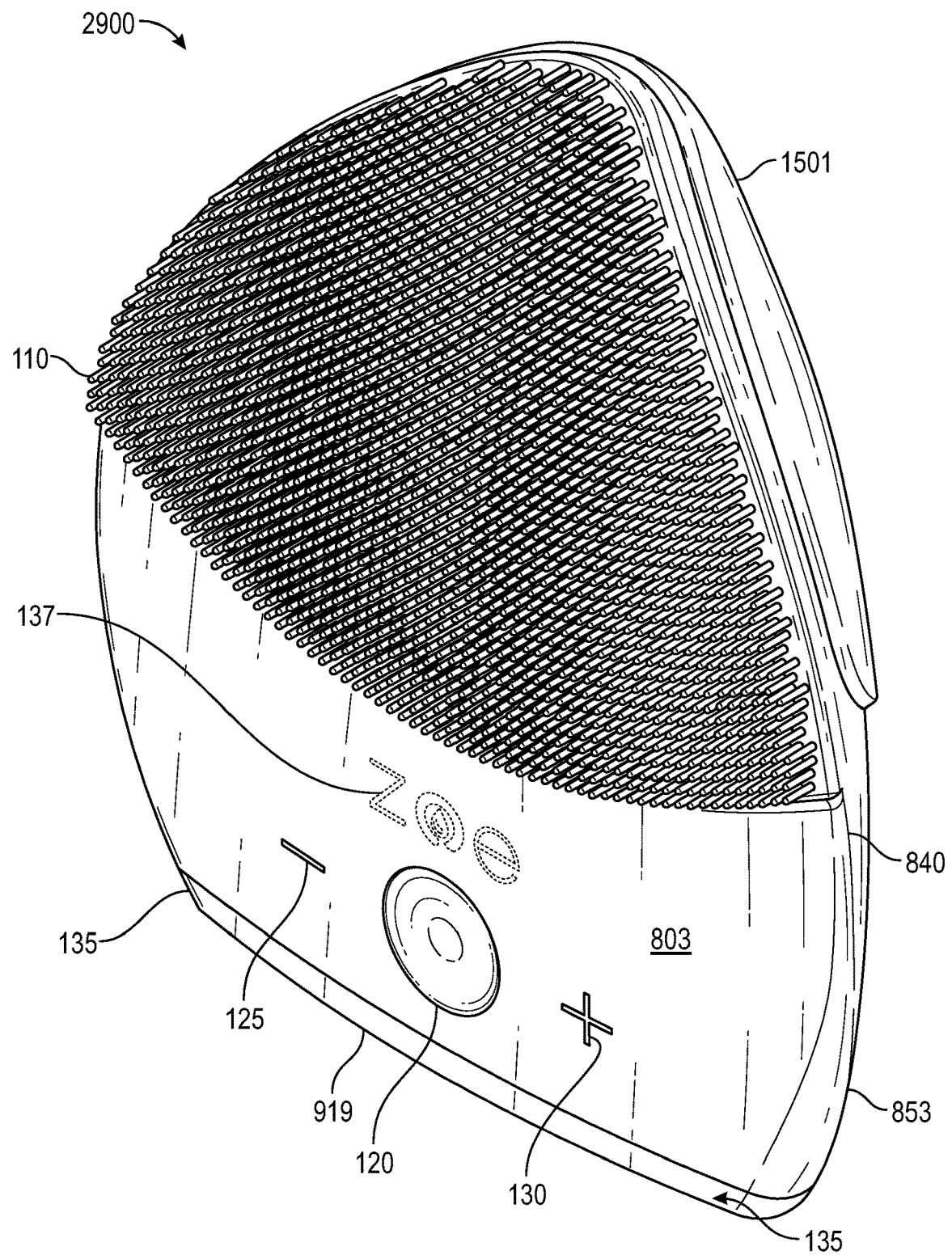
FIG. 29 depicts a perspective view of a portable, handheld, electronic skincare device, according to a fifth embodiment.
Figure 35:
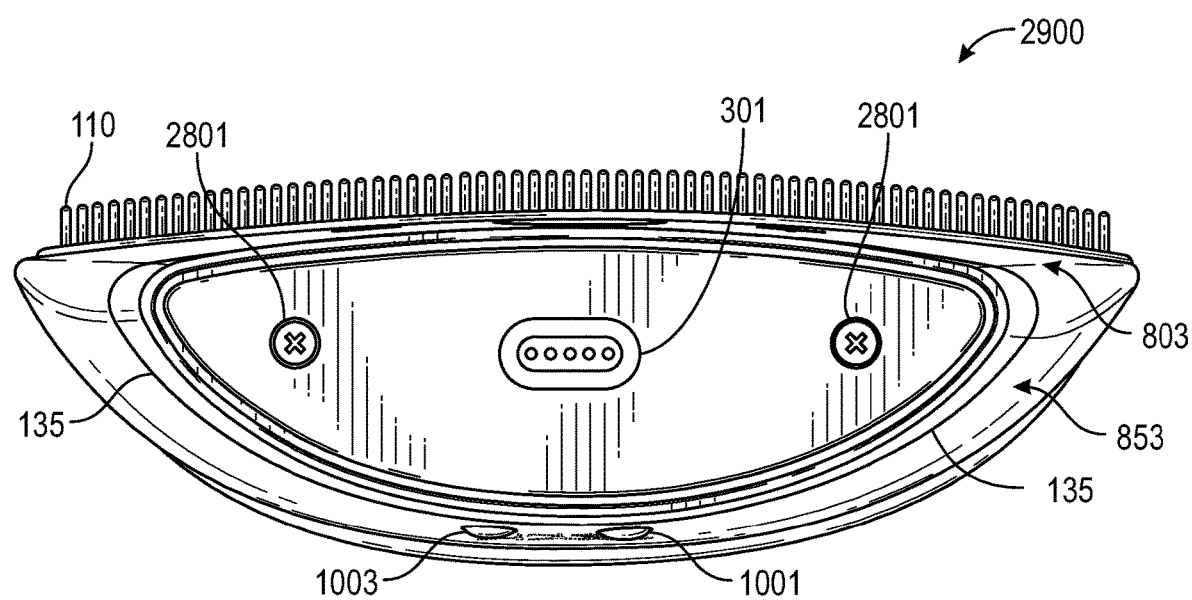
FIG. 35 depicts a bottom view of the fifth embodiment.
Figure 36:
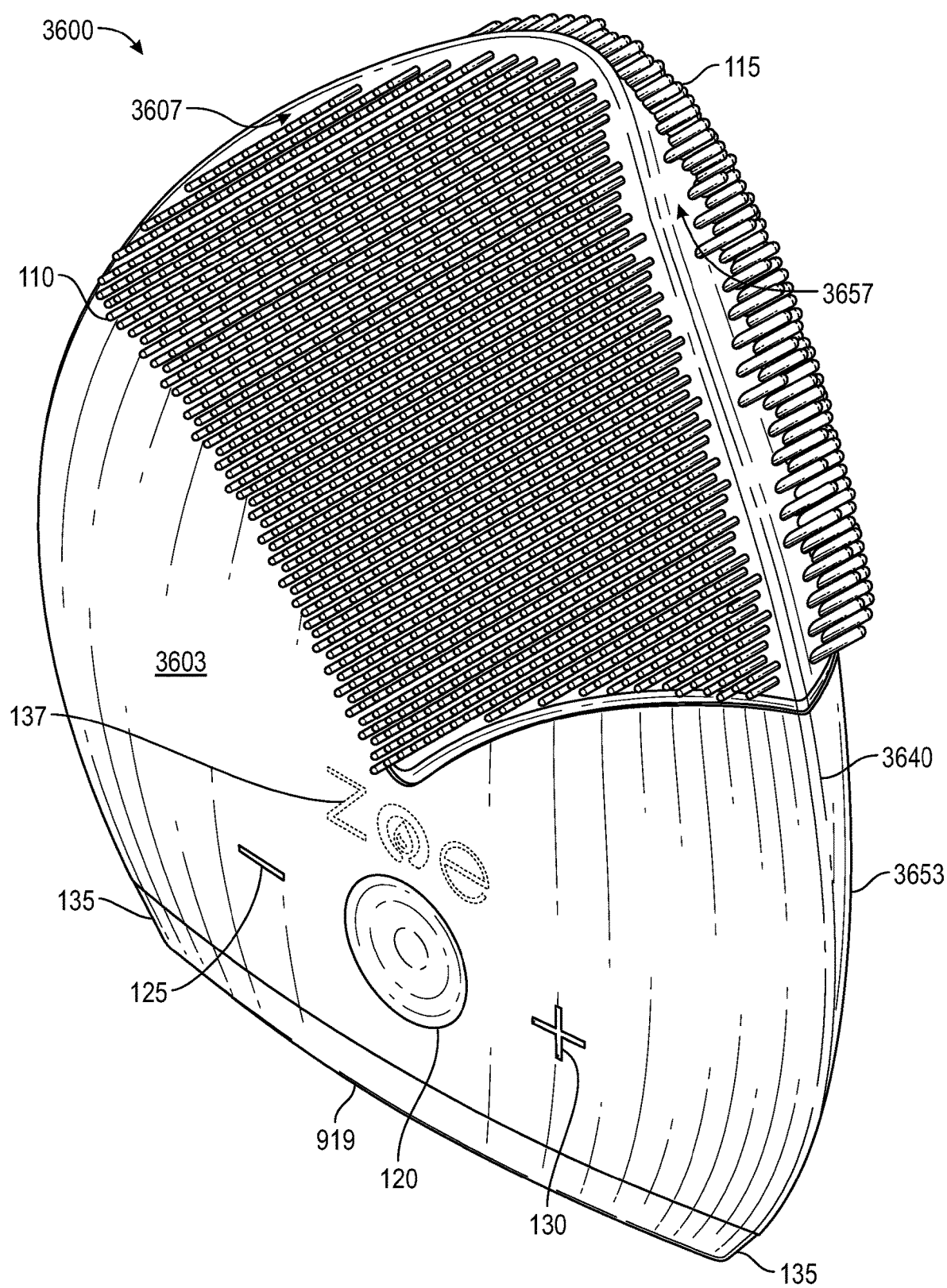
FIG. 36 depicts a perspective view of a portable, handheld, electronic skincare device, according to a sixth embodiment.
Figure 42:
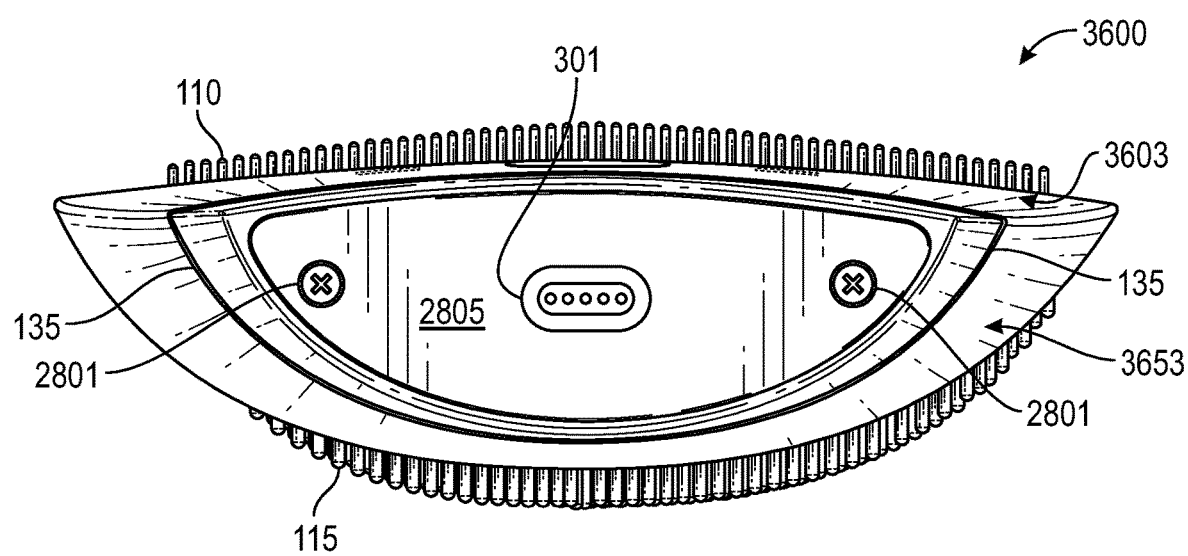
FIG. 42 depicts a bottom view of the sixth embodiment.

Note: skincare device 100 is shown in figures FIG. 1 through and including FIG. 7; skincare device 800 is shown in figures FIG. 8 through and including FIG. 14; skincare device 1500 is shown in figures FIG. 15 through and including FIG. 21; skincare device 2200 is shown in figures FIG. 22 through and including FIG. 28; skincare device 2900 is shown in figures FIG. 29 through and including FIG. 35; and skincare device 3600 is shown in figures FIG. 36 through and including FIG. 42.

Figure 2:
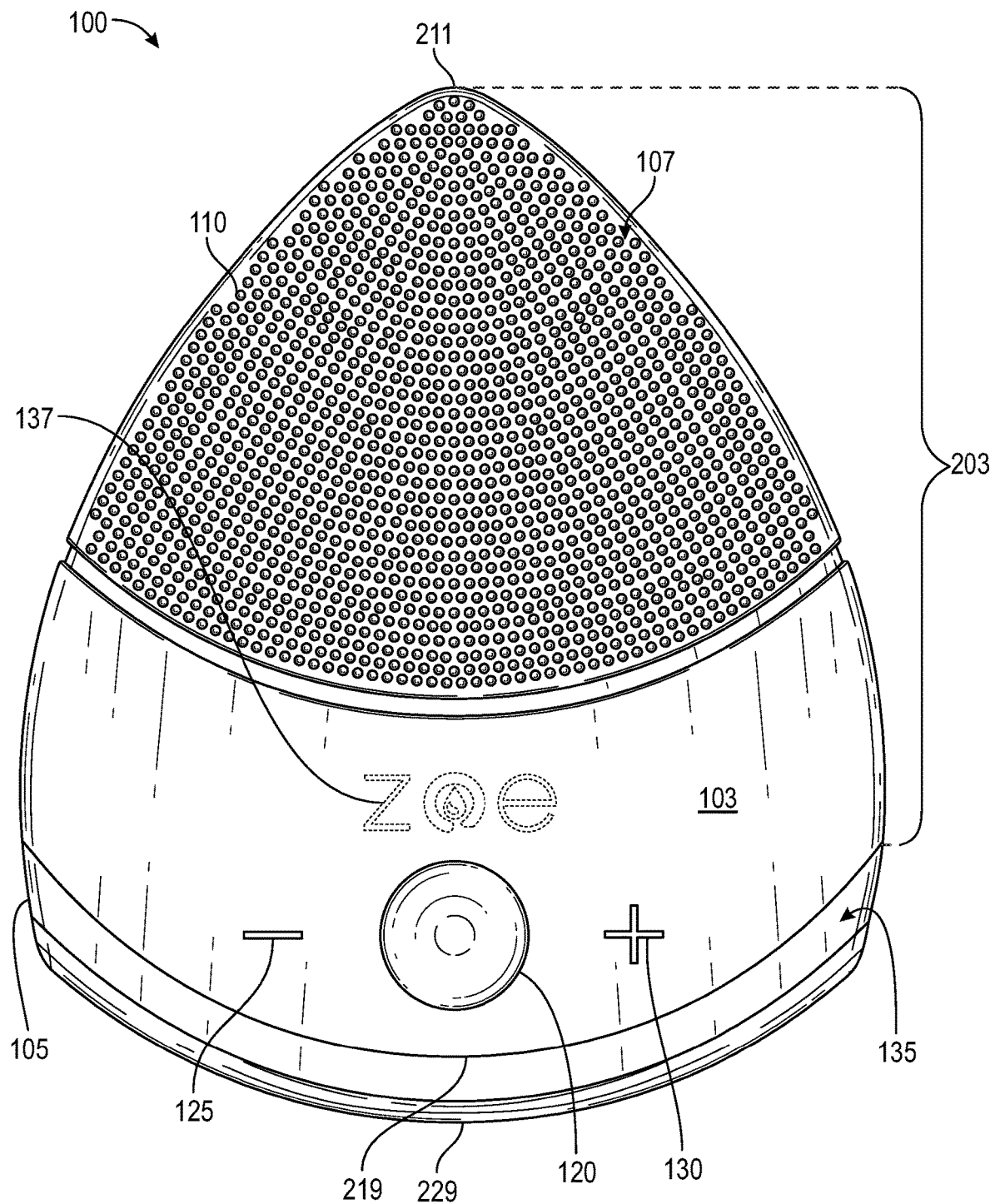
FIG. 2 depicts a front view thereof.

As noted, skincare device 100 is shown in figures FIG. 1 through and including FIG. 7. In some embodiments, skincare device 100 may be comprised of a main-body 203 and a base 105. See e.g., FIG. 2. In some embodiments, base 105 may be attached to a bottom 219 of main-base 203.

Figure 3:
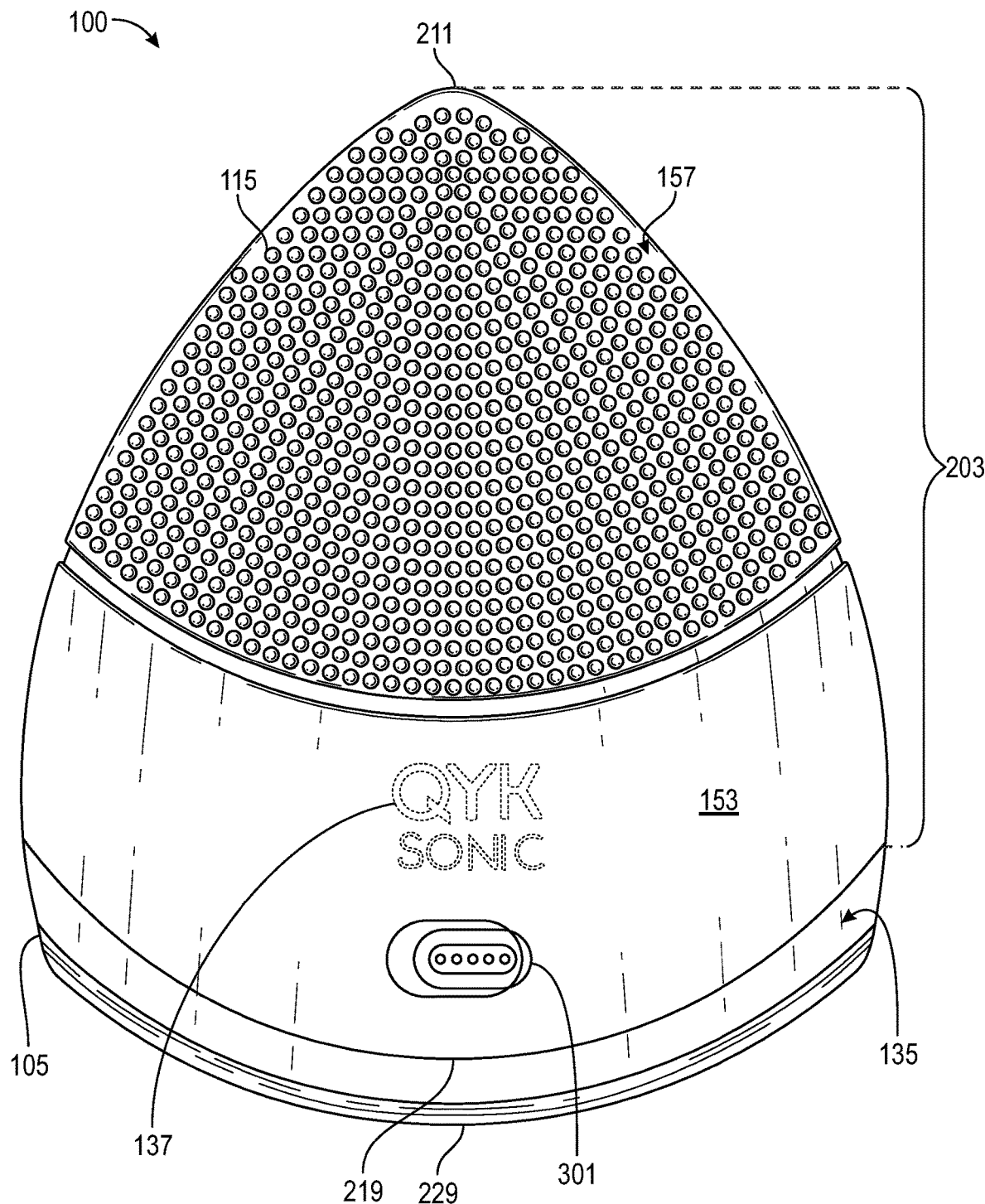
FIG. 3 depicts a back view thereof.
Figure 4:
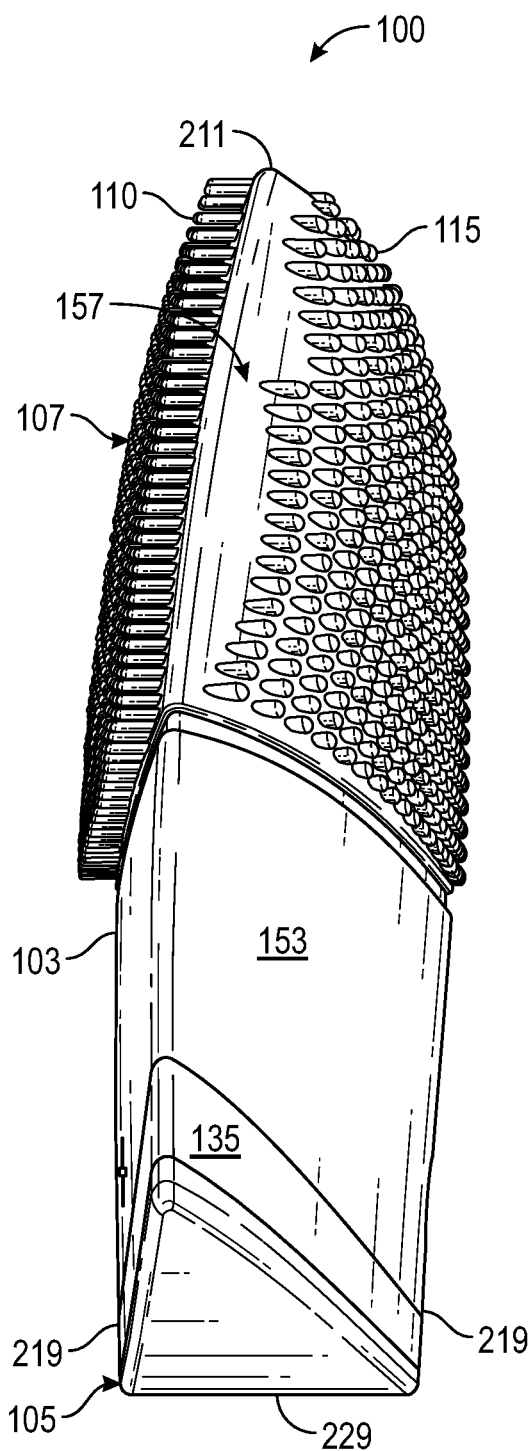
FIG. 4 depicts a right-side view thereof.
Figure 5:
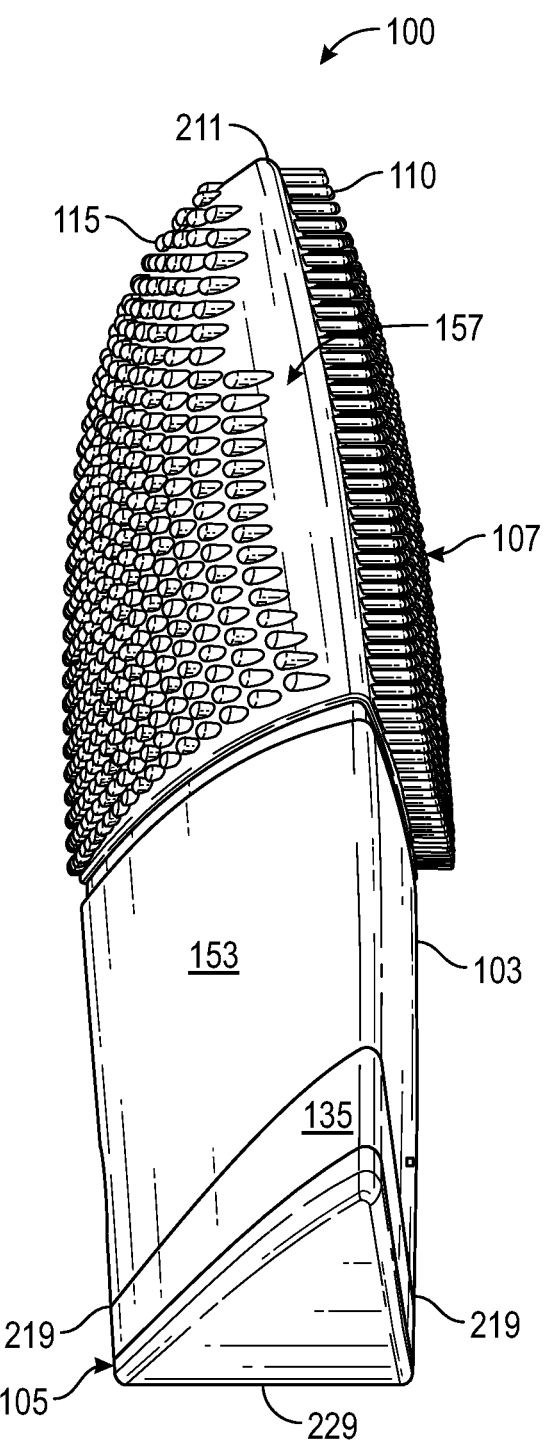
FIG. 5 depicts a left-side view thereof.
Figure 6:
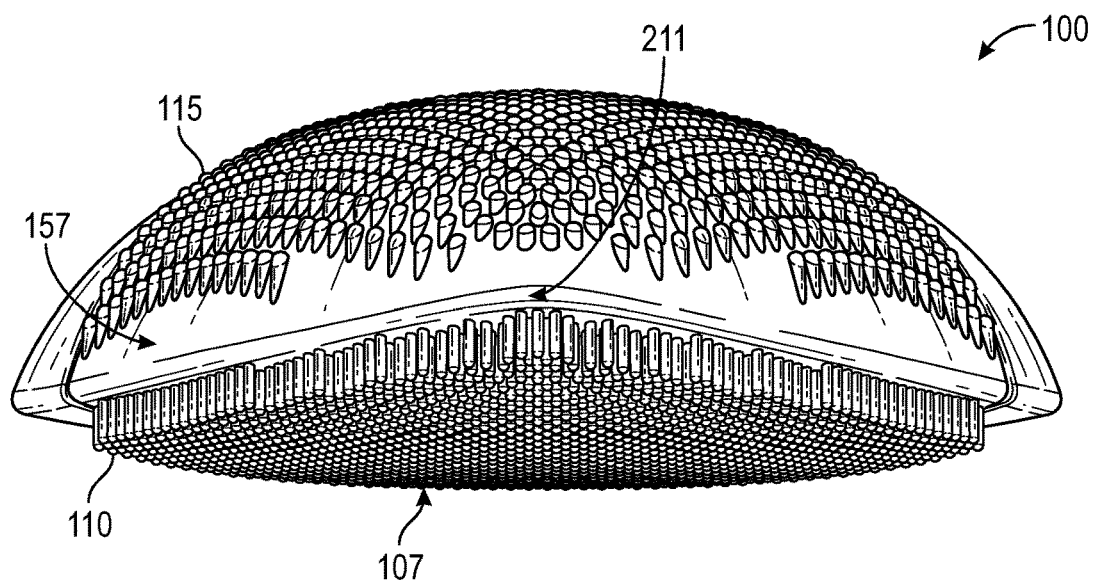
FIG. 6 depicts a top view thereof.

In some embodiments, main-body 203 may be configured to be a portable (mobile) hand-held device. In some embodiments, main-body 203 may be configured to be held and used by one human hand. In some embodiments, main-body 203 may be a three-dimensional (3D) device. From a front view (e.g., FIG. 2) and/or a back/rear view (e.g., FIG. 3), main-body 203 may be substantially or generally shaped: as a wedge, a pie shape, and/or triangular in shape—with a rounded tip at top 211 of main-body 203. From a front view (e.g., FIG. 2) and/or a back/rear view (e.g., FIG. 3), main-body 203 may be substantially or generally shaped: as a wedge, a pie shape, and/or triangular in shape—with a curved bottom at bottom 219 of main-body 203. In some embodiments, main-body 203 may run from top 211 to bottom 219, see e.g., FIG. 2 and/or FIG. 3. In some embodiments, main-body 203 may have a fixed and predetermined thickness (see e.g., FIG. 4 and/or FIG. 5) of about 0.5 inch to about 1.5 inches, plus or minus 0.1 inch.

In some embodiments, main-body 203 may substantially house one or more electronics components, such as, but not limited to, PCBs (printed circuit board(s)), processors, memory, sensors, electrodes, heaters, coolers, batteries, power sources, connectors 301, motors, network communications hardware, radios, antennas, circuits, switches, controls, circuit elements, combinations thereof, and/or the like.

Continuing discussing main-body 203, in some embodiments, main-body 203 may be comprised of two major and opposing sides, that of first-major-side 103 and that of second-major-side 153. See e.g., FIG. 1; and compare FIG. 2 to FIG. 3. In some embodiments, first-major-side 103 may be attached to and/or in communication with second-major-side 153 along peripheral boundary 140. See e.g., FIG. 1. In some embodiments, first-major-side 103 may be more flat (i.e., flatter) than second-major-side 153. In some embodiments, second-major-side 153 may be more curved than first-major-side 103. See e.g., figures FIG. 4, FIG. 5, FIG. 6, and FIG. 7.

Continuing discussing first-major-side 103 and second-major-side 153, in some embodiments, disposed on a lower portion of first-major-side 103 and/or on a lower portion of second-major-side 153 may be one or more of: controls, connectors, electrodes, graphics, images, artwork, branding, trademarks, taglines, logos, combinations thereof, and/or the like. See e.g., FIG. 2 and FIG. 3. For example, and without limiting the scope of the present invention, first-major-side 103 may comprise one or more of: control 120, control 125, control 130, graphic 137, combinations thereof, and/or the like. See e.g., FIG. 1 and FIG. 2. In alternative embodiments, second-major-side 153 may comprise one or more of: control 120, control 125, control 130, graphic 137, combinations thereof, and/or the like.

In some embodiments, control 120, control 125, and/or control 130 may be buttons and/or switches configured to be engaged by a user's finger (including thumb) for operating a given skincare device (100/800/1500/2200/2900/3600). See e.g., FIG. 1, FIG. 8, FIG. 15, FIG. 22, FIG. 29, and FIG. 36. In some embodiments, control 120, control 125, and/or control 130 may be input means operatively connected to one or more processors and/or PCBs (printed circuit board(s)). In some embodiments, the one or more processors and/or PCBs may be located within a given main-body 203/903/3703 and/or within a given base 105/805.

In some embodiments, control 120 may be used to turn on (power up) a given skincare device (100/800/1500/2200/2900/3600) and/or to turn off (power down) the given skincare device. In some embodiments, a user pressing and hold control 120 for at least a predetermined amount of time may be used to turn on (power up) a given skincare device and/or to turn off (power down) the given skincare device. In some embodiments, control 120 may be used to select and/or cycle various operating programs and/or setting of the given skincare device.

When a given skincare device 100/800/1500/2200/2900/3600 may be switched ON into at least one normal mode, for cleaning the skin using vibrations, for example, one or more (e.g., oscillating) motors may provide vibrations and/or pulsations to various external surfaces of the given skincare device, for transmitting such vibrations and/or pulsation, through physical contact, to regions of the skin. For example, and without limiting the scope of the present invention, such vibrations and/or pulsations may be transmitted from the given motor(s) to and through a given pad (e.g., first-pad and/or second-pad), to smooth-plate 1501, and/or to a given base 105/805. Note, the pads (e.g., first-pad and/or second-pad), the touch-points, smooth-plate 1501 are discussed further below. For example, and without limiting the scope of the present invention, such vibrations and/or pulsations may be transmitted from the given motor(s) to and through a given pad (e.g., first-pad and/or second-pad) and through that given pad's various touch-points (such as, but not limited to, touch-points 110 and/or 115). Then vibrations and/or pulsations that are transmitted to the skin and along with touch-points skin contact, may be used to cleanse the skin by loosening and/or removing dead skin cells, particulates, contaminants, bacteria, oils, and/or the like from the skin and/or from skin pores. Motor(s) for generating vibrations and/or pulsations may be located within main-body 203/903/3703 and/or within base 105/805.

In some embodiments, control 130 may be used to select: a next function; a next setting; a next program; a next parameter; a next light color; a next light pattern; a higher output; a faster output; a higher vibration; a faster vibration; a higher speed; a faster speed; a higher temperature; increased heating; faster heating; increased cooling; faster cooling; louder volume; and/or the like.

In some embodiments, control 125 may be used to select: a previous/prior function; a previous/prior setting; a previous/prior program; a previous/prior parameter; a previous/prior light color; a previous/prior light pattern; a lower output; a slower output; a lower vibration; a slower vibration; a lower speed; a slower speed; a lower temperature; decreased heating; slower heating; decreased cooling; slower cooling; lower volume; and/or the like. In some embodiments, control 130 and control 125 may provide opposite inputs, with respect to each other.

In some embodiments, control 120, control 125, and/or control 130 may be located on: first-major-side 103, second-major-side 153, bottom 219, first-major-side 803, second-major-side 853, bottom 919, exterior-surface-of-base 1405, surface-of-bottom 2805, first-major-side 3606, second-major-side 3653, and/or the like.

In some embodiments, the given skincare device (100/800/1500/2200/2900/3600) may be in wireless communication with a separate computer (such as, but not limited to, a smartphone, a laptop, a tablet computer, and/or the like), and the given skincare device may be controlled through that separate computer and the wireless connection. In some embodiments, the given skincare device (100/800/1500/2200/2900/3600), in its main-body (203/903/3703), may comprise one or more: WiFi modules, antennas, radios, Bluetooth chips, network adapters, electronics components configured for communication via radio frequencies, combinations thereof, and/or the like.

For example, and without limiting the scope of the present invention, second-major-side 153 may comprise one or more of: connector 301, graphic 137, combinations thereof, and/or the like. See e.g., FIG. 3. In alternative embodiments, first-major-side 103 may comprise one or more of: connector 301, graphic 137, combinations thereof, and/or the like. In some embodiments, connector 301 may be configured to removably attach to a complimentary/compatible cabled connector for receiving electrical power and/or for communication with a separate computer (such as, but not limited to, a smartphone, a laptop, a tablet computer, and/or the like) (such as, but not limited to, to receive a firmware update/change). In some embodiments, connector 301 may be an electrical power receiving charging port. In some embodiments, connector 301 may be a communications port for electrical and/or optical communications. In some embodiments, connector 301 may be female configured connector. In some embodiments, connector 301 may be located on first-major-side 103, second-major-side 153, bottom 219, first-major-side 803, second-major-side 853, bottom 919, exterior-surface-of-base 1405, surface-of-bottom 2805, first-major-side 3606, second-major-side 3653, and/or the like.

In some embodiments, graphics 137 may be one or more of: graphics, images, artwork, branding, trademarks, taglines, logos, language, wording, numbers, combinations thereof, and/or the like—on exterior surfaces of first-major-side 103 and/or second-major-side 153. See e.g., FIG. 1, FIG. 2, and FIG. 3.

Continuing discussing main-body 203, in some embodiments, each major-surface may comprise a pad (e.g., a first-pad or a second-pad). In some embodiments, first-major-surface 103 may comprise first-pad 107. In some embodiments, second-major-surface 153 may comprise second-pad 157. In some embodiments, on an upper portion of first-major-surface 103 may be first-pad 107. In some embodiments, on an upper portion of second-major-surface 153 may be second-pad 157. In some embodiments, on an upper portion of main-body 203 may be first-pad 107 on a same side as first-major-side 103; and disposed opposite on the other side of main-body 203 on the same side as second-major-side 153, may be second-pad 157. In some embodiments, when viewed from a front view (FIG. 2) and/or when viewed from a rear/back view (FIG. 3), each pad (first-pad 107 and second-pad 157, respectively) may be substantially shaped as: a wedge with round corners; as a pie shape with rounded corners; as a triangle with rounded corners; or the like; and with a plurality of protrusions, referred to as touch-points. In some embodiments, a plurality of touch-points 110 may protrude from first-pad 107. In some embodiments, a plurality of touch-points 115 may protrude from second-pad 157. See e.g., FIG. 1, FIG. 2, and FIG. 3.

In some embodiments, a given pad (e.g., first-pad 107/807/3607 and/or second-pad 157/857/3657) may be removable, detachable, and/or replaceable from a given main-body 203/903/3703. In some embodiments, a given pad (e.g., first-pad and/or second-pad) may be removable, detachable, and/or replaceable from its respective major-side 103/153/803/853/3603/3653. Thus, different types of pads (e.g., first-pad 107/807/3607 and/or second-pad 157/857/3657), with predetermined and specific touch-point configurations, patterns, and/or layouts may be switched out and used with a single/same skincare device 100/800/1500/2200/2900/3600.

In some embodiments, a given pad (e.g., first-pad 107/807/3607 and/or second-pad 157/857/3657) may be externally covered with one or more substantially (mostly): hygienic, wipeable, cleanable, soft, smooth, non-porous, and/or non-absorbent material(s). In some embodiments, a given pad (e.g., first-pad 107/807/3607 and/or second-pad 157/857/3657) may be externally covered with one or more elastomer, silicone, rubber, combinations thereof, and/or the like materials. In some embodiments, the material(s) may be medical or food grade.

In some embodiments, each plurality of touch-points on a given pad may have a predetermined and fixed (non-movable) spacing. In some embodiments, each plurality of touch-points on a given pad may have a predetermined pattern. In some embodiments, each plurality of touch-points on a given pad may have a single and cohesive predetermined pattern. In some embodiments, the plurality of touch-points of a given pad may provide a uniform and consistent texture of those plurality of touch-points.

In some embodiments, a given pad may only have one type of touch-point. For example, and without limiting the scope of the present invention, in some embodiments, first-pad 107 may have a plurality of touch-points 110 protrusions; whereas, second-pad 157 may have a plurality of touch-points 115 protrusions. See e.g., FIG. 1 through and including FIG. 7.

In some embodiments, first-pad 107 (and/or 807/3607) may comprise a plurality of touch-points 110, wherein each touch-point 110 selected from the plurality of touch-points 110 may be a cylindrical elongate member extending outwards from first-pad 107 (and/or 807/3607) that terminates in a terminal end (i.e., the free-end/unattached end), wherein the plurality of such terminal ends forms at least a portion of the outer exterior portion of first-pad 107 (and/or 807/3607) that may be configured to physically press against the region of human skin.

Each touch-point (110/115) protrusion may be an elongate-member. Each touch-point (110/115) protrusion may a substantially cylindrical member ending in a free-end (i.e., the unattached end/terminal end) that may be rounded, flat topped, pointed, or combinations thereof; and opposing that free-end, the given individual touch-point (110/115) may be attached to a given pad (e.g., first-pad 107/807/3607 and/or second-pad 157/857/3657). Each free-end (unattached end) and/or unattached portion of a given touch-point (110/115) may be configured to removably engage a region of skin of a human. In some embodiments, at least some unattached portion of the touch-points (110/115) may be configured to wash, cleanse, ex-foliate, massage, apply product, remove product, combinations thereof, and/or the like with respect to a region of skin of a human. Each touch-point (110/115) protrusion may have a fixed and predetermined length. Each touch-point (110/115) protrusion may have a fixed and predetermined diameter.

In some embodiments, at least some characteristics of touch-point 110 may differ from those of touch-point 115. For example, and without limiting the scope of the present invention, touch-point 110 may have a different length as compared to touch-point 115. For example, and without limiting the scope of the present invention, touch-point 110 may have a different diameter as compared to touch-point 115. For example, and without limiting the scope of the present invention, a predetermined and fixed distance between two adjacent touch-points 110 may be different from a predetermined and fixed distance between two adjacent touch-points 115. For example, and without limiting the scope of the present invention, touch-point 110 may have a different stiffness, firmness, rigidity, elasticity, durometer, soft-ness and/or the like as compared to touch-point 115. Such differences between touch-point 110 and touch-point 115 may reflect different user preferences for how their skin is to be engaged by the plurality of touch-points. Such differences between touch-point 110 and touch-point 115 may facilitate use of particular touch-points for certain regions of skin;

e.g., some skin regions may be more sensitive to touch than other regions of skin. Such differences between touch-point 110 and touch-point 115 may facilitate different uses of the touch-points; e.g., stiffer touch-points may function better for exfoliating; whereas, softer touch-points may function better for washing.

In some embodiments, each touch-point 110 (or 115) selected from the plurality of touch-points 110 (or 115) may have a same, fixed, and predetermined diameter and length. In some embodiments, the plurality of touch-points 110 (or 115) may be arranged in a pattern so as to have a single consistent texture.

In some embodiments, the plurality of touch-points 110 of the first-pad 107 (or 807/3607) may be deemed a first plurality of touch-points 110, wherein the second-pad 157 (or 857/3657) may comprise a second plurality of touch-points 115, wherein each touch-point selected 115 from the second plurality of touch-points 115 may be a cylindrical elongate member extending outwards from the second-pad 157 (or 857/3657) that may terminate in a terminal end (free-end/unattached end), wherein the terminal ends selected from the second plurality of touch-points 115 may form at least a portion of the outer exterior portion of the second-pad 157 (or 857/3657) that may be configured to physically press against the region of human skin. In some embodiments, each touch-point 115 selected from the second plurality of touch-points 115 may have a same, fixed, and predetermined diameter and length that may differ from the diameter and the length of the touch-points 110 selected from the first plurality of touch-points 110.

In some embodiments, at least one motor (e.g., 4707) of the given skincare device may be operatively linked to second-pad 157 (or 857/3657), such that when the at least one motor (e.g., 4707) may be activated, vibrations are transmitted to the second-pad 157 (or 857/3657), and the such vibrations may also then be transmitted to the plurality of touch-points 115 and then finally onto region of human skin.

In some embodiments, the plurality of electronic components of the given skincare device may comprise a second motor (e.g., 4707) that may be operatively linked to the at least one power-source (e.g., 4705) and to the second-pad 157 (or 857/3657), such that when the second motor may be activated, vibrations are transmitted to the second-pad 157 (or 857/3657), and the such vibrations may also then be transmitted to the plurality of touch-points 115 and then finally onto region of human skin.

Discussing base 105, in some embodiments, base 105 may form a base of skincare device 100. In some embodiments, base 105 may be weighted so as to encourage skincare device 100 in a substantially upright position when base 105 may be resting on a substantially flat and/or horizontal surface, with tip 211 oriented vertically above bottom 219 and bottom 229. That is, in some embodiments, base 105 may be weighted so as to encourage maintaining skincare device 100 in a substantially upright position with respect to the substantially flat and/or horizontal surface that base 105 may be in physical contact with and resting upon. See e.g., FIG. 2 and FIG. 3. Note, bottom 219 may be a bottom of main-body 203 and bottom 229 may be a bottom of base 105. In some embodiments, bottom 219 and bottom 229 may track along substantially parallel paths (as viewed from a front or rear, as in FIG. 2 or FIG. 3). In some embodiments, bottom 229 of base 105 may be rounded and/or curved, configured for removable engagement with a region of skin, which may facilitate skin massage and/or application on skin care products.

In some embodiments, skincare device 100 may comprise base 105 that may be attached (removably so in some embodiments) to bottom 219 of main-body 203; wherein base 105 may comprise an exterior region that is configured for pressing against the region of human skin.

Continuing discussing base 105, in some embodiments, base 105 may substantially house one or more electronics components, such as, but not limited to, PCBs, processors, memory, sensors, electrodes, heaters, coolers, batteries, power sources, connectors 301, motors, network communications hardware, radios, antennas, circuits, switches, controls, circuit elements, combinations thereof, and/or the like. In some embodiments, the given base 105 may comprise electronic components of FIG. 47.

Continuing discussing base 105, in some embodiments, a nature of attachment between base 105 and main-body 203 may be removable attachment. In some embodiments, base 105 may be detachable from main-body 203. In some embodiments, base 105 may be replaceable with respect to main-body 203. In some embodiments, a nature of attachment between base 105 and main-body 203 may be intended for permanent attachment (or at least attachment not intended to be removed by an end-user).

In embodiments where base 105 may be removably attachable to main-body 203, base 105 may be a removable attachment to skincare device 100, for providing diverse and varied additional skin engagement functionality of the given skincare device 100. For example, and without limiting the scope of the present invention, one base 105 may have one or more motors for vibrating base 105; whereas, another different base 105 may have a heater/cooler; whereas, yet another base 105 may have both one or more motors and a heater/cooler; whereas, a yet further still base 105 may have various skin sensors and/or electrodes; and/or the like. These different bases 105 may be swapped out as needed or as desired by the user.

In some embodiments, at least some exterior portions of base 105 (e.g., at least some portion of exterior-surface-of-base 705 shown in FIG. 7) that are configured to removably en-gage/contact human skin may be substantially constructed from one or more of: metal, precious metal, precious stone, glass, gem, gem stone (gemstone), crystal (such as, but not limited to, quartz), salt crystals, salt, stone, natural stone (such as, but not limited to, marble, jade, etc.), a mineral, elastomer, silicone, rubber, plastic, polycarbonate, ceramic, wood, natural wood, combinations thereof, and/or the like. In some embodiments, at least some exterior portions of base 105 may be at least partially covered with a micro-needle textured surface and/or touch-points.

In some embodiments, at least some exterior portions of base 105 (e.g., at least some portion of exterior-surface-of-base 705 shown in FIG. 7) that are configured to removably en-gage/contact human skin may be substantially smooth and/or rounded.

In some embodiments, at least some exterior portions of base 105 may be configured to emit/produce microcurrents into the skin, for such purposes as skin tightening, muscle stimulation (e.g., "e-stem"), cell stimulation, combinations thereof, and/or the like. Such micro currents may be generated by surface electronic circuits, rings, terminals, electrodes (first-electrode 1001 and/or second-electrode 1003), combinations thereof, and/or the like.

In some embodiments, base 105 may comprise its own power-source 4705, and/or a power-source 4705 for the overall given skincare device. In some embodiments, base 105 may comprise its own motor(s) 4707. Motor(s) 4707 in base 105 may facilitate skin massage and/or pushing skin products into skin pores. In some embodiments, base 105 may comprise its own heater/cooler 4709. In some embodiments, heating or cooling functionality from the given heater/cooler 4709 may be used together with pulsations/vibrations from the given motor 4707. In some embodiments, base 105 may comprise its own connector 301, connector 4301, sensors 4711, electrodes, first-electrode 1001, second-electrode 1003, exposed pins/terminals which may be used for sensing and/or for micro current generation/distribution. This may facilitate an ability to sense/monitor skin moisture levels, skin temperature, ambient/room temperature, skin's visible age, face mask product absorption state, effectiveness of skin treatment, amount of makeup/cosmetics applied to skin, amount (e.g., percentage) of makeup/cosmetic removed after cleansing, combinations thereof, and/or the like. Such sensors may be human skin touch based (e.g., touch activated and read when touching human skin). All such data may be relayed (transmitted) to a separate computing-device 4803 (e.g., a smartphone, a tablet computer, a laptop, etc.) by using the given skincare device's communication module 4713.

In some embodiments, skincare device 100 may comprise one or more indicators 135. In some embodiments, a given indicator 135 may be a light source and/or a region of skincare device 100 configured to emit light. In some embodiments, indicator 135 may have an exterior region that is substantially optically transparent. In some embodiments, indicator 135 may be one or more light emitting diodes (LEDs) and/or the like. In some embodiments, indicator 135 may cover over or more LEDs, but allow light to escape such a cover. In some embodiments, indicator 135 may be one or more light strips. In some embodiments, indicator 135 may be one or more LED strips (and/or LED arrays). In some embodiments, indicator 135 may cover over one or more light strips, but allowing light to escape such a cover. In some embodiments, indicator 135 may cover over one or more LED strips, but allowing light to escape such a cover. In some embodiments, indicator 135 may emit light of a predetermined color. In some embodiments, indicator 135 may emit light of predetermined and different colors. In some embodiments, indicator 135 may emit light in a predetermined pattern. In some embodiments, indicator 135 may emit light in a predetermined color(s) and/or pattern. In some embodiments, indicator 135 may be light guide ring around a bottom portion of a main-body 203/903/3703 of the given skincare device 100/800/1500/2200/2900/3600. In some embodiments, light emitted by indicator 135 may indicate a mode operation, progress, status and/or a change in status of skincare device 100 or portion thereof. In some embodiments, such a status or a change in status may refer to one or more: on/off distinction, battery level (power source level), modes of operation, temperature (skin and/or ambient air temperature), vibration, vibration frequency, wave pattern, intensity, duration, time interval, combinations thereof, and the like. In some embodiments, indicator 135 may be located on an exterior of skincare device 100. In some embodiments, indicator 135 may be located on an exterior of main-body 203. In some embodiments, indicator 135 may be component(s) of main-body 203. In some embodiments, indicator 135 may be located on an exterior of base 105. In some embodiments, indicator 135 may be component(s) of base 105. In some embodiments, indicator 135 may be located on an exterior of first-major-side 103. In some embodiments, indicator 135 may be located on an exterior of second-major-side 153. In some embodiments, indicator 135 may be a continuous band that may circumscribe an exterior of main-body 203, base 105, combinations thereof, and/or the like. See e.g., FIG. 1 through and including FIG. 5.

In some embodiments, at least one visual indicator 135 may be configured to emit light of one or more of: a single color, different colors, multiple colors, alternating colors, alternating intensity, a predetermined pattern of light emission, combinations thereof, and/or the like. In some embodiments, the light emitted from the at least one visual indicator 135 may indicate a status, a change in status of the given skincare device, combinations thereof, and/or the like. In some embodiments, at least one visual indicator 135 may be configured as a light strip ring that circumscribes an entirety of an exterior of the skincare device. In some embodiments, indicator 135 may run substantially orthogonal (perpendicular) to boundary 140 (840/3740).

Figure 9:
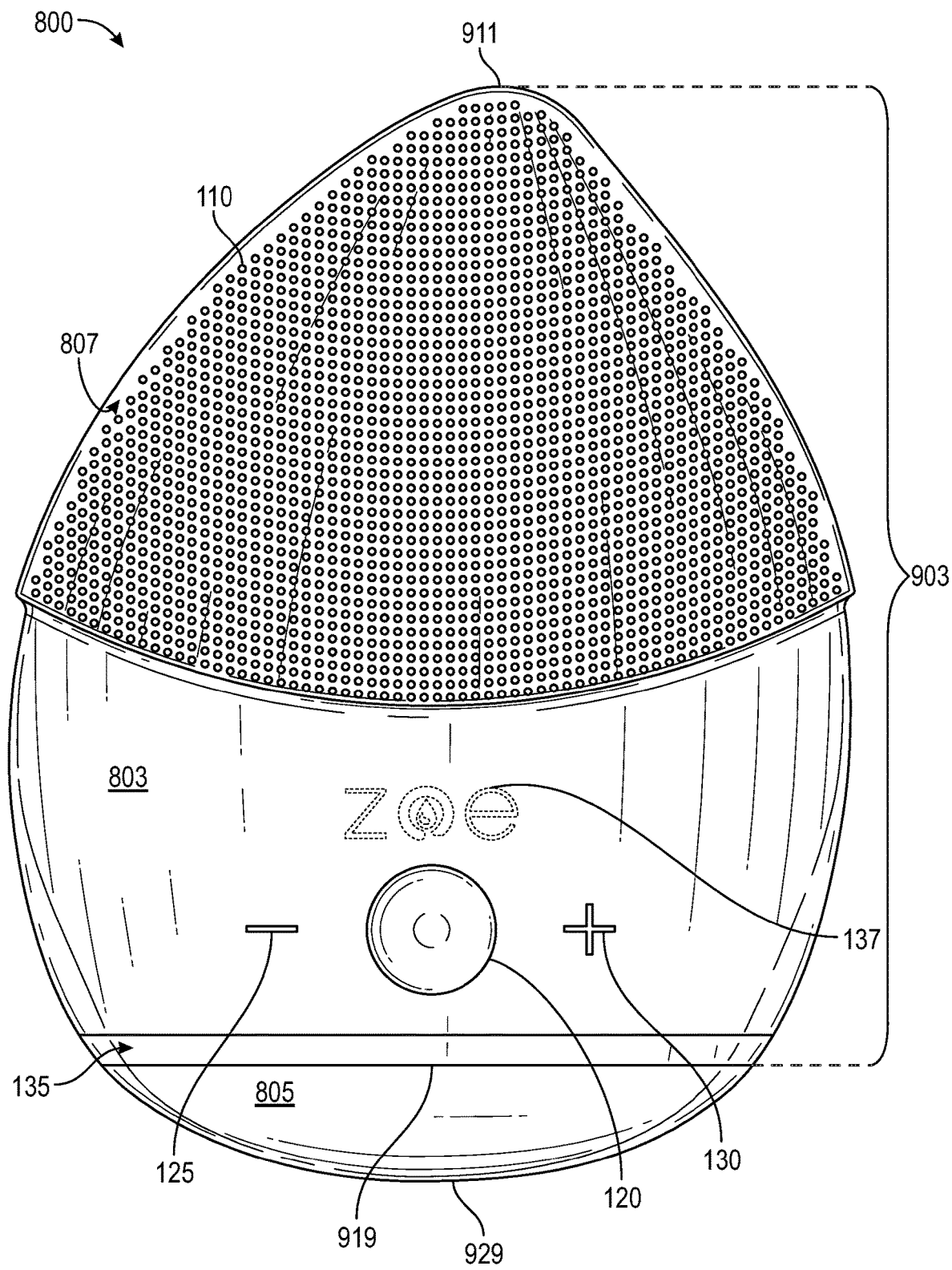
FIG. 9 depicts a front view of the second embodiment.
Figure 10:
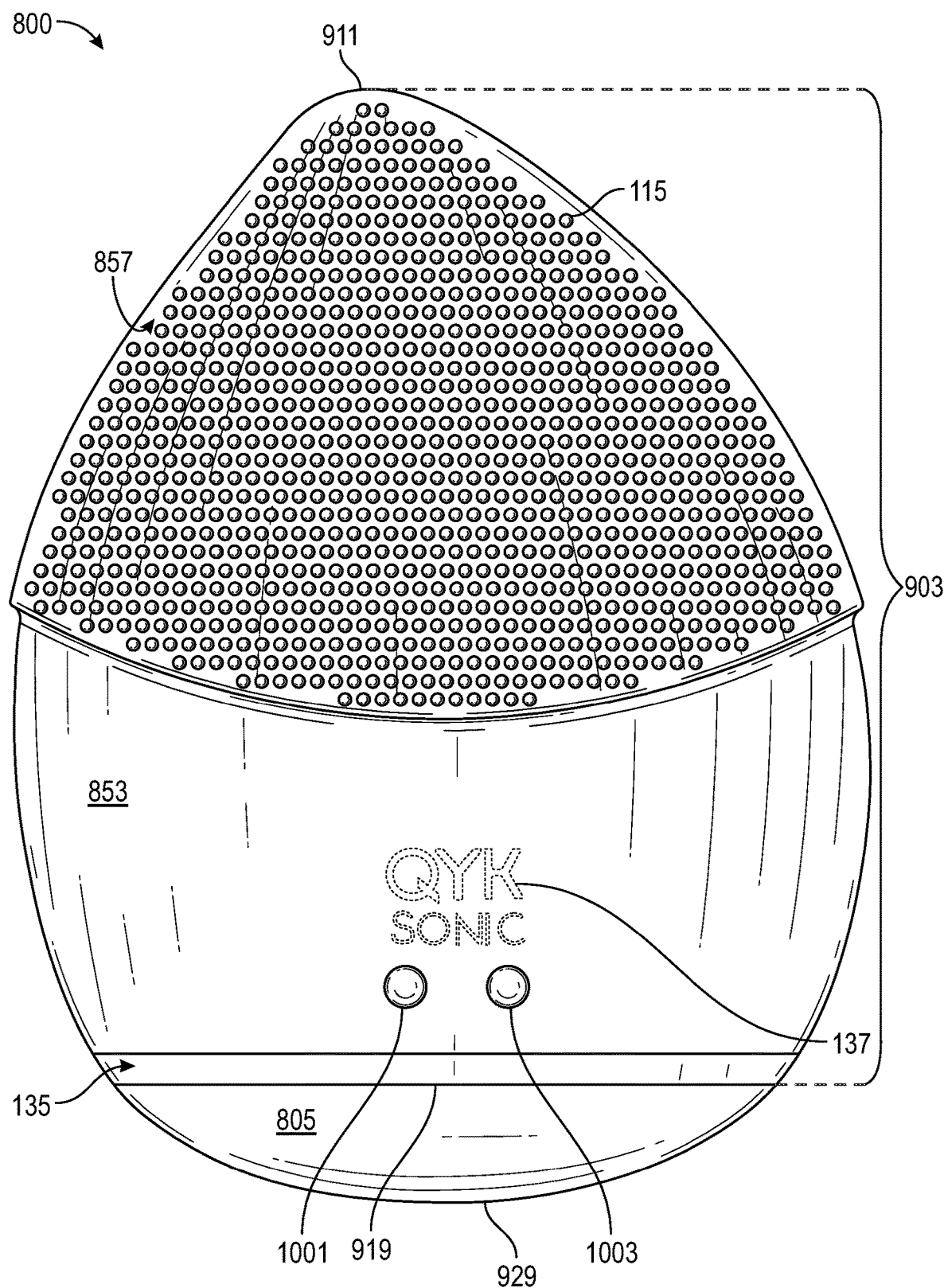
FIG. 10 depicts a back view of the second embodiment.

As noted, skincare device 800 is shown in figures FIG. 8 through and including FIG. 14. Skincare device 800 may differ from skincare device 100, by skincare device 800 including (comprising) first-electrode 1001 and/or second-electrode 1003 (see e.g., FIG. 10). Skincare device 800 may differ from skincare device 100, by skincare device 800 including (comprising) a differently shaped base 805 than the base 105 of skincare device 100 (compare FIG. 9 to FIG. 2). Skincare device 800 may differ from skincare device 100, by skincare device 800 including (comprising) indicator 135 as a bottom portion of main-body 903; whereas, in some embodiments of skincare device 100, indicator 135 may be associated with base 105.

Continuing discussing skincare device 800, in some embodiments, skincare device 800 may be comprised of a main-body 903 and a base 805. See e.g., FIG. 9. In some embodiments, base 805 may be attached to a bottom 919 of main-base 903.

Figure 11:
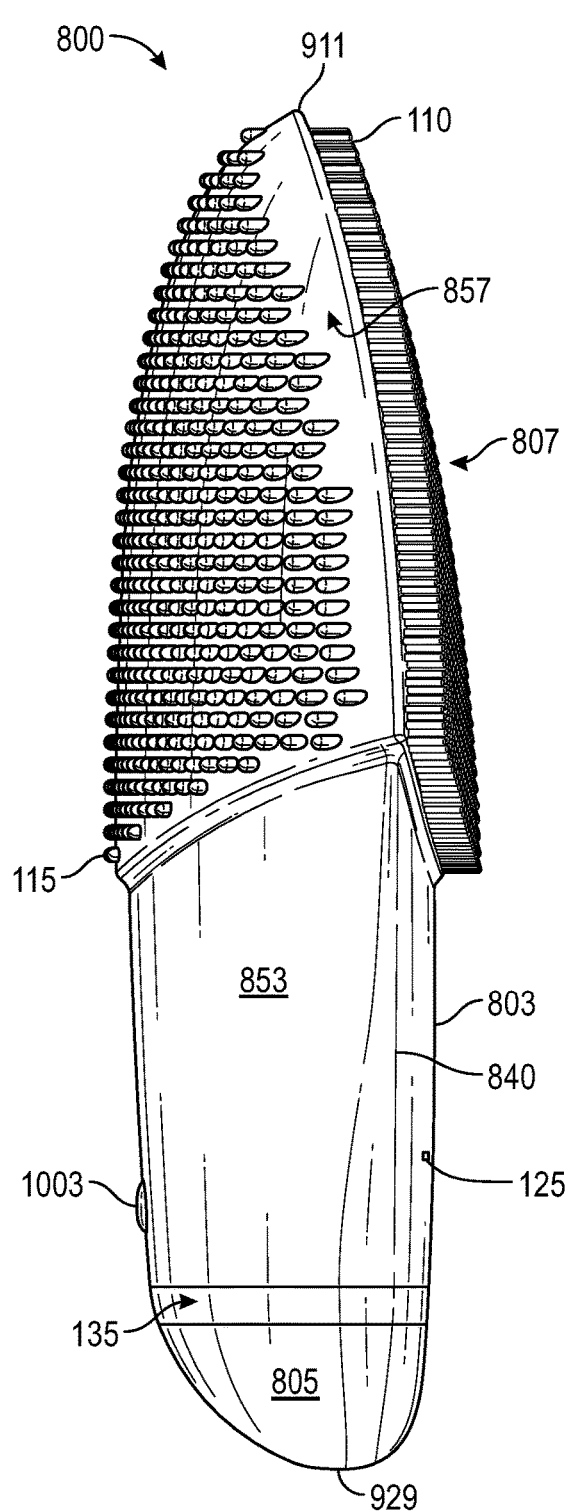
FIG. 11 depicts a left-side view of the second embodiment.
Figure 12:
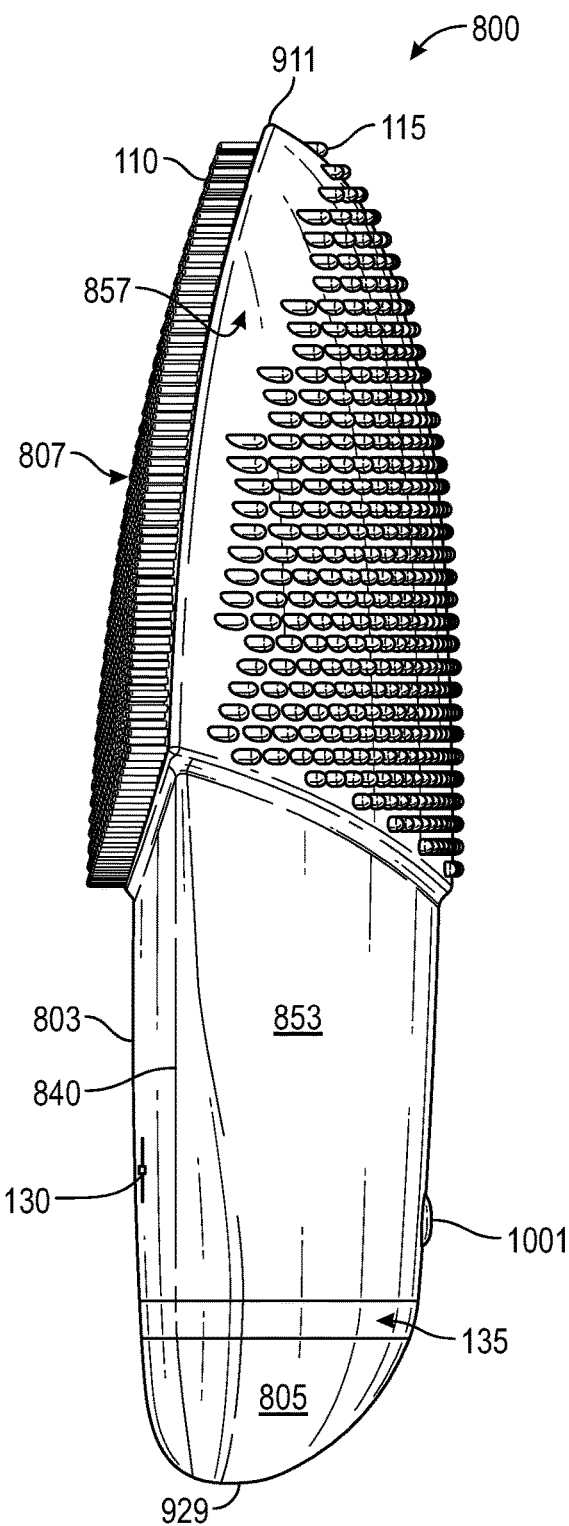
FIG. 12 depicts a right-side view of the second embodiment.
Figure 13:
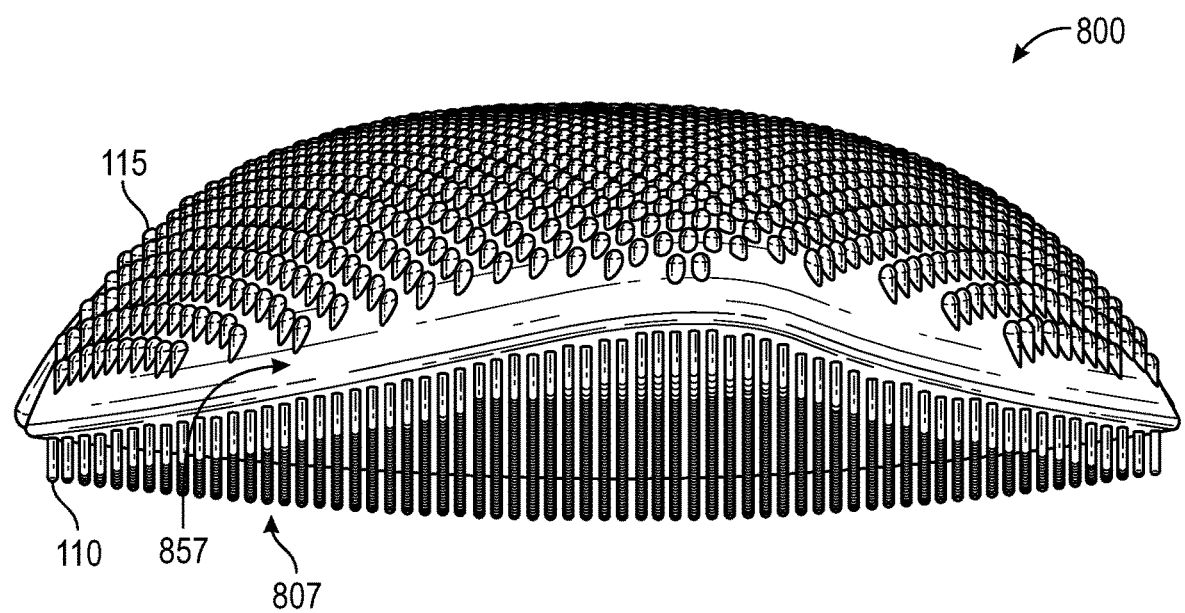
FIG. 13 depicts a top view of the second embodiment.

In some embodiments, main-body 903 may be configured to be a portable (mobile) hand-held device. In some embodiments, main-body 903 may be substantially similar to main-body 203 in terms of functionality, purpose, and/or benefits. In some embodiments, main-body 903 may be configured to be held and used by one human hand. In some embodiments, main-body 903 may be a three-dimensional (3D) device. From a front view (e.g., FIG. 9) and/or a back/rear view (e.g., FIG. 10), main-body 903 may be substantially or generally shaped with curved sides, a top 911 point (wherein that point may be rounded) and a substantially flat bottom 919. In some embodiments, main-body 903 may run from top 911 to (flat) bottom 919, see e.g., FIG. 9 and/or FIG. 10. In some embodiments, main-body 903 may have a fixed and predetermined thickness (see e.g., FIG. 11 and/or FIG. 12) of about 0.5 inch to about 1.5 inches, plus or minus 0.1 inch.

In some embodiments, main-body 903 may substantially house one or more electronics components, such as, but not limited to, PCBs, processors, memory, sensors, electrodes, heaters, coolers, batteries, power sources, connectors 301, motors, network communications hardware, radios, antennas, circuits, switches, controls, circuit elements, combinations thereof, and/or the like.

Continuing discussing main-body 903, in some embodiments, main-body 903 may be comprised of two major and opposing sides, that of first-major-side 803 and that of second-major-side 853. See e.g., FIG. 8; and compare FIG. 9 to FIG. 10. In some embodiments, first-major-side 803 may be attached to and/or in communication with second-major-side 853 along peripheral boundary 840. See e.g., FIG. 8. In some embodiments, first-major-side 803 may be more flat than second-major-side 853. In some embodiments, second-major-side 853 may be more curved than first-major-side 803. See e.g., figures FIG. 11, FIG. 12, FIG. 13, and FIG. 14.

In some embodiments, first-major-side 803 may be substantially similar to first-major-side 103 in terms of function, purpose, and/or benefit; but may differ in shape. In some embodiments, second-major-side 853 may be substantially similar to second-major-side 153 in terms of function, purpose, and/or benefit; but may differ in shape. In some embodiments, boundary 840 may be substantially similar to boundary 140 in terms of function, purpose, and/or benefit; but may differ in shape.

Continuing discussing first-major-side 803 and second-major-side 853, in some embodiments, disposed on a lower portion of first-major-side 803 and/or on a lower portion of second-major-side 853 may be one or more of: controls, connectors, electrodes, graphics, images, artwork, branding, trademarks, taglines, logos, combinations thereof, and/or the like. See e.g., FIG. 9 and FIG. 10. For example, and without limiting the scope of the present invention, first-major-side 803 may comprise one or more of: control 120, control 125, control 130, graphic 137, combinations thereof, and/or the like. See e.g., FIG. 8 and FIG. 9. In alternative embodiments, second-major-side 853 may comprise one or more of: control 120, control 125, control 130, graphic 137, combinations thereof, and/or the like.

In some embodiments, control 120, control 125, and/or control 130 may be located on: first-major-side 803, second-major-side 853, bottom 919, exterior-surface-of-base 1405, combinations thereof, and/or the like.

In some embodiments, connector 301 may be located on first-major-side 803, second-major-side 853, bottom 919, exterior-surface-of-base 1405, combinations thereof, and/or the like.

In some embodiments, graphics 137 may be one or more of: graphics, images, artwork, branding, trademarks, taglines, logos, language, wording, numbers, combinations thereof, and/or the like—on exterior surfaces of first-major-side 803 and/or of second-major-side 853. See e.g., FIG. 8, FIG. 9, and FIG. 10.

Continuing discussing main-body 903, in some embodiments, each major-surface may comprise a pad. In some embodiments, first-major-surface 803 may comprise first-pad 807. In some embodiments, second-major-surface 853 may comprise second-pad 857. In some embodiments, on an upper portion of first-major-surface 803 may be first-pad 807. In some embodiments, on an upper portion of second-major-surface 853 may be second-pad 857. In some embodiments, on an upper portion of main-body 903 may be first-pad 807 on a same side as first-major-side 803; and disposed opposite on the other side of main-body 903 on the same side as second-major-side 853, may be second-pad 857. In some embodiments, when viewed from a front view (FIG. 9) and/or when viewed from a rear/back view (FIG. 10), each pad (first-pad 807 and second-pad 857, respectively) may be substantially shaped as: a wedge with round corners; as a pie shape with rounded corners; as a triangle with rounded corners; or the like; and with a plurality of protrusions, referred to as touch-points. In some embodiments, a plurality of touch-points 110 may protrude from first-pad 807. In some embodiments, a plurality of touch-points 115 may protrude from second-pad 857. See e.g., FIG. 8, FIG. 9, and FIG. 10.

In some embodiments, a given pad may only have one type of touch-point. For example, and without limiting the scope of the present invention, in some embodiments, first-pad 807 may have a plurality of touch-points 110 protrusions; whereas, second-pad 857 may have a plurality of touch-points 115 protrusions. See e.g., FIG. 8 through and including FIG. 14.

Each touch-point (110/115) protrusion may a substantially cylindrical member ending in a free-end (an unattached end) that may be rounded; and opposing that free-end may be attached to a given pad (e.g., first-pad 807 and/or second-pad 857).

Discussing base 805, in some embodiments, base 805 may form a base of skincare device 800. In some embodiments, base 805 may be weighted so as to encourage skincare device 800 in a substantially upright position when base 805 may be resting on a substantially flat and/or horizontal surface, with tip 911 oriented vertically above bottom 919 and bottom 929. That is, in some embodiments, base 805 may be weighted so as to encourage maintaining skincare device 800 in a substantially upright position with respect to the substantially flat and/or horizontal surface that base 805 may be in physical contact with and resting upon. See e.g., FIG. 9 and FIG. 10. Note, bottom 919 may be a bottom of main-body 903 and bottom 929 may be a bottom of base 805. In some embodiments, bottom 919 may be substantially flat; whereas, bottom 929 may be curved and/or rounded. In some embodiments, bottom 929 of base 805 may be rounded and/or curved, configured for removable engagement with a region of skin, which may facilitate skin massage and/or application on skin care products. See e.g., FIG. 9 and FIG. 10.

In some embodiments, the given skincare device (e.g., 800/1500/2200/2900/3600) may comprise base 805 that may be attached (removably so in some embodiments) to the bottom (e.g., 919) of the given main-body 903/3703; wherein base 805 may comprise an exterior region that is configured for pressing against the region of human skin.

Continuing discussing base 805, in some embodiments, base 805 may substantially house one or more electronics components, such as, but not limited to, PCBs, processors, memory, sensors, electrodes, heaters, coolers, batteries, power sources, connectors 301, motors, network communications hardware, radios, antennas, circuits, switches, controls, circuit elements, combinations thereof, and/or the like. In some embodiments, the given base 805 may comprise electronic components of FIG. 47.

Continuing discussing base 805, in some embodiments, a nature of attachment between base 805 and main-body 903 may be removable attachment. In some embodiments, base 805 may be detachable from main-body 903. In some embodiments, base 805 may be replaceable with respect to main-body 903.

In some embodiments, such removable attachment (between a base 105/805 and its main-body 203/903) may be accomplished by one or more mechanical fasteners. In some embodiments, the one or more mechanical fasteners may comprise at least one magnet and at least one magnetically attractable material that may be brought into proximity of the at least one magnet for removable magnetic attachment. In some embodiments, the at least one magnet may be in or proximate to bottom 819; whereas, the at least one magnetically attractable material may in or proximate to an upper/top surface of base 805, disposed away from bottom 829. Or alternatively, in some embodiments, the at least one magnetically attractable material may be in or proximate to bottom 819; whereas, the at least one magnet may in or proximate to an upper/top surface of base 805, disposed away from bottom 829. In some embodiments, the at least one magnetically attractable material may be another magnet. In some embodiments, the one or more mechanical fasteners may be selected from: a snap fit, a press fit, a friction fit, a plurality of hooks for pairing with a plurality of loops (as in a Velcro type fastener), combinations thereof, and/or the like.

Continuing discussing base 805, in some embodiments, a nature of attachment between base 805 and main-body 903 may be intended for permanent attachment (or at least attachment not intended to be removed by an end-user).

In embodiments where base 805 may be removably attachable to main-body 903, base 805 may be a removable attachment to skincare device 800, for providing diverse and varied additional skin engagement functionality of the given skincare device 800. For example, and without limiting the scope of the present invention, one base 805 may have one or more motors for vibrating base 805; whereas, another different base 805 may have a heater/cooler; whereas, yet another base 805 may have both one or more motors and a heater/cooler; whereas, a yet further still base 805 may have various skin sensors and/or electrodes; and/or the like. These different bases 805 may be swapped out as needed or as desired by the user.

In some embodiments, at least some exterior portions of base 805 (e.g., at least some portion of exterior-surface-of-base 1405 shown in FIG. 14) that are configured to removably engage/contact human skin may be substantially constructed from one or more of: metal, precious metal, precious stone, glass, gem, gem stone (gemstone), crystal (such as, but not limited to, quartz), salt crystals, salt, stone, natural stone (such as, but not limited to, marble, jade, etc.), elastomer, silicone, rubber, plastic, polycarbonate, ceramic, wood, natural wood, combinations thereof, and/or the like. In some embodiments, at least some exterior portions of base 805 may be at least partially covered with a micro-needle textured surface and/or touch-points.

In some embodiments, at least some exterior portions of base 805 (e.g., at least some portion of exterior-surface-of-base 1405 shown in FIG. 14) that are configured to removably engage/contact human skin may be substantially smooth and/or rounded.

In some embodiments, at least some exterior portions of base 805 may be configured to emit/produce microcurrents into the skin, for such purposes as skin tightening, muscle stimulation (e.g., "e-stem"), cell stimulation, combinations thereof, and/or the like. Such micro currents may be generated by surface electronic circuits, rings, terminals, electrodes (first-electrode 1001 and/or second-electrode 1003), combinations thereof, and/or the like.

In some embodiments, base 805 may comprise its own power-source 4705, and/or a power-source 4705 for the overall given skincare device. In some embodiments, base 805 may comprise its own motor(s) 4707. Motor(s) 4707 in base 805 may facilitate skin massage and/or pushing skin products into skin pores. In some embodiments, base 805 may comprise its own heater/cooler 4709. In some embodiments, heating or cooling functionality from the given heater/cooler 4709 may be used together with pulsations/vibrations from the given motor 4707. In some embodiments, base 805 may comprise its own connector 301, connector 4301, sensors 4711, electrodes, first-electrode 1001, second-electrode 1003, exposed pins/terminals which may be used for sensing and/or for micro current generation/distribution. This may facilitate an ability to sense/monitor skin moisture levels, skin temperature, ambient/room temperature, skin's visible age, face mask product absorption state, effectiveness of skin treatment, amount of makeup/cosmetics applied to skin, amount (e.g., percentage) of makeup/cosmetic removed after cleansing, combinations thereof, and/or the like. Such sensors may be human skin touch based (e.g., touch activated and read when touching human skin). All such data may be relayed (transmitted) to a separate computing-device 4803 (e.g., a smartphone, a tablet computer, a laptop, etc.) by using the given skincare device's communication module 4713.

In some embodiments, skincare device 800 may comprise one or more indicators 135. In some embodiments, a given indicator 135 may be a light source and/or a region of skincare device 800 configured to emit light. In some embodiments, light emitted by indicator 135 may indicate a status and/or a change in status of skincare device 800 or portion thereof. In some embodiments, indicator 135 may be located on an exterior of skincare device 800. In some embodiments, indicator 135 may be located on an exterior of main-body 903. In some embodiments, indicator 135 may be component(s) of main-body 903. In some embodiments, indicator 135 may be located on an exterior of base 805. In some embodiments, indicator 135 may be component(s) of base 805. In some embodiments, indicator 135 may be located on an exterior of first-major-side 803. In some embodiments, indicator 135 may be located on an exterior of second-major-side 853. In some embodiments, indicator 135 may be a continuous band that may circumscribe an exterior of main-body 903, base 805, combinations thereof, and/or the like. See e.g., FIG. 8 through and including FIG. 14.

In some embodiments, skincare device 800 may comprise at least one electrode, such as first-electrode 1001 and/or second-electrode 1003. In some embodiments, first-electrode 1001 and/or second-electrode 1003 may be located on an exterior surface of skincare device 800 (see e.g., FIG. 10). In some embodiments, first-electrode 1001 and/or second-electrode 1003 may be located on second-major-side 853 (see e.g., FIG. 10). In some embodiments, first-electrode 1001 and/or second-electrode 1003 may be located on first-major-side 803. In some embodiments, first-electrode 1001 and/or second-electrode 1003 may be located on base 805. In some embodiments, first-electrode 1001 and/or second-electrode 1003 may be located on exterior-surface-of-base 1405 of base 805.

In some embodiments, first-electrode 1001 and/or second-electrode 1003 may function as an input means, i.e., for receiving inputs to electronics of skincare device 800. For example, and without limiting the scope of the present invention, first-electrode 1001 and/or second-electrode 1003 may be sensors to measuring various properties of the surfaces (e.g., human skin and/or a substance on human skin) in physical contact with such sensors. For example, and without limiting the scope of the present invention, first-electrode 1001 and/or second-electrode 1003 may be sensors for measuring electrical potential, resistance, capacitance, combinations thereof, and/or the like.

In some embodiments, first-electrode 1001 and/or second-electrode 1003 may function as an output means, i.e., for outputting to human skin in contact with such electrodes. In some embodiments, first-electrode 1001 and/or second-electrode 1003 may be electrodes for outputting an electrical pulse to a given region of human skin for stimulating that region of human skin and/or for stimulating tissue (e.g., muscle) proximate (e.g., below) that region of human skin. For example, and without limiting the scope of the present invention, first-electrode 1001 and/or second-electrode 1003 may be electrodes for outputting voltage and/or current (e.g., micro-current) to human skin in physical contact with the electrodes. Such electrical stimulation of human skin may cause muscles proximate to the stimulated region of skin to contract.

Figure 16:
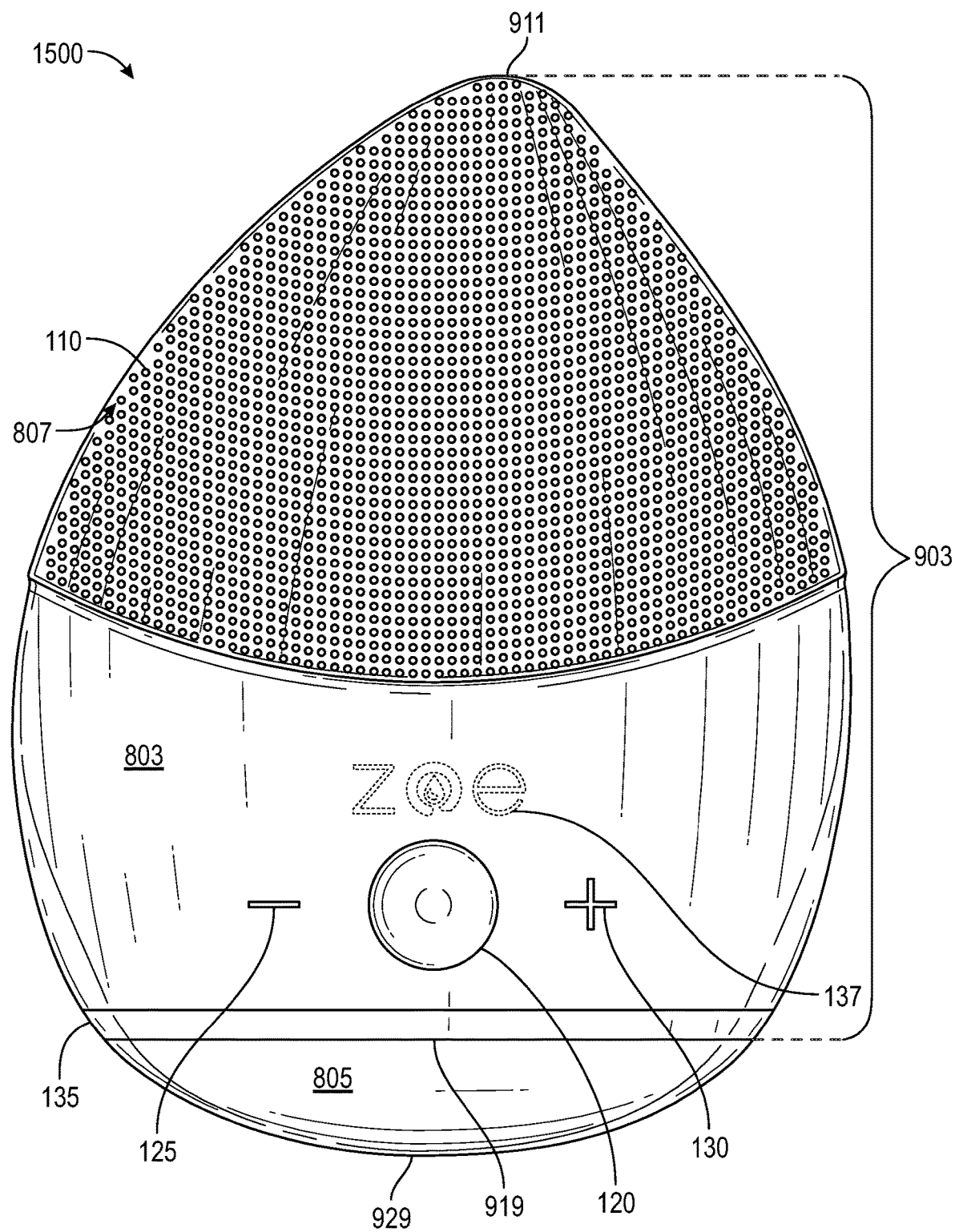
FIG. 16 depicts a front view of the third embodiment.
Figure 17:
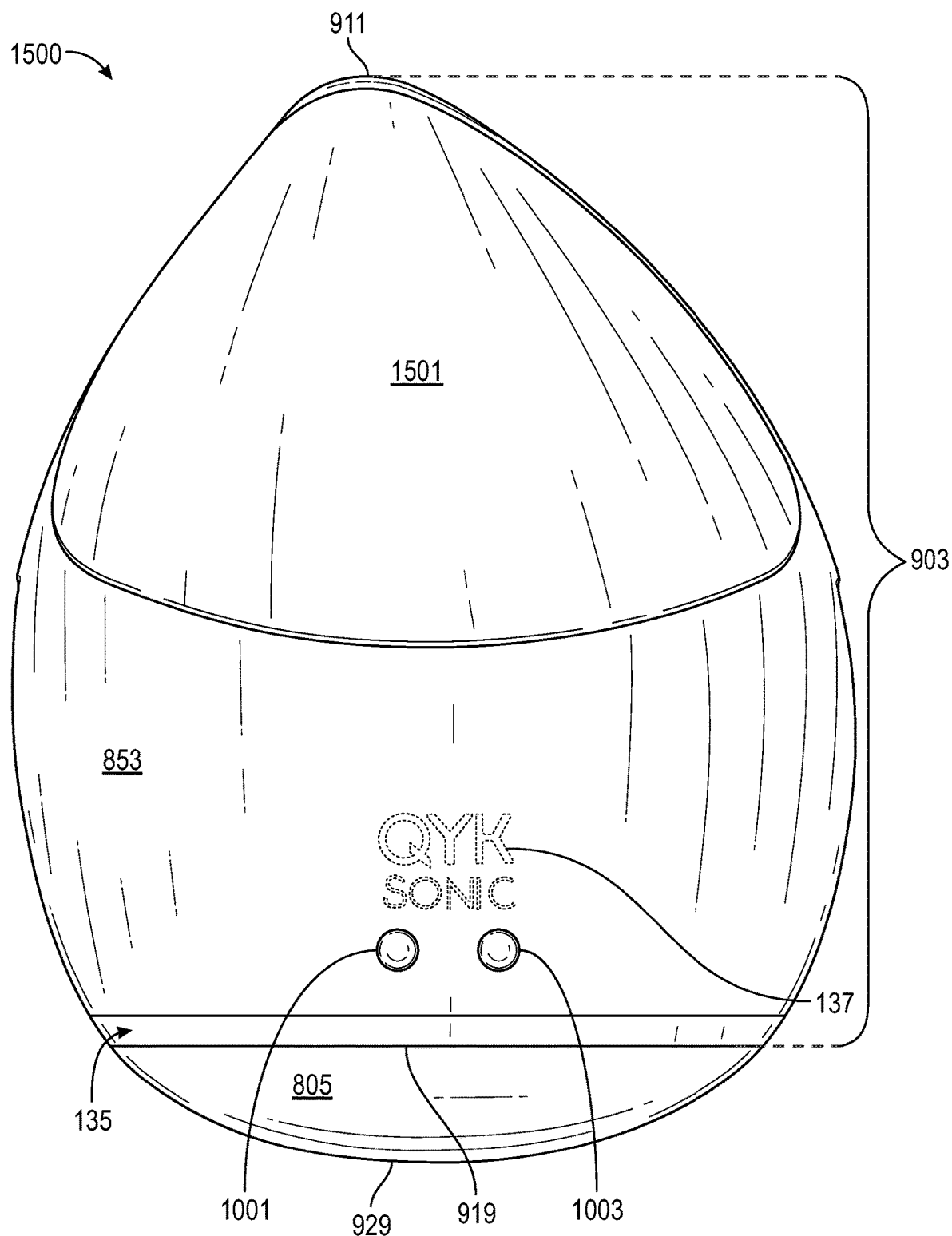
FIG. 17 depicts a back view of the third embodiment.
Figure 18:
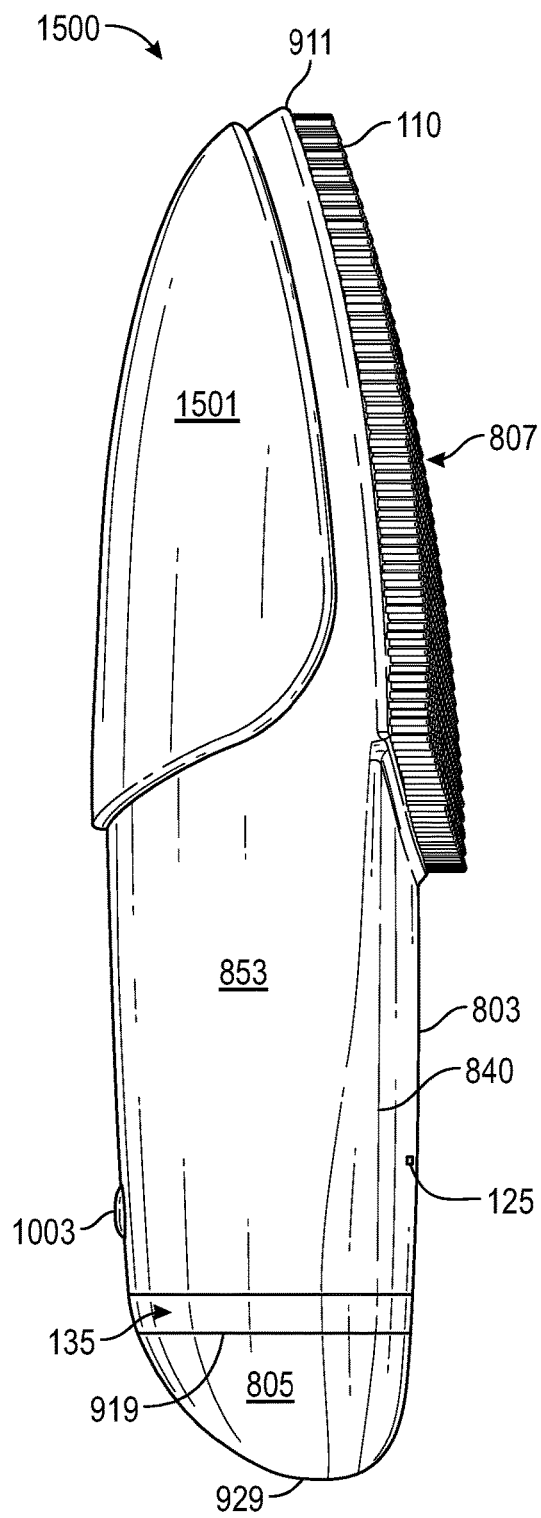
FIG. 18 depicts a left-side view of the third embodiment.
Figure 19:
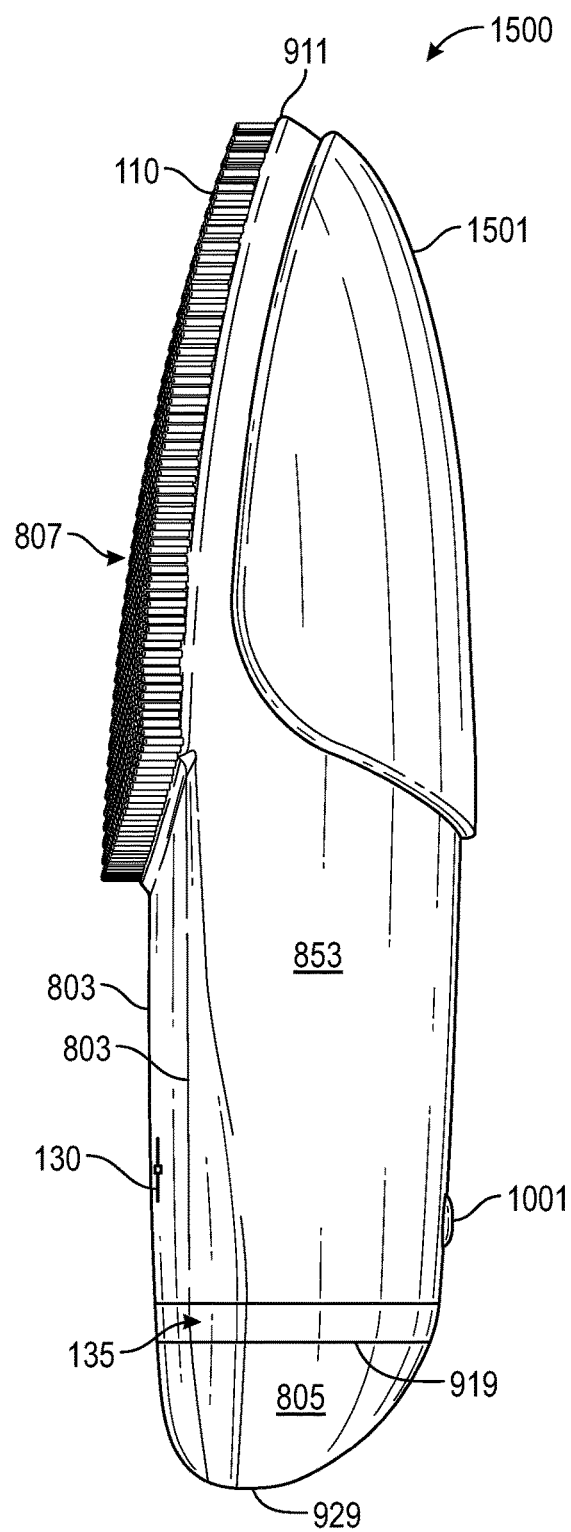
FIG. 19 depicts a right-side view of the third embodiment.
Figure 20:
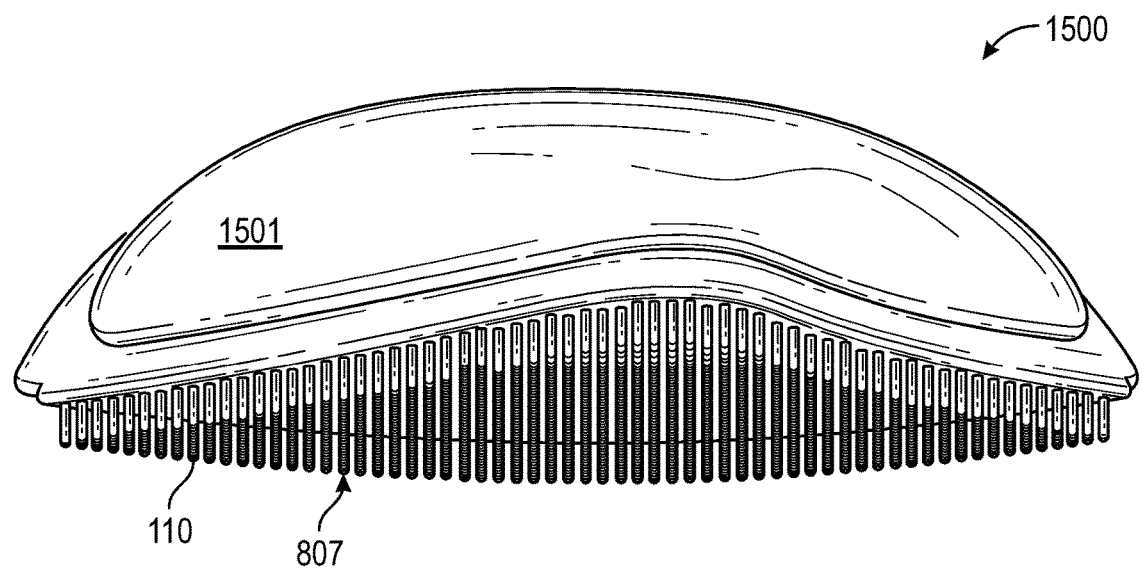
FIG. 20 depicts a top view of the third embodiment.

As noted, skincare device 1500 is shown in figures FIG. 15 through and including FIG. 21. In some embodiments, skincare device 1500 and skincare device 800 may share a same overall shape (e.g., compare FIG. 16 to FIG. 9). In some embodiments, skincare device 1500 and skincare device 800 may share at least some components and/or some electronics. In some embodiments, skincare device 1500 and skincare device 800 may share a same: first-major-side 803, base 805, first-pad 807, boundary 840, second-major-side 853 (but without second-pad 857), main-body 903, top 911, bottom 919, bottom 929, first-electrode 1001, second-electrode 1003, and/or exterior-surface-of-base 1405. These components, parts, structures, and/or electronics for skincare device 1500 may be as substantially discussed above for skincare device 800, aside from differences noted below.

In some embodiments, skincare device 1500 may differ from skincare device 800, by skincare device 1500 including (comprising) smooth-plate 1501 in place of second-pad 857.

In some embodiments, skincare device 1500 may differ from skincare device 800, by skincare device 1500 being without one or both electrodes (such as, first-electrode 1001 and/or second-electrode 1003).

In some embodiments, smooth-plate 1501 may be associated with heating and/or cooling functions of a given skincare device, such as skincare device 1500. In some embodiments, internally within main-body 903 may be one or more heaters and/or coolers (e.g., heater/cooler 4709) that may be electrically powered. In some embodiments, the one or more heater/cooler 4709 may be operationally coupled to smooth-plate 1501, so as to transmit either raised temperatures through and to smooth-plate 1501; or to transmit cooled temperatures to smooth-plate 1501, wherein heating/cooling is with respect to the ambient environmental temperature (e.g., room temperature). In some embodiments, the one or more heaters and/or coolers may be one or more solid-state circuits. In some embodiments, the one or more heater/cooler 4709 may be one or more Peltier thermal circuits/devices. In some embodiments, the one or more heater/cooler 4709 may be one or more Peltier thermo electric module(s) (TEM). Depending upon direction of current through a Peltier circuit/device, the Peltier circuit/device may heat or cool. In some embodiments, a given smooth-plate 1501 may be operationally coupled to a plurality of heater/cooler 4709, such that different regions of the same smooth-plate 1501 may be heated and/or cooled differently at the same time.

In some embodiments, the outer exterior portion (that may be configured for human skin contact) of the second-pad may be smooth-plate 1501. In some embodiments, the plurality of electronic components of the given skincare device (e.g., 1500) may comprise at least one heater/cooler circuit 4709 that may be operatively linked to the at least one power-source (e.g., 4705) and to smooth-plate 1501 so as to heat or cool at least a region of smooth-plate 1501, such that smooth-plate 1501 heats or cools the region of human skin when smooth-plate 1501 is pressed against the region of human skin.

In some embodiments, at least some portion of smooth-plate 1501 may be made substantially of material(s) conductive for heat conduction. In some embodiments, at least some portion of smooth-plate 1501 may be made substantially of one or more metals.

In some embodiments, at least some exterior portion of smooth-plate 1501 may con-toured with a specific and predetermined shaped configured for rubbing human skin.

In some embodiments, at least some exterior portion of smooth-plate 1501 may have pointed edge, but so pointed as easily harm or puncture human skin. In some embodiments, such a pointed edge may facilitate reaching corners, nooks, and/or crannies of a given region of human skin, such as human skin of the face (e.g., around and under eyes, around the nose, around the ears, etc.).

In some embodiments, at least some exterior portion of smooth-plate 1501 may be substantially smooth and/or polished. In some embodiments, the at least some exterior portion of smooth-plate 1501 that may be substantially smooth and/or polished may be configured for removable physical contact with human skin, to impart heat and/or cooling to that region of human skin. In some embodiments, the at least some exterior portion of smooth-plate 1501 that may be substantially smooth and/or polished may be configured for rubbing and/or pushing against a region of human skin, to impart heat and/or cooling to that region of human skin. Heating the region of human skin may tend to open pores in that region of skin. Opening of skin pores may facilitate application of various skin products to that region of skin, such as, but not limited to, ointments, lotions, creams, serums, gels, medicines, pharmaceuticals, medicaments, soaps, surfactants, vitamins, supplements, herbs, plants, vegetables, meats, cleansers, cleaners, de-oilers, de-greasers, masks, makeup, treatments, combinations thereof, and/or like. Cooling the region of human skin may tend to close pores in that region of skin.

In some embodiments, the at least some exterior portion of smooth-plate 1501 may be used for a gentle press and roll massaging for better product absorption by the skin and/or for anti-aging massage and skin tightening.

In one embodiment of the present disclosure, the at least some exterior portion of smooth-plate 1501 may be heated using a heating mode option of the given skincare device 1500. Such heating may facilitate efficient product absorption into the skin (and tissue beneath) by melting skincare products and pushing them into skin pores and inner dermal layers of the skin. Further, the at least some exterior portion of smooth-plate 1501 that may be heated (or cooled) may be used for lymphatic massage and/or for facilitating lymphatic drainage, encouraging sinus clearage, and/or the like.

In another embodiment of the present disclosure, the at least some exterior portion of smooth-plate 1501 may be cooled down using a cooling mode option of the given skincare device 1500. The cooled and/or cold exterior surface(s) of smooth-plate 1501 may be used for one or more of the following: closing skin pores, shrinking skin pores, skin tightening, minimizing aging of skin, minimizing wrinkles, shrinking wrinkles, soothing skin, numbing skin, lymphatic massage, lymphatic drainage, combinations thereof, and/or the like.

As noted, skincare device 2200 is shown in figures FIG. 22 through and including FIG. 28. In some embodiments, skincare device 2200 may be substantially similar to skincare device 800, except skincare device 2200 may be without base 805. Or in the alternative, skincare device 2200 may be a skincare device 800 but shown without its base 805. In some embodiments, skincare device 2200 and skincare device 800/1500 may share a same overall shape of main-body 903 (e.g., compare FIG. 23 to FIG. 9). In some embodiments, skincare device 2200 and skincare device 800/1500 may share at least some components and/or some electronics. In some embodiments, skincare device 2200 and skincare device 800/1500 may share a same: first-major-side 803, first-pad 807, boundary 840, second-major-side 853, second-pad 857, main-body 903, top 911, bottom 919, first-electrode 1001, and/or second-electrode 1003. These components, parts, structures, and/or electronics for skincare device 2200 may be as substantially discussed above for skincare device 800/1500, aside from differences noted below.

Figure 23:
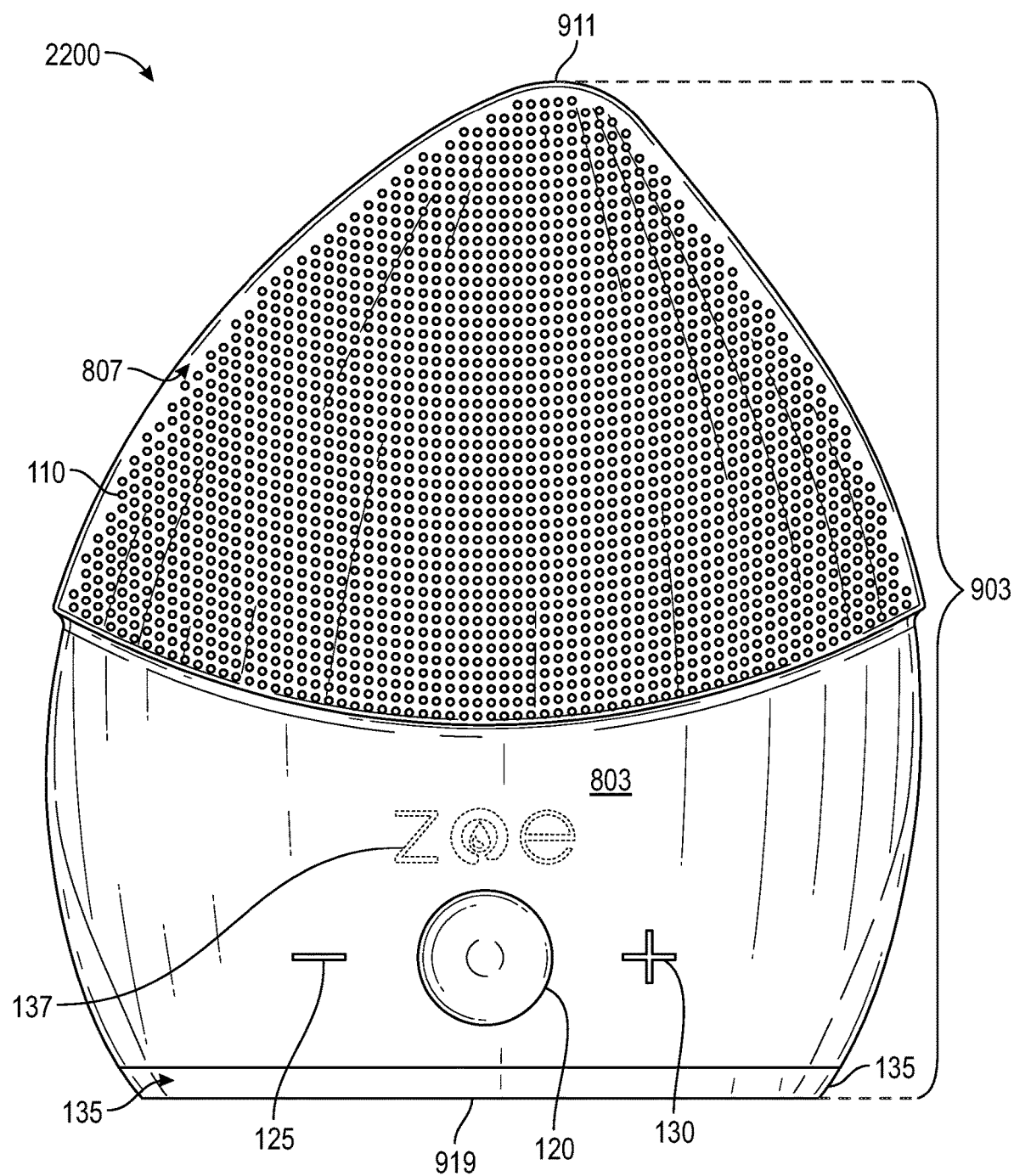
FIG. 23 depicts a front view of the fourth embodiment.
Figure 24:
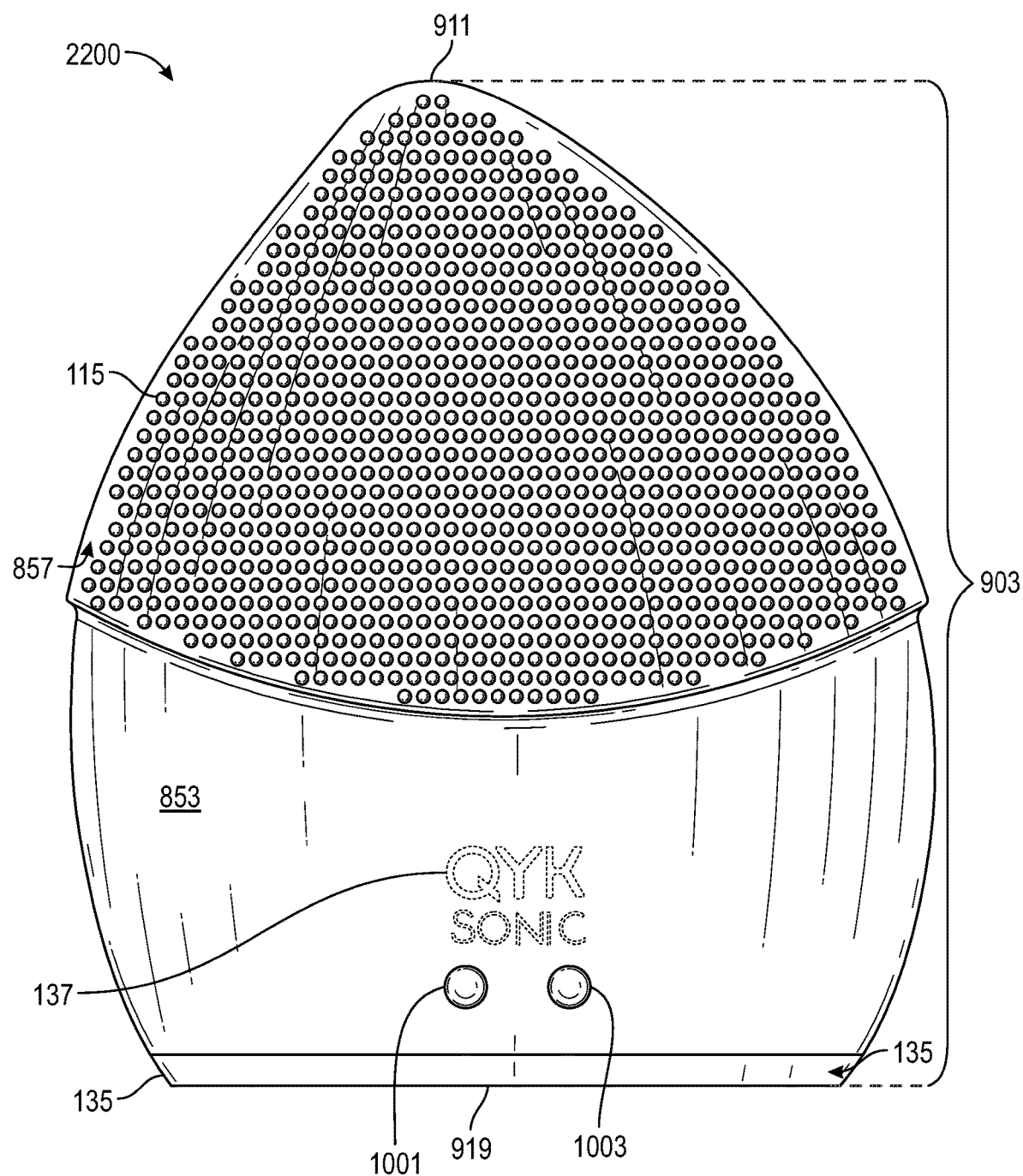
FIG. 24 depicts a back view of the fourth embodiment.
Figure 25:
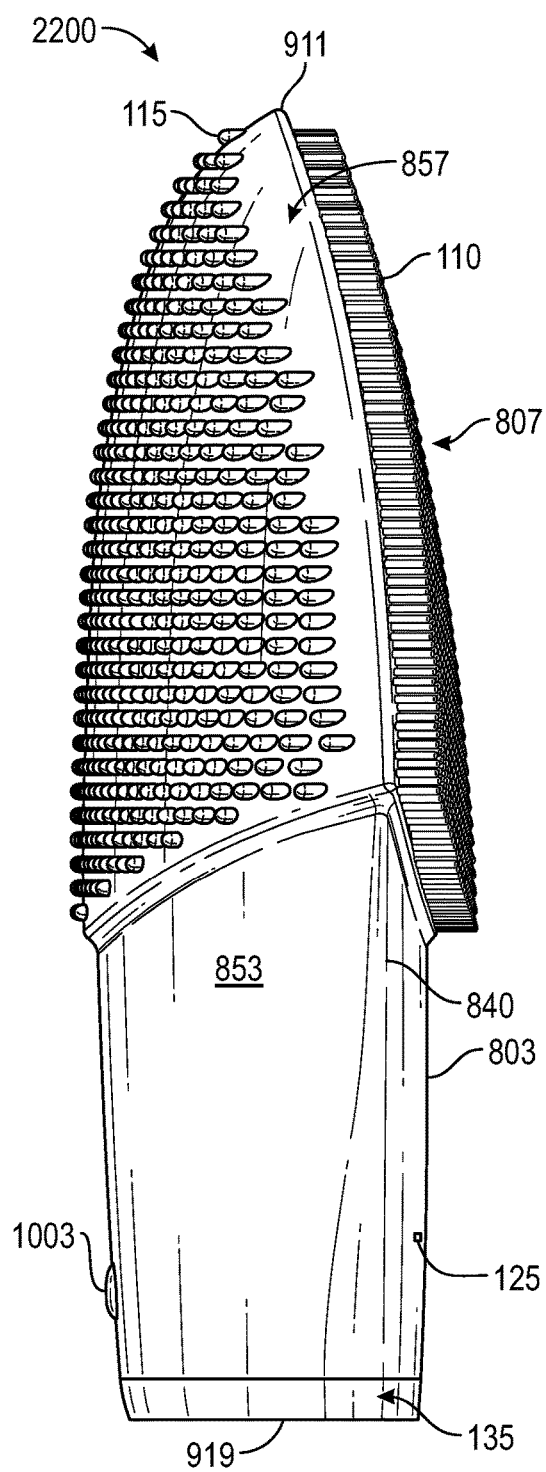
FIG. 25 depicts a left-side view of the fourth embodiment.
Figure 26:
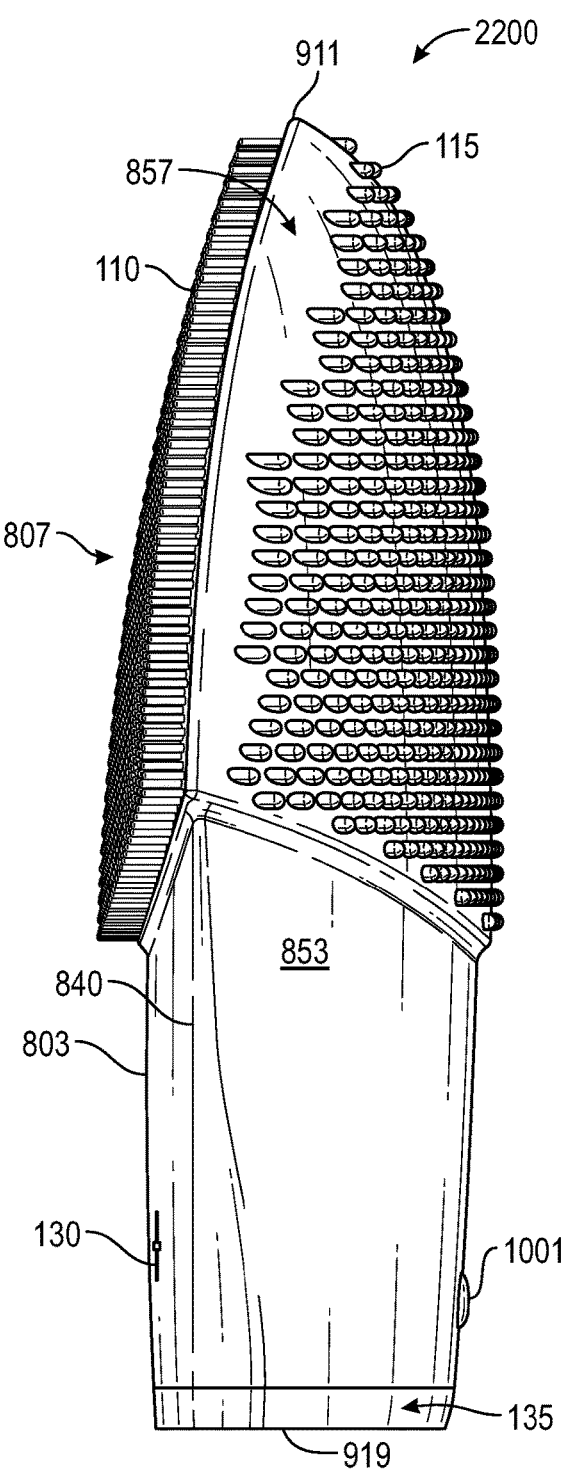
FIG. 26 depicts a right-side view of the fourth embodiment.
Figure 27:
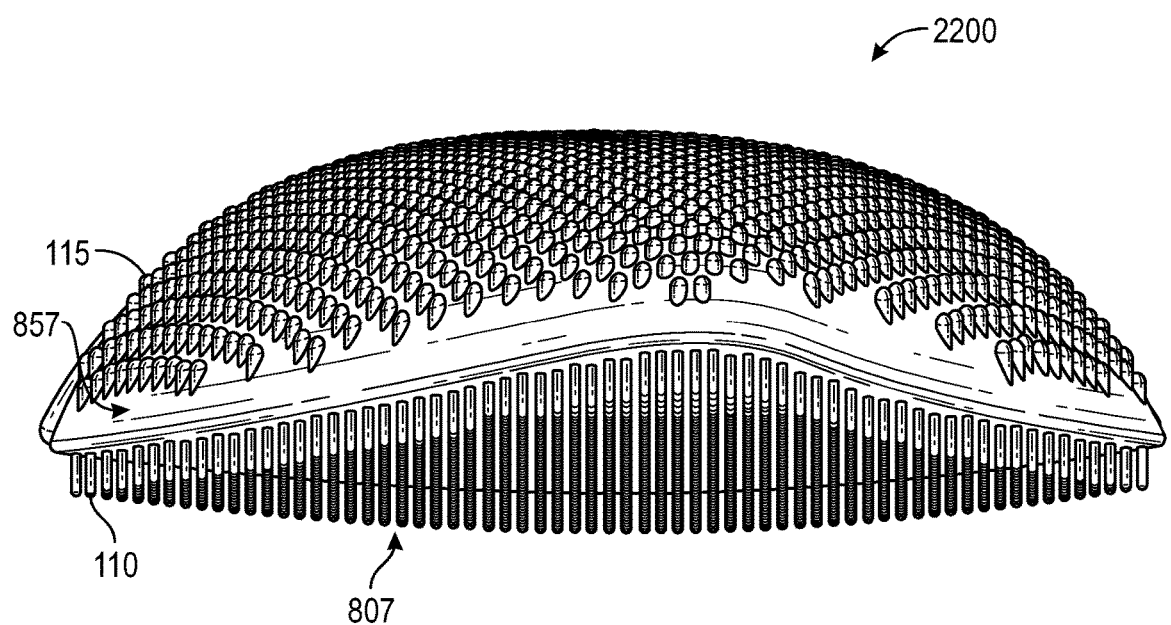
FIG. 27 depicts a top view of the fourth embodiment.

As shown in FIG. 23 and in FIG. 24, without base 805, main-body 903 of skincare device 2200 may have a bottom 919 that may be substantially flat and capable of being substantially parallel with a tabletop, a floor, a ground surface, and/or the like, that bottom 919 may be resting upon.

FIG. 28 may show a bottom view of skincare device 2200 without any base 805. In some embodiments, skincare device 2200 may comprise main-body 903. In some embodiments, main-body 903 may comprise bottom 919. In some embodiments, bottom 919 of skincare device 2200 may comprise a surface-of-bottom 2805. In some embodiments, surface-of-bottom 2805 may be a substantially flat surface. In some embodiments, surface-of-bottom 2805 may be a substantially smooth surface. In some embodiments, surface-of-bottom 2805 may be a substantially planar surface. In some embodiments, surface-of-bottom 2805 may be attached to main-body 903 by at least one fastener 2801. In some embodiments, fastener 2801 may be a mechanical fastener. In some embodiments, fastener 2801 may be one or more of: a screw, a bolt, a nail, a tack, a rivet, combinations thereof, and/or the like. In some embodiments, fastener 2801 may be chemical adhesive. In some embodiments, fastener 2801 may be a welded connection, e.g., via heat, ultrasound, and/or solvent bonding. In some embodiments, surface-of-bottom 2805 may comprise at least one connector 301 (connector 301 is discussed above).

In some embodiments, surface-of-bottom 2805 may comprise a means for removable attachment to a base 805. In some embodiments, this means for removable attachment may utilize magnetic attraction. In some embodiments, surface-of-bottom 2805 may comprise one or more magnets. In some embodiments, surface-of-bottom 2805 may comprise one or more materials that may removably attach to a magnet. In some embodiments, below (i.e., interior surface of) and/or inside of surface-of-bottom 2805 may be one or more magnets, wherein such one or more magnets may be proximate (near/close) to the exterior surface of surface-of-bottom 2805. In some embodiments, below (i.e., interior surface of) and/or inside of surface-of-bottom 2805 may be one or more materials that may removably attach to a magnet, wherein such one or more materials may be proximate (near/close) to the exterior surface of surface-of-bottom 2805. And a complimentary substantially flat surface of base 805 may comprise one or more magnets and/or materials that may be attracted to a magnet.

In some embodiments, skincare device 2200 may be without one or both electrodes (e.g., first-electrode 1001 and/or second-electrode 1003).

As noted, skincare device 2900 is shown in figures FIG. 29 through and including FIG. 35. In some embodiments, skincare device 2900 may be substantially similar to skincare device 1500, except skincare device 2900 may be without base 805. Or in the alternative, skincare device 2900 may be a skincare device 1500 but shown without its base 805. In some embodiments, skincare device 2900 and skincare device 1500 may share a same overall shape for main-body 903 (e.g., compare FIG. 30 to FIG. 16). In some embodiments, skincare device 2900 and skincare device 1500 may share at least some components and/or some electronics. In some embodiments, skincare device 2900 and skincare device 1500 may share a same: first-major-side 803, first-pad 807, boundary 840, second-major-side 853 (without second-pad 857), main-body 903, top 911, bottom 919, first-electrode 1001, second-electrode 1003, and/or smooth-plate 1501. These components, parts, structures, and/or electronics for skincare device 1500 may be as substantially discussed above for skincare device 800, aside from differences noted below.

Figure 30:
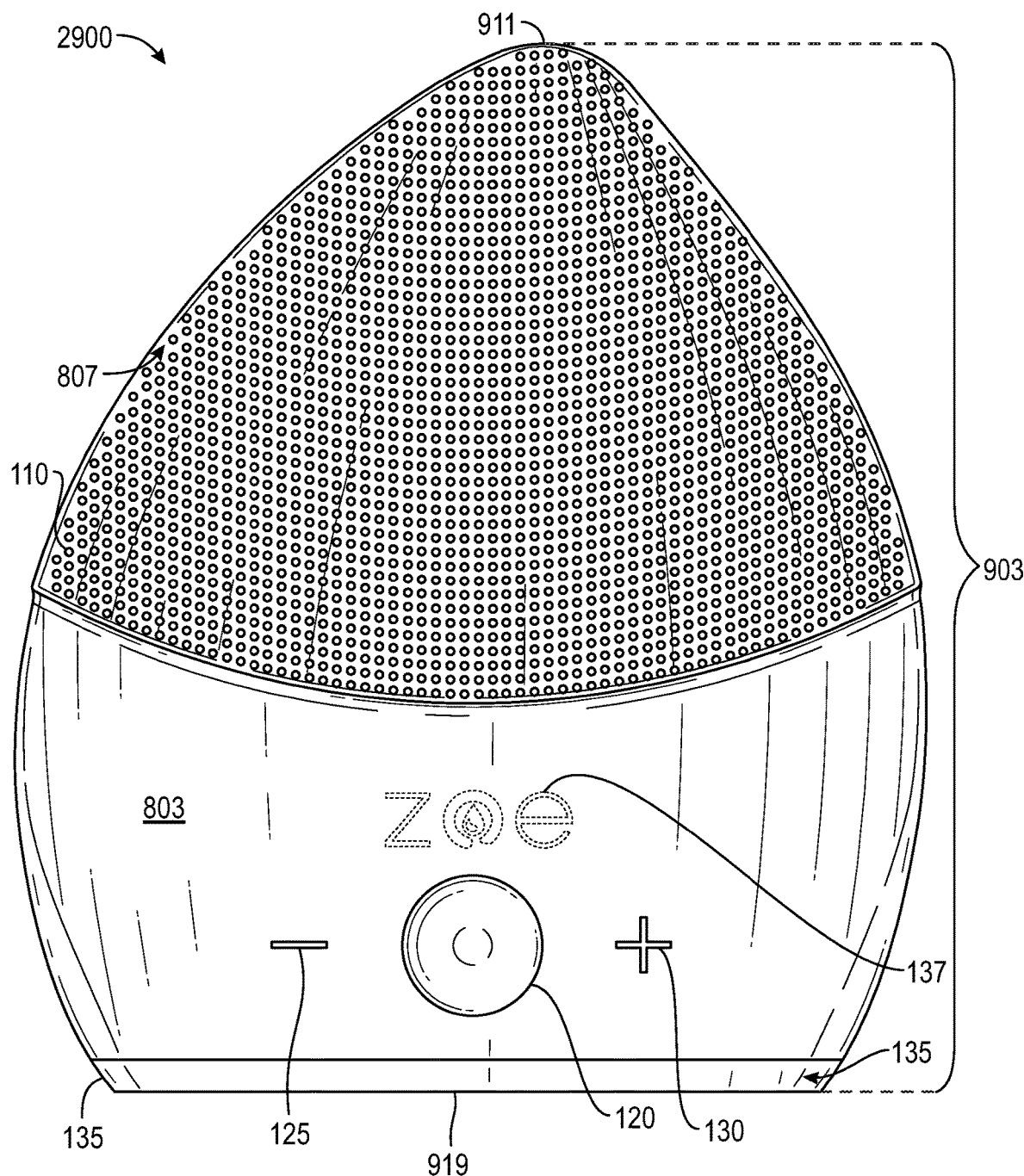
FIG. 30 depicts a front view of the fifth embodiment.
Figure 31:
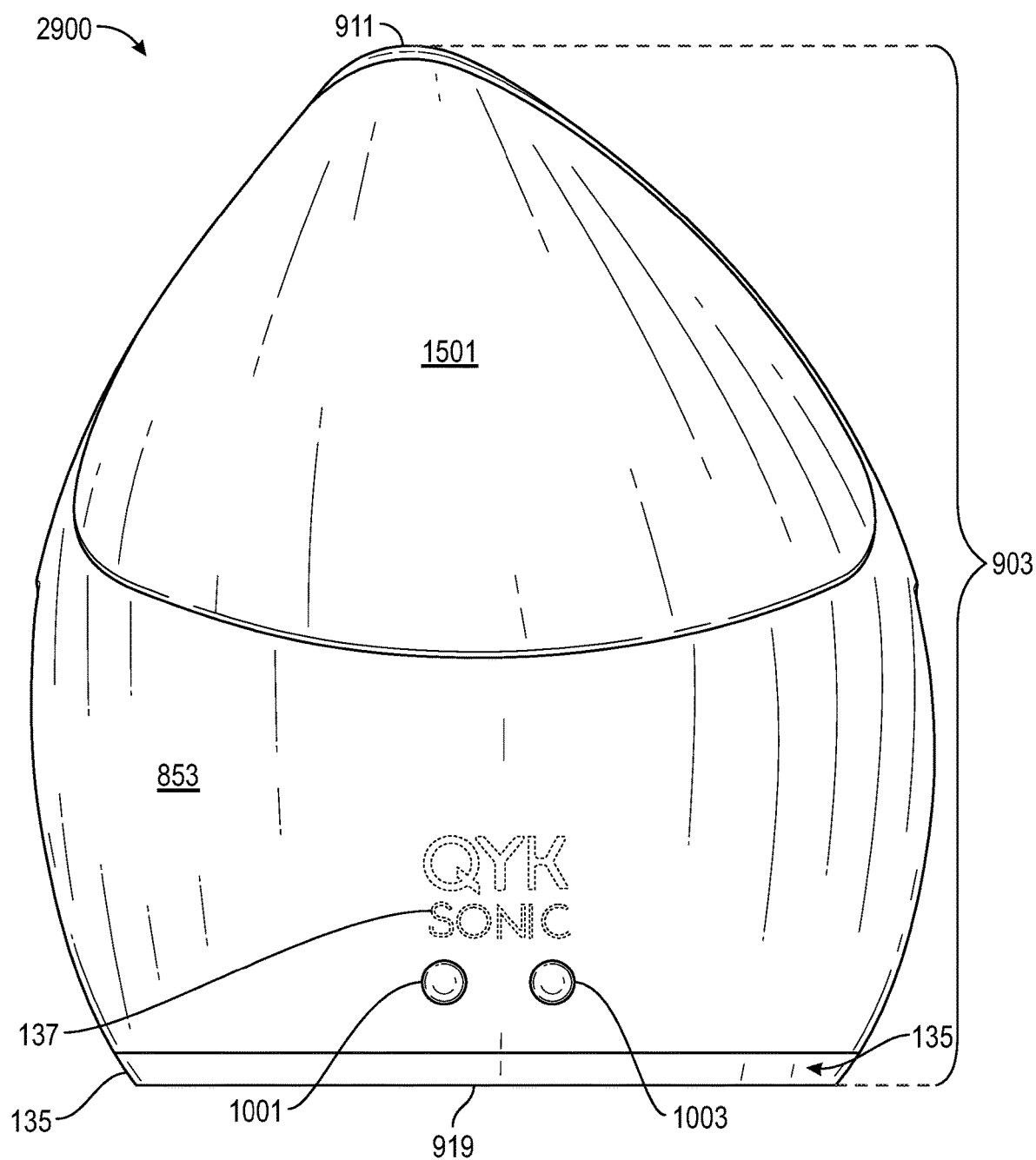
FIG. 31 depicts a back view of the fifth embodiment.
Figure 32:
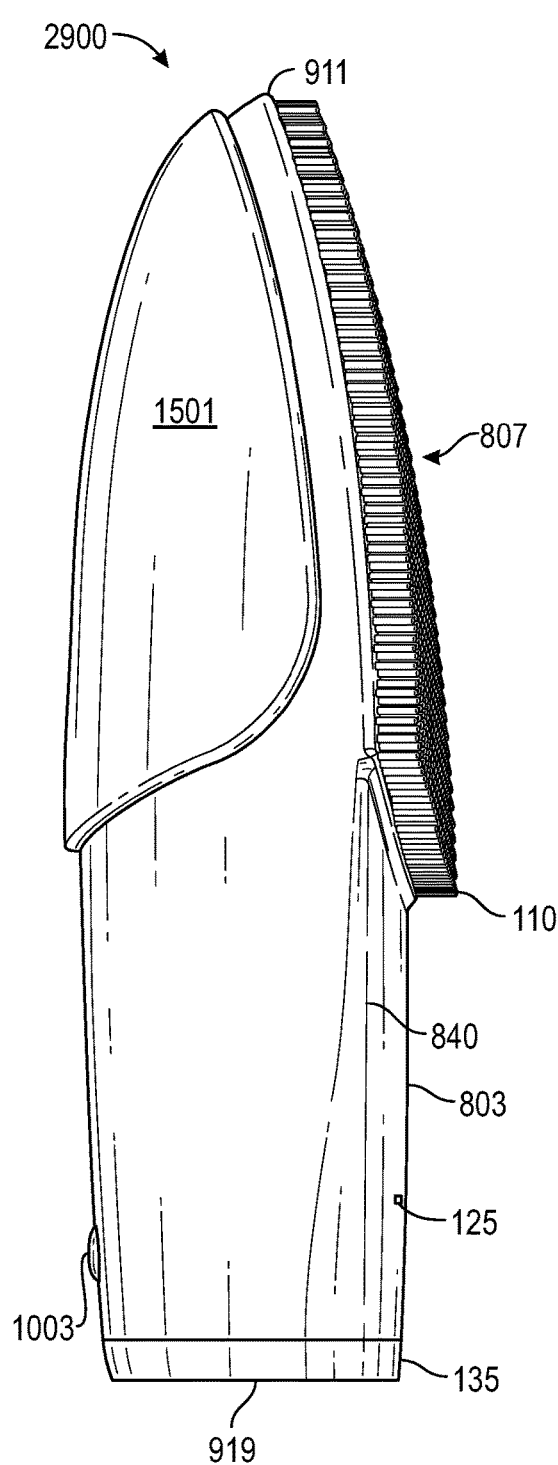
FIG. 32 depicts a left-side view of the fifth embodiment.
Figure 33:
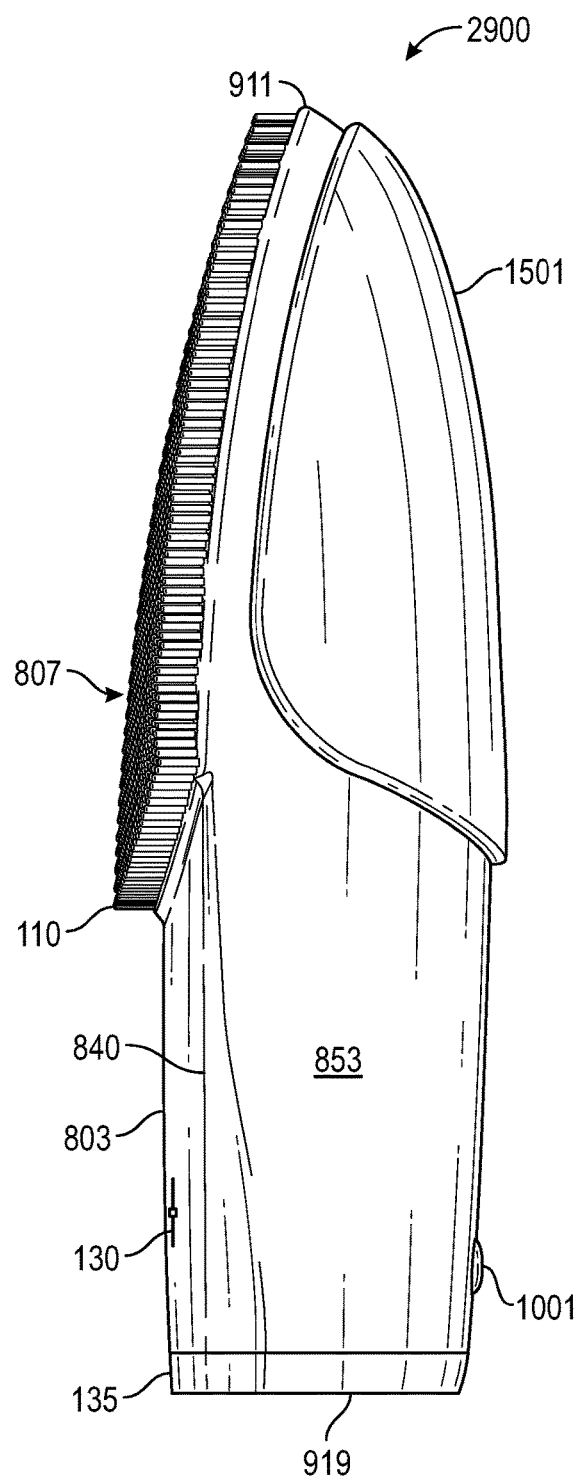
FIG. 33 depicts a right-side view of the fifth embodiment.
Figure 34:
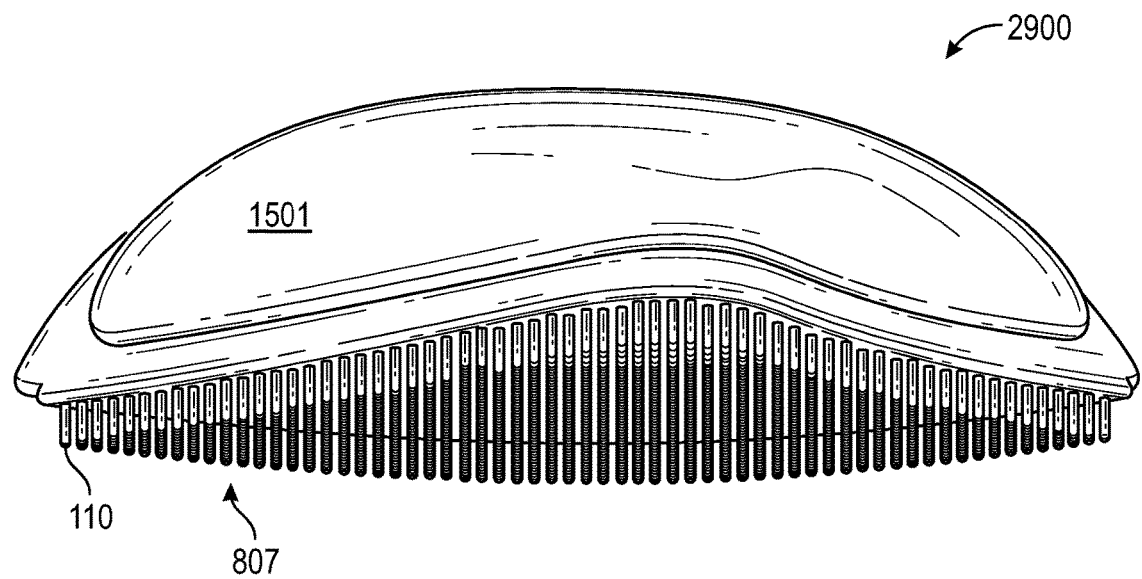
FIG. 34 depicts a top view of the fifth embodiment.

As shown in FIG. 30 and in FIG. 31, without base 805, main-body 903 of skincare device 2900 may have a bottom 919 that may be substantially flat and capable of being substantially parallel with a tabletop, a floor, a ground surface, and/or the like, that bottom 919 may be resting upon. In some embodiments, bottom 919 of skincare device 2900 may be as discussed above.

In some embodiments, skincare device 2900 may be without one or both electrodes (e.g., first-electrode 1001 and/or second-electrode 1003).

As noted, skincare device 3600 is shown in figures FIG. 36 through and including FIG. 42. In some embodiments, skincare device 3600 may be similar to skincare 800 (or to skincare device 2200), wherein skincare device 3600 may be shown without base 805 (or not have a base 805); however the pads (e.g., first-pad 3607 and/or second-pad 3657) of skincare device 3600 may be of different shapes from the pads (e.g., first-pad 807 and/or second-pad 857) of skincare device 800.

Figure 37:
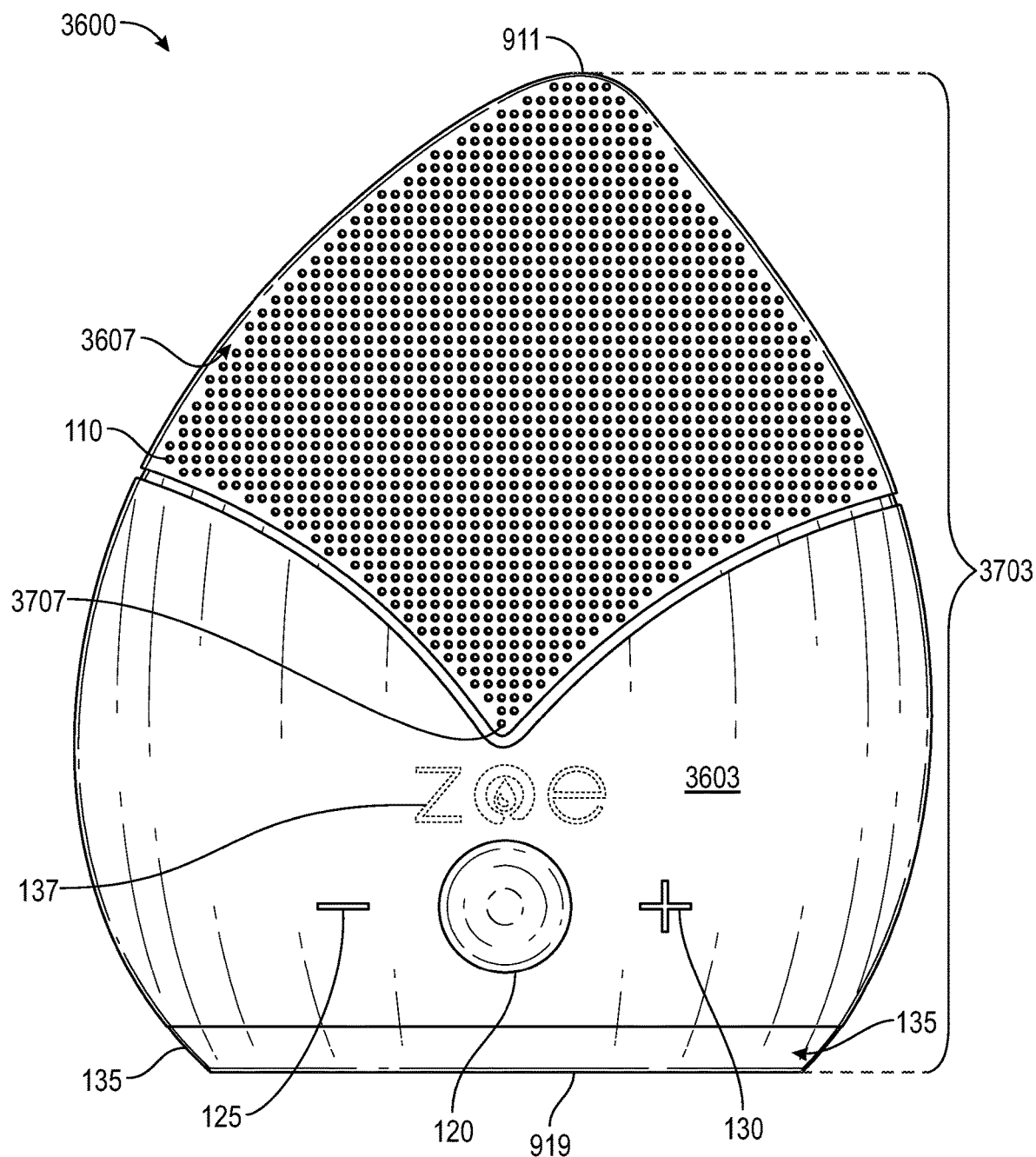
FIG. 37 depicts a front view of the sixth embodiment.

In some embodiments, skincare device 3600 may be comprised of a main-body 3703. See e.g., FIG. 37. In some embodiments, base 805 may be attached to bottom 919 of main-base 3703 and in such embodiments, skincare device 3600 may also comprise base 805.

Figure 38:
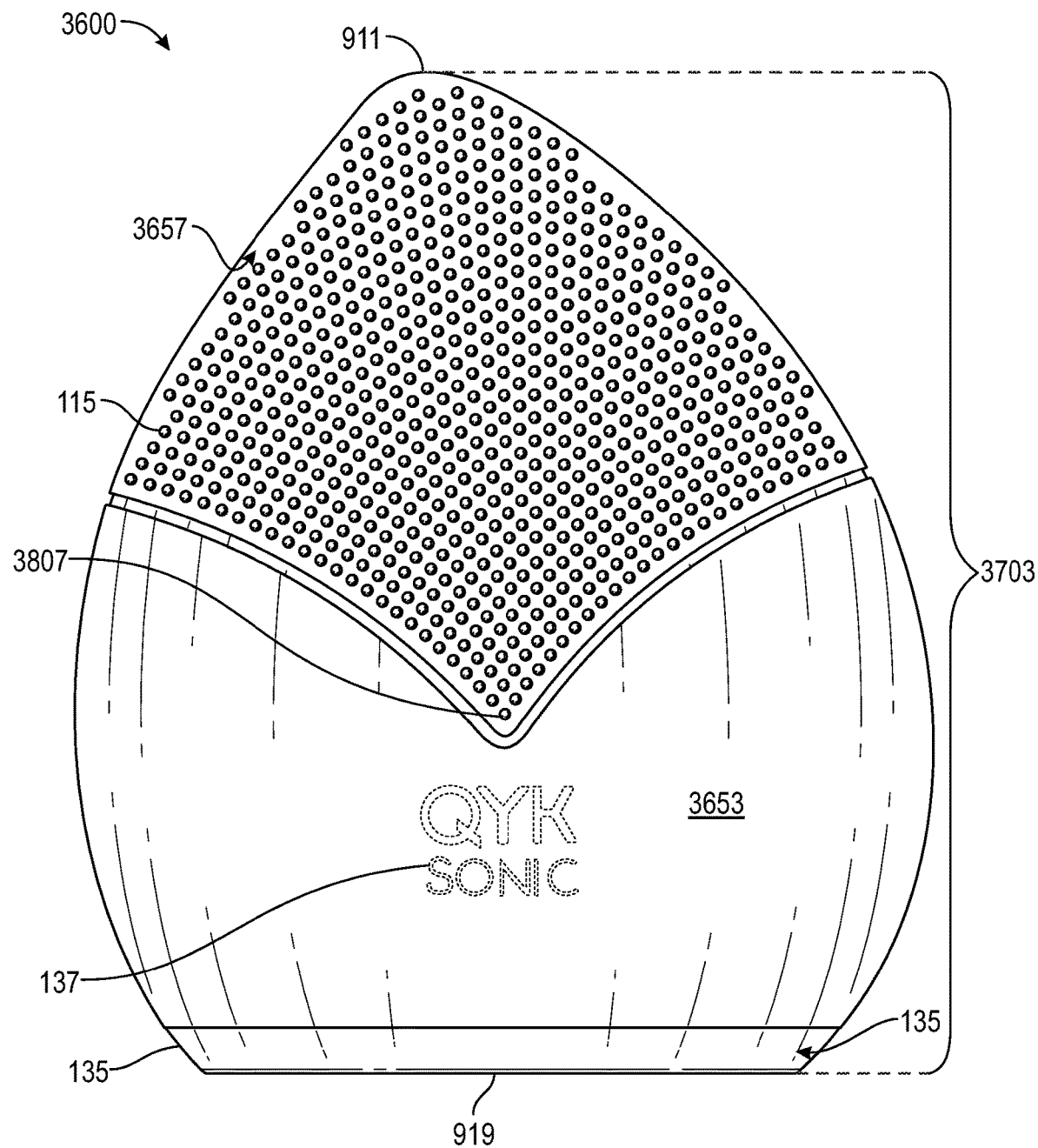
FIG. 38 depicts a back view of the sixth embodiment.
Figure 39:
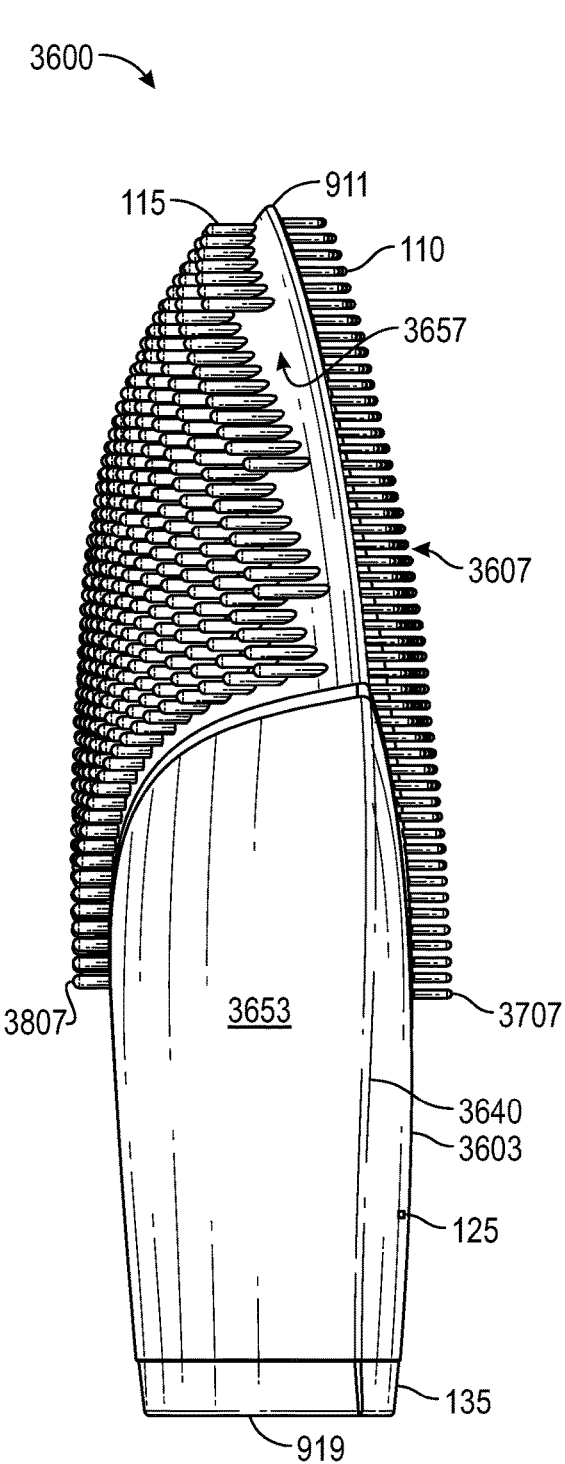
FIG. 39 depicts a left-side view of the sixth embodiment.
Figure 40:
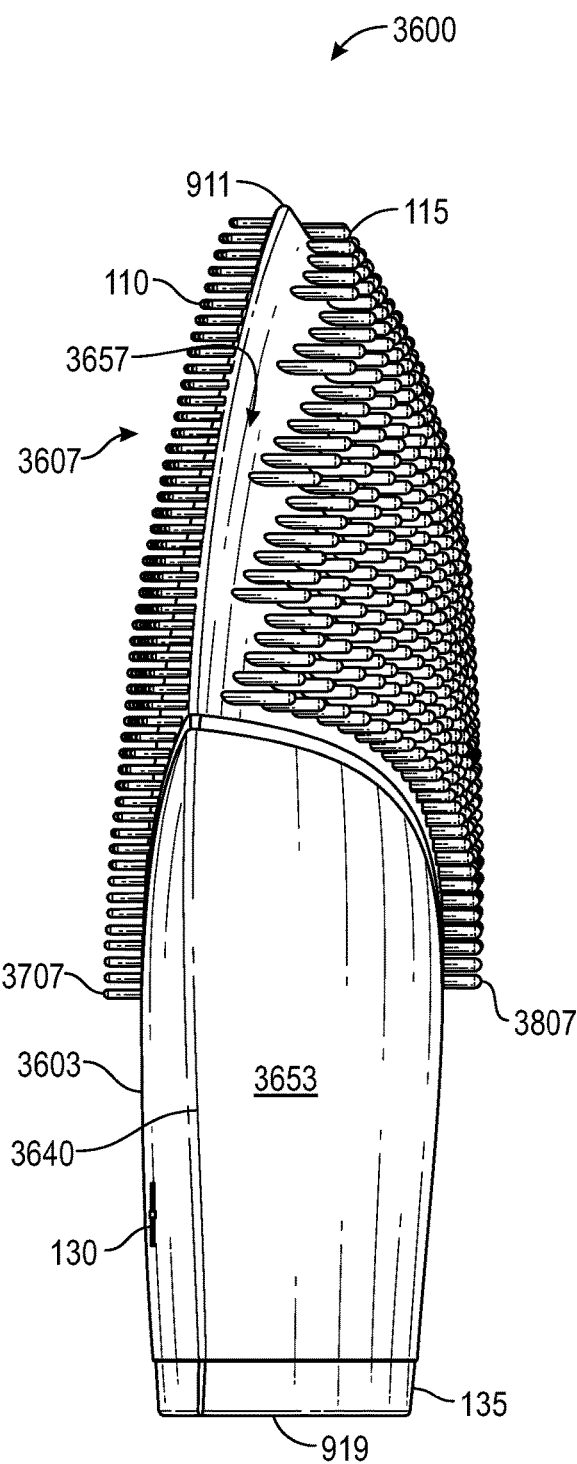
FIG. 40 depicts a right-side view of the sixth embodiment.
Figure 41:
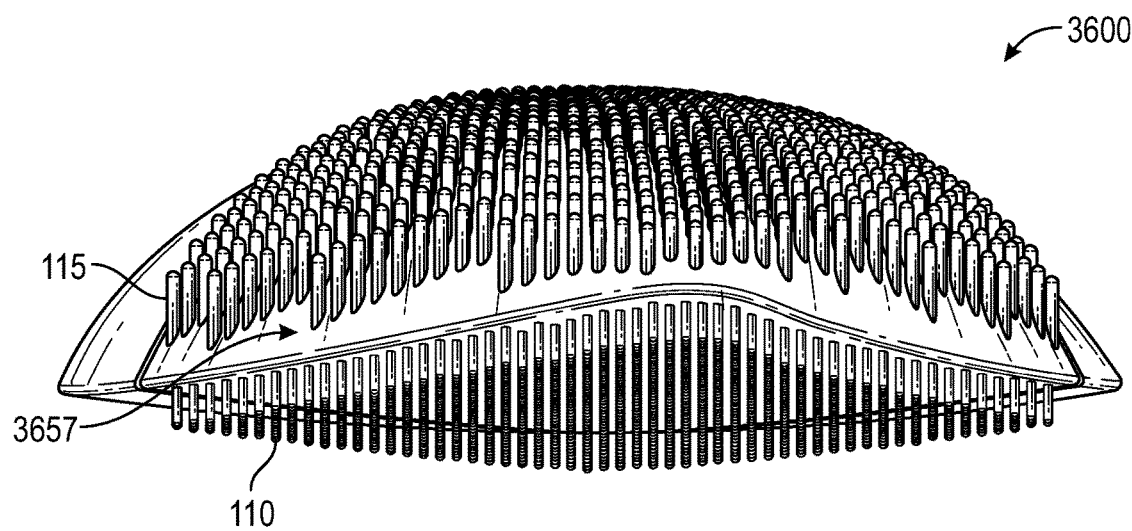
FIG. 41 depicts a top view of the sixth embodiment.

In some embodiments, main-body 3703 may be configured to be a portable (mobile) hand-held device. In some embodiments, main-body 3703 may be substantially similar to main-body 903 in terms of functionality, purpose, and/or benefits. In some embodiments, main-body 3703 may be configured to be held and used by one human hand. In some embodiments, main-body 3703 may be a three-dimensional (3D) device. From a front view (e.g., FIG. 37) and/or a back/rear view (e.g., FIG. 38), main-body 3703 may be substantially or generally shaped with curved sides, a top 911 point (wherein that point may be rounded) and a substantially flat bottom 919. In some embodiments, main-body 3703 may run from top 911 to (flat) bottom 919, see e.g., FIG. 37 and/or FIG. 38. In some embodiments, main-body 3703 may have a fixed and predetermined thickness (see e.g., FIG. 39 and/or FIG. 40) of about 0.5 inch to about 1.5 inches, plus or minus 0.1 inch.

Continuing discussing main-body 3703, in some embodiments, main-body 3703 may be comprised of two major and opposing sides, that of first-major-side 3603 and that of second-major-side 3653. See e.g., FIG. 36; and compare FIG. 37 to FIG. 38. In some embodiments, first-major-side 3603 may be attached to and/or in communication with second-major-side 3653 along peripheral boundary 3640. See e.g., FIG. 36. In some embodiments, first-major-side 3603 may be more flat (i.e., flatter) than second-major-side 3653. In some embodiments, second-major-side 3653 may be more curved than first-major-side 3603. See e.g., figures FIG. 39, FIG. 40, FIG. 41, and FIG. 42.

In some embodiments, first-major-side 3603 may be substantially similar to first-major-side 803 in terms of function, purpose, and/or benefit; but may differ in shape. In some embodiments, second-major-side 3653 may be substantially similar to second-major-side 853 in terms of function, purpose, and/or benefit; but may differ in shape. In some embodiments, boundary 3640 may be substantially similar to boundary 840 in terms of function, purpose, and/or benefit; but may differ in shape.

Continuing discussing first-major-side 3603 and second-major-side 3653, in some embodiments, disposed on a lower portion of first-major-side 3603 and/or of second-major-side 3653 may be one or more of: controls, connectors, electrodes, graphics, images, artwork, branding, trademarks, taglines, logos, combinations thereof, and/or the like. See e.g., FIG. 37 and FIG. 38. For example, and without limiting the scope of the present invention, first-major-side 3603 may comprise one or more of: control 120, control 125, control 130, graphic 137, combinations thereof, and/or the like. See e.g., FIG. 36 and FIG. 37. In alternative embodiments, second-major-side 3653 may comprise one or more of: control 120, control 125, control 130, graphic 137, combinations thereof, and/or the like.

In some embodiments, control 120, control 125, and/or control 130 may be located on: first-major-side 3603, second-major-side 3653, bottom 919, surface-of-bottom 2805, combinations thereof, and/or the like.

In some embodiments, connector 301 may be located on first-major-side 3603, second-major-side 3653, bottom 919, surface-of-bottom 2805, combinations thereof, and/or the like.

In some embodiments, graphics 137 may be one or more of: graphics, images, artwork, branding, trademarks, taglines, logos, language, wording, numbers, combinations thereof, and/or the like—on exterior surfaces of first-major-side 3603, of second-major-side 3653, and/or of surface-of-bottom 2805. See e.g., FIG. 36, FIG. 37, and FIG. 38.

Continuing discussing main-body 3703, in some embodiments, each major-surface may comprise a pad. In some embodiments, first-major-surface 3603 may comprise first-pad 3607. In some embodiments, second-major-surface 3653 may comprise second-pad 3657. In some embodiments, on an upper portion of first-major-surface 3603 may be first-pad 3607. In some embodiments, on an upper portion of second-major-surface 3653 may be second-pad 3657. In some embodiments, on an upper portion of main-body 3703 may be first-pad 3607 on a same side as first-major-side 3603; and disposed opposite on the other side of main-body 3703 on the same side as second-major-side 3653, may be second-pad 3657. In some embodiments, when viewed from a front view (FIG. 37) and/or when viewed from a rear/back view (FIG. 38), each pad (first-pad 3607 and second-pad 3657, respectively) may be substantially shaped as: a four side polygon (e.g., a diamond shape) with rounded corners and slightly curved sides; or the like; and with a plurality of protrusions, referred to as touch-points. In some embodiments, a plurality of touch-points 110 may protrude from first-pad 3607. In some embodiments, a plurality of touch-points 115 may protrude from second-pad 3657. In some embodiments, first-pad 3607 may have a bottom 3707 disposed opposite from top 911. In some embodiments, second-pad 3657 may have a bottom 3807 disposed opposite from top 911. See e.g., FIG. 36, FIG. 37, and FIG. 38.

In some embodiments, a given pad may only have one type of touch-point. For example, and without limiting the scope of the present invention, in some embodiments, first-pad 3607 may have a plurality of touch-points 110 protrusions; whereas, second-pad 3657 may have a plurality of touch-points 115 protrusions. See e.g., FIG. 36 through and including FIG. 42.

Each touch-point (110/115) protrusion may a substantially cylindrical member ending in a free-end (an unattached end) that may be rounded; and opposing that free-end may be attached to a given pad (e.g., first-pad 3607 and/or second-pad 3657).

In some embodiments, skincare device 3600 may comprise one or more indicators 135. In some embodiments, a given indicator 135 may be a light source and/or a region of skincare device 3600 configured to emit light. In some embodiments, light emitted by indicator 135 may indicate a status and/or a change in status of skincare device 3600 or portion thereof. In some embodiments, indicator 135 may be located on an exterior of skincare device 3600. In some embodiments, indicator 135 may be located on an exterior of main-body 3703. In some embodiments, indicator 135 may be component(s) of main-body 3703. In some embodiments, indicator 135 may be located on an exterior of base 805. In some embodiments, indicator 135 may be component(s) of base 805. In some embodiments, indicator 135 may be located on an exterior of first-major-side 3603. In some embodiments, indicator 135 may be located on an exterior of second-major-side 3653. In some embodiments, indicator 135 may be a continuous band that may circumscribe an exterior of main-body 3703, base 805, combinations thereof, and/or the like. See e.g., FIG. 36 through and including FIG. 42.

In some embodiments, skincare device 3600 may comprise one or more electrodes, such as, first-electrode 1001 and/or second-electrode 1003. In some embodiments, first-electrode 1001 and/or second-electrode 1003 may be located on an exterior surface of main-body 3703. In some embodiments, first-electrode 1001 and/or second-electrode 1003 may be located on first-major-side 3603, second-major-side 3653, and/or surface-of-bottom 2805.

Figure 43:
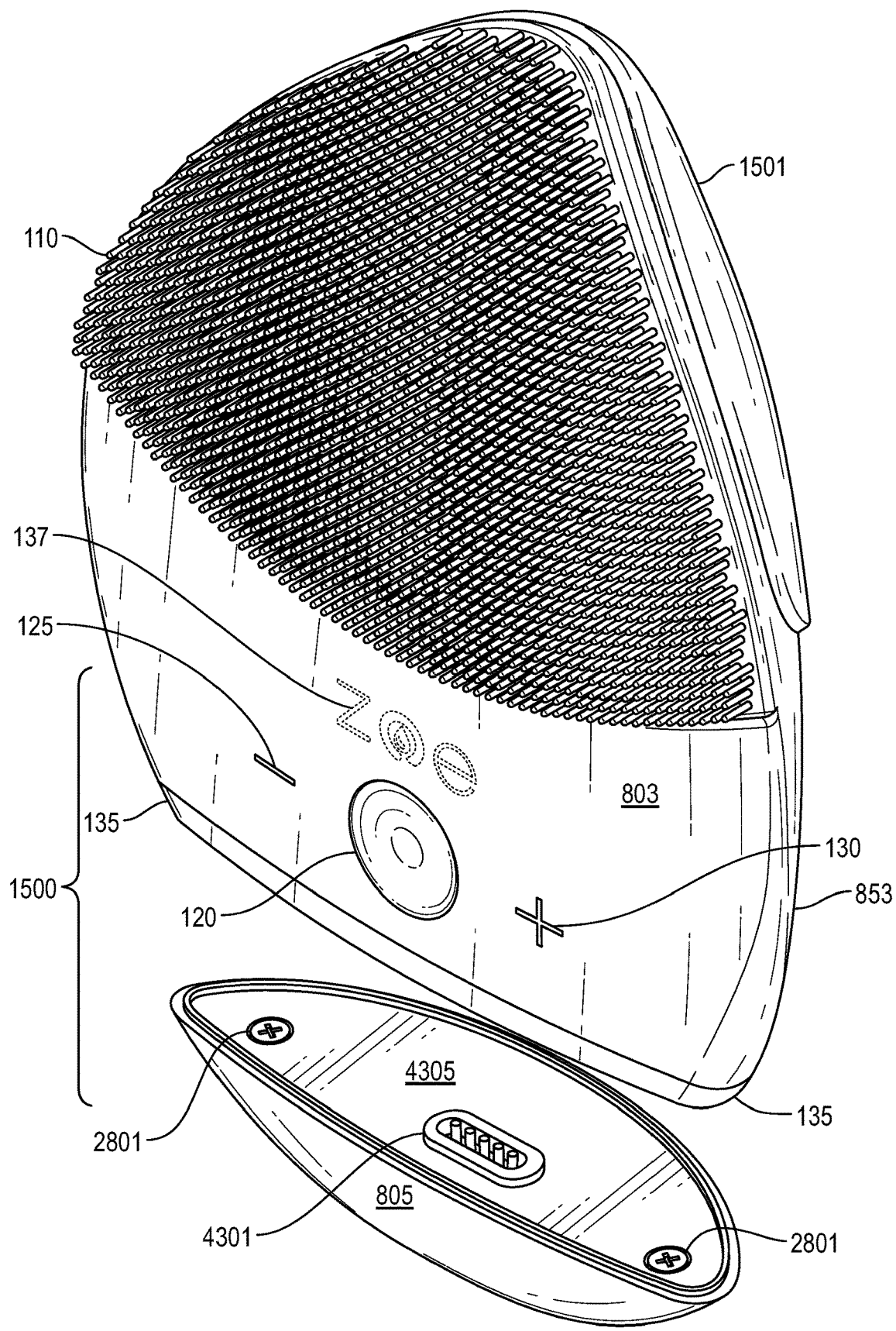
FIG. 43 depicts a portable, handheld, electronic skincare device showing its base removably detached from its main-body.
Figure 46:
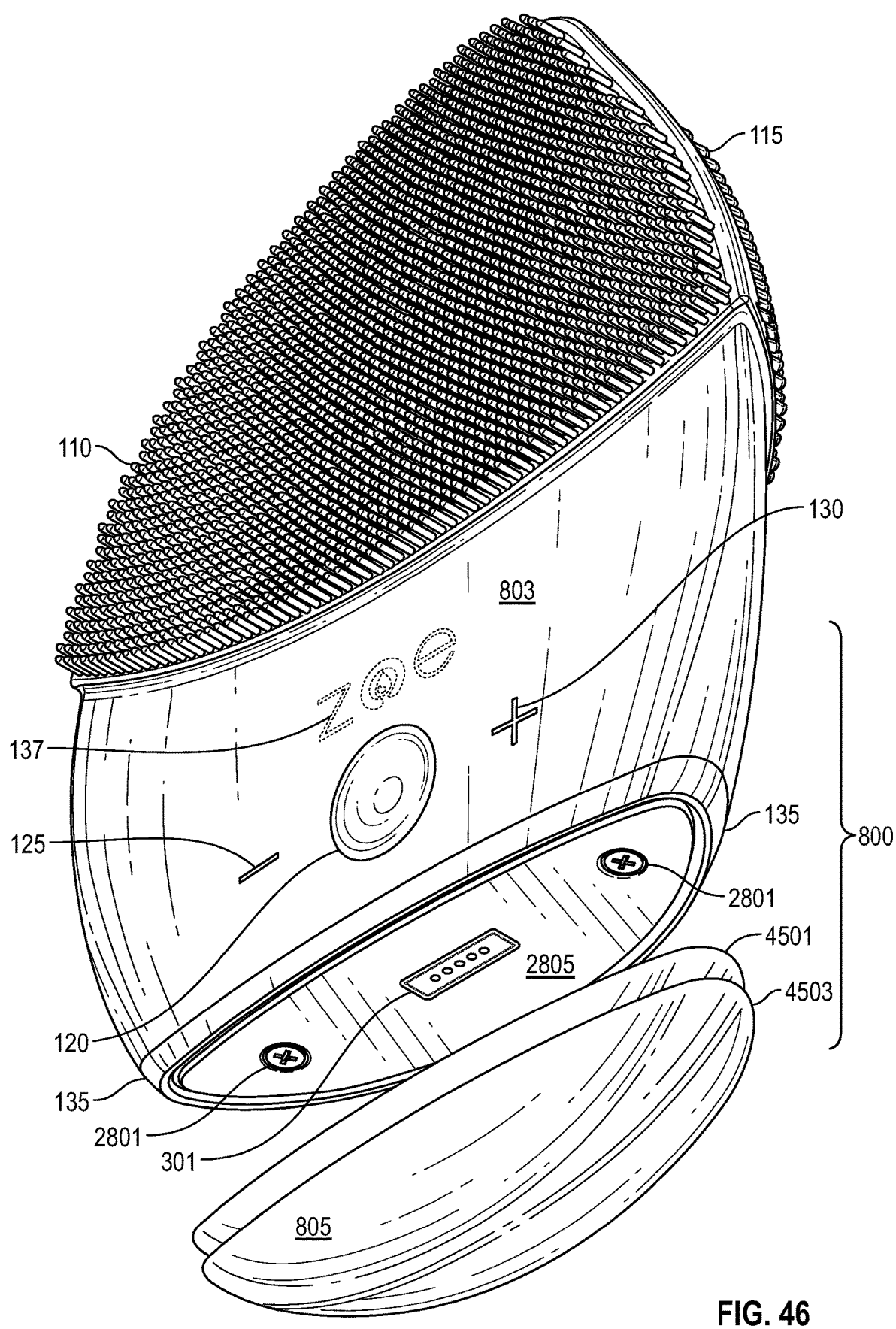
FIG. 46 depicts the portable, handheld, electronic skincare device of FIG. 45, showing its base removably detached from its main-body.

Figures FIG. 43 through and including FIG. 46 may show how a given base (e.g., base 805) may be removably attached to a bottom of a given main-body (e.g., main-body 903) of a given skincare device.

Figure 44:
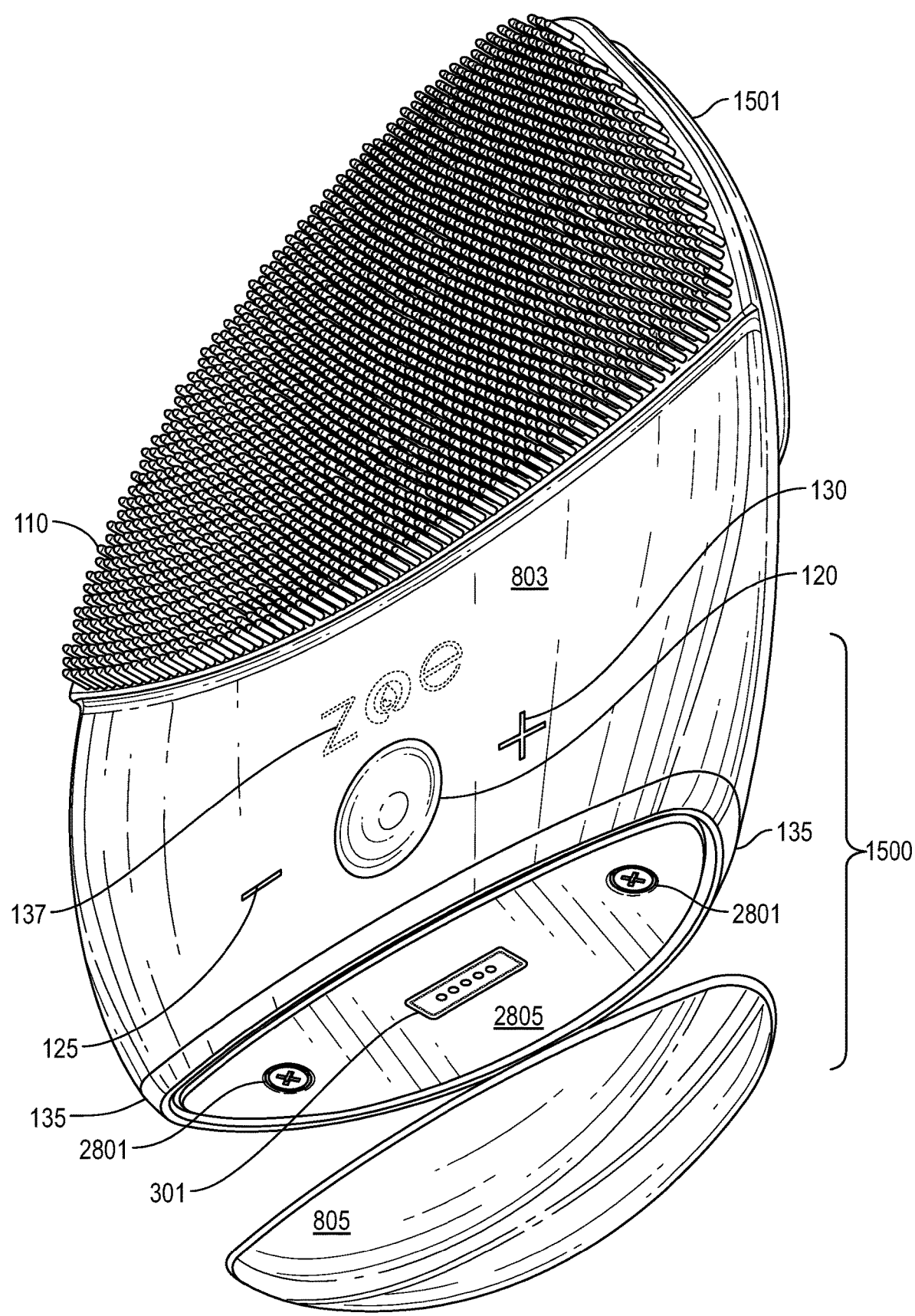
FIG. 44 depicts the portable, handheld, electronic skincare device of FIG. 43, showing its base removably detached from its main-body.

Figures FIG. 43 and FIG. 44 may depict skincare device 1500 shown with its base 805 removably detached from its main-body 903. Figures FIG. 43 and FIG. 44 may be from approximately opposing views. FIG. 43 may be from a top front perspective view. FIG. 44 may be from a bottom front perspective view.

Figure 45:
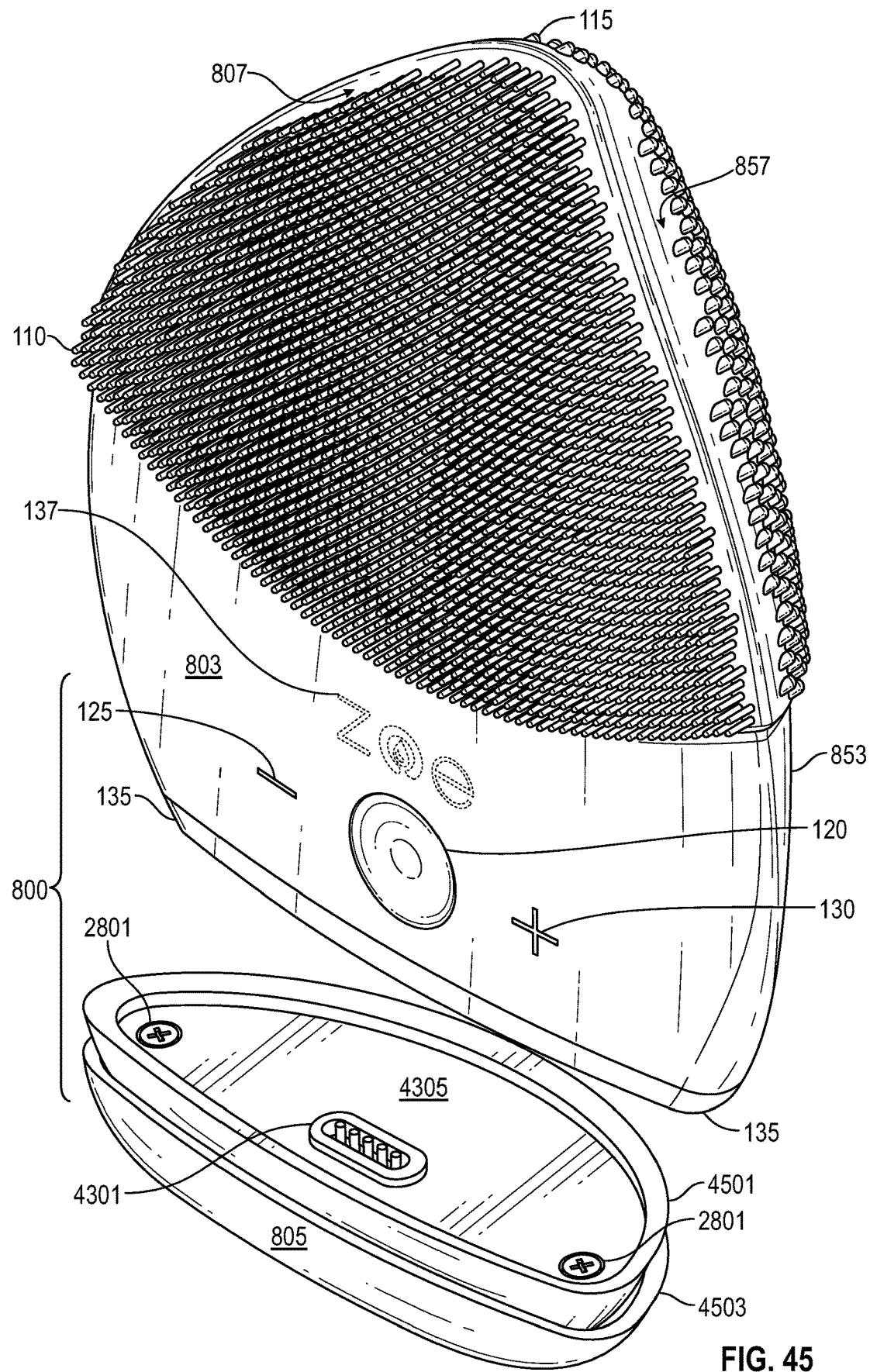
FIG. 45 depicts a portable, handheld, electronic skincare device showing its base removably detached from its main-body.

Figures FIG. 45 and FIG. 46 may depict skincare device 800 shown with its base 805 removably detached from its main-body 903. Figures FIG. 45 and FIG. 46 may be from approximately opposing views. FIG. 45 may be from a top front perspective view. FIG. 46 may be from a bottom front perspective view.

Both FIG. 43 and FIG. 45 may show a top-surface 4305 of base 805. In some embodiments, top-surface 4305 may be one or more of: substantially flat, substantially planar, substantially smooth, substantially rigid/firm, combinations thereof, and/or the like. Whereas, both FIG. 44 and FIG. 46 may show surface-of-bottom 2805 of main-body 903. In some embodiments, when base 805 may be removably attached to bottom 919 of main-body 903 (see e.g., FIG. 16 or FIG. 9), top-surface 4305 and surface-of-bottom 2805 may be substantially parallel with each other. In some embodiments, when base 805 may be removably attached to bottom 919 of main-body 903 (see e.g., FIG. 16 or FIG. 9), top-surface 4305 and surface-of-bottom 2805 may be at least partially touching each other. In some embodiments, when base 805 may be removably attached to bottom 919 of main-body 903 (see e.g., FIG. 16 or FIG. 9), top-surface 4305 and surface-of-bottom 2805 may be close and proximate to each other, closer than as shown in FIG. 43 through and including FIG. 46. In some embodiments, when base 805 may be removably attached to bottom 919 of main-body 903 (see e.g., FIG. 16 or FIG. 9), top-surface 4305 and surface-of-bottom 2805 may be at least a predetermined and fixed (static) distance from each other, that be closer than as shown in FIG. 43 through and including FIG. 46. In some embodiments, when base 805 may be removably attached to bottom 919 of main-body 903 (see e.g., FIG. 16 or FIG. 9), top-surface 4305 may be located immediately below surface-of-bottom 2805.

In some embodiments, base 805 may be removably attached to bottom 919 of main-body 903 by magnetic attraction. In some embodiments, base 805 may be removably attached to bottom 919 of main-body 903 by top-surface 4305 comprising at least one magnet and surface-of-bottom 2805 comprising at least one magnetically attractable materials. In some embodiments, base 805 may be removably attached to bottom 919 of main-body 903 by top-surface 4305 comprising at least one magnetically attractable materials and surface-of-bottom 2805 comprising at least one magnet. In some embodiments, base 805 may be removably attached to bottom 919 of main-body 903 by top-surface 4305 comprising at least one magnet and surface-of-bottom 2805 comprising at least one magnet.

Continuing discussing FIG. 43 through and including FIG. 46, in some embodiments, top-surface 4305 may comprise at least one connector 4301. In some embodiments, connector 4301 may be configured to removably couple with connector 301. In some embodiments, when base 805 may be removably attached to bottom 919 of main-body 903 connector 4301 may be removably coupled to connector 301 of surface-of-bottom 2805. In some embodiments, connector 301 and connector 4301 may be complimentary to each other. In some embodiments, when connector 301 may be removably coupled to connector 4301, controller 4701 may control various electronics of base 805, such as, but not limited to, motor 4707, heater/cooler 4709, sensor 4711, input/output (I/O) means 4715, electrodes—all of base 805. In some embodiments, when connector 301 may be removably coupled to connector 4301, power-source 4705 may power various electronics of base 805, such as, but not limited to, motor 4707, heater/cooler 4709, sensor 4711, input/output (I/O) means 4715, electrodes—all of base 805. In some embodiments, base 805 may comprise a power-source 4705, and when connector 301 may be removably coupled to connector 4301, power-source 4705 may power various electronics of main-body 903 (and of base 805), such as, but not limited to, controller 4701, memory 4703, motor 4707, heater/cooler 4709, sensor 4711, input/output (I/O) means 4715, communication module 4713, first-electrode 1001, second-electrode 1003, electrodes—all of main-body 903.

In some embodiments, top-surface 4305 may comprise one or more fasteners 2801 to secure top-surface 4305 to a remainder of base 805. See e.g., FIG. 43 and FIG. 45.

Note, base 805 shown in FIG. 45 and FIG. 46 may be a modified base 805 not elsewhere shown in the drawings. In some embodiments, base 805 may comprise two components, upper-base-portion 4501 and lower-base-portion 4503. In some embodiments, upper-base-portion 4501 and lower-base-portion 4503 may be attached to each other. In some embodiments, top-surface 4305 (with connector 4301) may be located on upper-base-portion 4501. In some embodiments, when upper-base-portion 4501 and lower-base-portion 4503 may be attached to each other, lower-base-portion 4503 may move, flex, bend, pulsate, vibrate, combinations thereof, and/or the like with respect to upper-base-portion 4501. In some embodiments, at least one motor 4707 may be housed within upper-base-portion 4501. In some embodiments, when motor 4707 of upper-base-portion 4501 may be active, pulsations/vibrations generated from motor 4707 may be transmitted to lower-base-portion 4503, such that lower-base-portion 4503 pulsates/vibrates.

Figure 47:
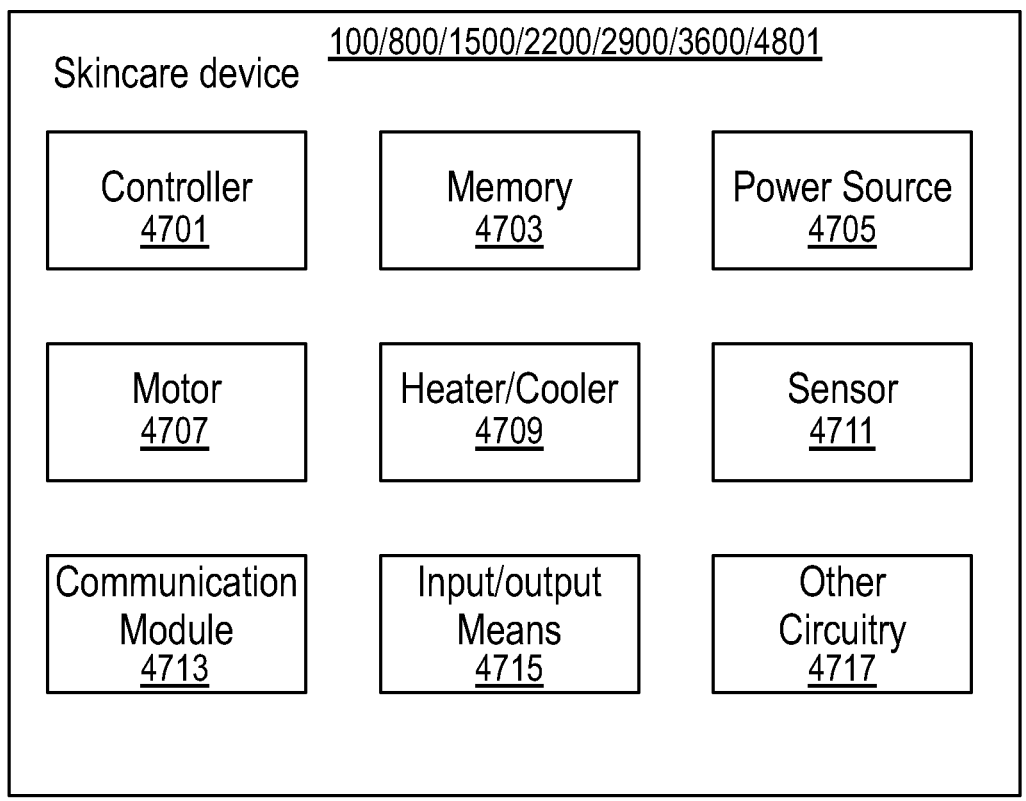
FIG. 47 depicts a block diagram showing at least some possible electronics of a given portable, handheld, electronic skincare device.

FIG. 47 may be a block diagram showing various electronics of a given skincare device 100/800/1500/2200/2900/3600 in accordance with embodiments of the present disclosure. In some embodiments, the given skincare device 100/800/1500/2200/2900/3600 may comprise one or more of: at least one microcontroller 4701, at least one memory (module) 4703, at least one power-source (e.g., battery unit) 4705, at least one motor (module) 4707, at least one communication module 4713, at least one input/output (I/O) means 4715, other electronic circuitry 4717, combinations thereof, and/or the like. In some embodiments, the given skincare device 100/800/1500/2200/2900/3600 may comprise one or more of: at least one microcontroller 4701, at least one memory 4703, at least one power-source 4705, at least one motor 4707, at least one heater/cooler 4709, at least one sensor 4711, at least one communication module 4713, at least one input/output (I/O) means 4715, other electronic circuitry 4717, combinations thereof, and/or the like. Not all skincare devices may comprise a heater/cooler 4709. Not all skincare devices may comprise a sensor 4711.

Continuing discussing FIG. 47, in some embodiments, microcontroller 4701 may be in (electrical and/or optical) communication with the memory (module) 4703. In some embodiments, microcontroller 4701 may be one or more processors for processing and/or following instructions, code, programming, firmware, and/or software that may be non-transitorily stored in memory 4703. In some embodiments, microcontroller 4701 may be comprised of such one or more processors. In some embodiments, microcontroller 4701 may be on and/or part of one or more printed circuit boards (PCBs). In some embodiments, microcontroller 4701 may control electronic function and/or overall operations of the given skincare device 100/800/1500/2200/2900/3600. In some embodiments, microcontroller 4701 may be located in main-body 203/903/3703 and/or in base 105/805.

Continuing discussing FIG. 47, in some embodiments, memory 4703 may be comprised of volatile and/or non-volatile memory devices for storing information and one or more set of instructions to be executed by the microcontroller 4701 and for storing temporary variables or other intermediate information during processing. The one or more set of instructions when executed by microcontroller 4701 may perform various tasks such as controlling motor(s) 4707, heater/cooler 4709, sensor(s) 4711, communication module(s) 4713, input/output means 4715, other electronic circuitry 4717, combinations thereof, and/or the like. In some embodiments, memory 4703 may be located in main-body 203/903/3703 and/or in base 105/805.

Continuing discussing FIG. 47, in some embodiments, the at least one power-source 4705 may comprises one or more batteries that may power various electronics and/or components of the given skincare device 100/800/1500/2200/2900/3600. In some embodiments, such one or more batteries may be rechargeable. In one embodiment, power-source 4705 may comprise one or more lithium ion (Li-ion) batteries, nickel-metal-hydride (NiMH) batteries, batteries with/of graphene, equivalent battery types, combinations thereof, and/or the like. In one embodiment, power-source 4705 may comprise one or more batteries which are typically used for electrically powering portable (mobile) electronic devices. In some embodiments, power-source 4705 may receive electrical power through an energized charging cable that may be removably attached to connector 301, wherein connector 301 may be in electrical communication with power-source 4705. In some embodiments, power-source

4705 may be located in main-body 203/903/3703, in base 105/805, combinations thereof, and/or the like.

Continuing discussing FIG. 47, in some embodiments, motor (module) 4707 may comprise one or more oscillating/vibratory motors. In some embodiments, one or more motor(s) 4707, when energized, may create pulsations and/or vibrations that may pulsate/vibrate the touch-points (e.g., 110 or 115 or both). In some embodiments, such pulsating/vibrating touch-points may then be used to communicate/transmit such pulsations/vibrations to regions of human skin that are in physical contact with the touch-points. Such energy and physical contact to the human skin may facilitate cleansing of that region of human skin. Such energy and physical contact to the human skin may facilitate loosening undesired elements from that region of human skin, including the skin pores, such as, but not limited to, contaminants, dead skin cells, bacteria, oil, grease, dirt, grime, makeup, cosmetics, creams, combinations thereof, and/or the like. Such energy and physical contact to the human skin may massage that region of the human skin.

In some embodiments, the given skincare device 100/800/1500/2200/2900/3600 may comprise at least two motors 4707. In some embodiments, each pad (e.g., 107/157/807/857/3607/3657) may have its own motor 4707. In some embodiments, each plurality of touch-points (e.g., 110/115) may have its own motor 4707. In some embodiments, each base (e.g., 105/805) may have its own motor 4707. In some embodiments, the given skincare device 100/800/1500/2200/2900/3600 may comprise at least three motors 4707. In some embodiments, the user may activate only one motor 4707 at a given time using in-put/output (I/O) means 4715 (such as by interacting with control(s) 120/125/130). In some embodiments, the user may activate both or all motors 4707 at a given time using input/output (I/O) means 4715 (such as by interacting with control(s) 120/125/130). In some embodiments, activation of a given motor 4707 may also be done through a separate computing-device 4803 (e.g., a smartphone, tablet computer, laptop, or the like) that may be in wireless communication with the given skincare device 100/800/1500/2200/2900/3600 via communication module 4713. See e.g., FIG. 47 and FIG. 48.

In some embodiments, each motor 4707 may vary from another motor 4707 in output characteristics such as, but not limited to, frequency, intensity, duration, combinations thereof, and/or the like. In some embodiments, operation of such motor(s) 4707 may be controlled by microcontroller 4701, and motor(s) 4707 may be powered by power-source 4705. In some embodiments, the user may increase or decrease the frequency of vibrations, the intensity of vibrations, and/or the duration of vibrations by using input/output (I/O) means 4715 (such as by using control(s) 120/125/130) for various operations such as massaging, cleaning, relaxing underlying muscles, for minimizing wrinkles, etc. See e.g., FIG. 47.

In some embodiments, controller 4701 may be programmed (e.g., by firm-ware/software non-transitorily stored in memory 4703) to operate in pre-defined modes of operations such as, but not limited to: a cleaning mode, a massage mode, a skin product application mode, a temperature mode, a cooling mode, a heating mode, a wrinkle minimization mode, a relaxing/soothing mode, combinations thereof, and/or the like. For each category of mode of operation there may be more than one mode of operation. For example, and without limiting the scope of the present invention, regarding the cleaning mode category, there may be more than one cleaning mode. In such an implementation, each mode may produce different output characteristics, such as, but not limited to, a particular range of motor 4707 vibratory frequency, wave pattern, intensity, duration, timed rhythmic pulsations, and/or pre-defined time interval(s). Different selected timed pulsations may be adjusted and/or coordinated to include various predetermined and possibly different and shifting temperature profiles from heater-cooler 4709. In some embodiments, the user may select a given mode through interaction with input/output (I/O) means 4715 (such as, but not limited to, by using control(s) 120/125/130). In some embodiments, the user may select a given mode through an interaction with a separate computing-device 4803 (e.g., a smartphone, tablet computer, laptop, or the like) that may be in wireless communication with the given skincare device 100/800/1500/2200/2900/3600 via communication module 4713. See e.g., FIG. 47 and FIG. 48.

For example, and without limiting the scope of the present invention, in a selected cleansing mode, the pulsating waves may be high-frequency configured as "reflective" waves to facilitate pushing cleansing soaps, surfactants, fluids, liquids, gels, and/or the like into (and out) of skin pores.

For example, and without limiting the scope of the present invention, in a selected massaging mode, the pulsating waves may be low-frequency configured to produce an elastic wave pattern.

For example, and without limiting the scope of the present invention, in a selected skin product application mode, the pulsating waves may be configured to produce a unidirectional hammering wave pattern to help push the product into skin pores. Recall, such skin products may be one or more of: ointments, lotions, creams, serums, gels, medicines, pharmaceuticals, medicaments, soaps, surfactants, vitamins, supplements, herbs, plants, vegetables, meats, cleansers, cleaners, de-oilers, de-greasers, masks, makeup, treatments, combinations thereof, and/or like.

In some embodiments, a given skincare device 100/800/1500/2200/2900/3600 may be communicatively coupled with a separate computing-device 4803 (e.g., a smartphone, tablet computer, laptop, or the like). In some embodiments, a nature of such communication between the given skincare device 100/800/1500/2200/2900/3600 and the separate computing-device 4803 may be via a wired connection removably attached to connector 301. In some embodiments, a nature of such communication between the given skincare device 100/800/1500/2200/2900/3600 and the separate computing-device 4803 may be via wireless communication. Communications between the given skincare device 100/800/1500/2200/2900/3600 and the separate computing-device 4803 may be facilitated by communication module 4713. In some embodiments, communication module 4713 may be located at least partially within a given main-body 203/903/3703 and operatively linked to controller 4701. In some embodiments, communication module 4713 may comprise at least one antenna configured for wireless communications. In some embodiments, communication module 4713 may comprise at least one radio configured for wireless communications. In some embodiments, communication module 4713 may facilitate an established (e.g., industry recognized) wireless communication protocol. In some embodiments, communication module 4713 may facilitate wireless communication such as, but not limited to, Bluetooth, Zigbee, combinations thereof, and/or the like. In some embodiments, communication module 4713 may comprise network communication hardware. In some embodiments, communication module 4713 may be configured to operate as a network: switch, gateway, hub, router, modem, combinations thereof, and/or the like. See e.g., FIG. 47 and FIG. 48.

In some embodiments, a user of a given skincare device 100/800/1500/2200/2900/3600 may download software (e.g., a dedicated and/or proprietary mobile app) onto their separate computing-device 4803 (e.g., a smartphone, tablet computer, laptop, or the like) for the purposes of establishing communications between the given skincare device 100/800/1500/2200/2900/3600 and the separate computing-device 4803. Through such software that may be at least in part running on the separate computing-device 4803, the user may communicate (e.g., wirelessly) with the given skincare device 100/800/1500/2200/2900/3600. In some embodiments, through the separate computing-device 4803 and the downloaded software, the user may control operations and/or functions (such as, but not limited to, selecting from pre-defined modes of operation) of the given skincare device 100/800/1500/2200/2900/3600 that may be in communication with their separate computing-device 4803. In some embodiments, indicator 135 (e.g., as a light guide ring) may light up in specific and/or predetermined patterns and/or colors to indicate currently selected mode operation, progress, status, combinations thereof, and/or the like. Indicator 135 as an output may be a component of input/output (I/O) means 4715. See e.g., FIG. 47 and FIG. 48.

As previously noted in the discussion of skincare device 1500, smooth-plate 1501 may be heated and/or cooled. Heating and/or cooling of smooth-plate 1501 may be provided by at least one heater/cooler 4709 that may be operatively linked with smooth-plate 1501. In some embodiments, skincare device 1500 may comprise at least one heater/cooler 4709. In some embodiments, skincare device 1500 may comprise at least two heater/cooler 4709, at least one for heating and at least one for cooling. In some embodiments, heater/cooler 4709 may be located within main-body 203/903/3703. In some embodiments, heater/cooler 4709 may be located within base 105/805. In some embodiments, a single heater/cooler 4709 may provide heating or cooling functions. In some embodiments, heater/cooler 4709 may be a sol-id-state electronic hardware component. In some embodiments, heater/cooler 4709 may be what is known in the electronics industry as a Peltier thermal device/circuit. Direction of current through such a Peltier thermal device/circuit may dictate whether the Peltier thermal device/circuit is cooling or heating. In some embodiments, heater/cooler 4709 may be operatively linked with and controlled by controller 4701. In some embodiments, heater/cooler 4709 may be powered by power-source 4705. See e.g., FIG. 47.

Continuing discussing FIG. 47, in some embodiments, a given skincare device 100/800/1500/2200/2900/3600 may comprise at least one sensor 4711. In some embodiments, sensor 4711 may be an input selected from input/output (I/O) means 4715. In some embodiments, first-electrode 1001 and/or second-electrode 1003 may be a sensor 4711. In some embodiments, sensor 4711 may be operatively linked and controlled by controller 4701. In some embodiments, at least some portion of a given sensor 4711 may be located on an exterior surface of the given skincare device 100/800/1500/2200/2900/3600. In some embodiments, sensor 4711 may be a sensor for measuring a characteristic of human skin, such as, but not limited to: temperature, moisture, resistance, conductivity, combinations thereof, and/or the like. In some embodiments, sensor 4711 and/or input/output (I/O) means 4715 may comprise means for tracking and mapping in three dimensions surface topography of a given region of human skin. In some embodiments, sensor 4711 and/or input/output (I/O) means 4715 may comprise one or more of a GPS module, an accelerometer, a gyroscope, combinations thereof, and/or the like. In some embodiments, inputs (data) received from sensor 4711 may be non-transitorily store in memory 4703. In some embodiments, inputs (data) received from sensor 4711 may be communicated via communication module 4713 to separate computing-device 4803 (e.g., a smartphone, tablet computer, laptop, or the like). Such sensed data may be further used for controlling various operations of the given skincare device 100/800/1500/2200/2900/3600. In some embodiments, software downloaded to separate computing-device 4803 may process, manipulate, analyze, and/or display sensed data to the user of their separate computing-device 4803. Such sensed data over time may be used to model, predict, and/or trend aspects of skin health. For example, one or more sensors 4711, data from such sensor(s) 4711, and user data (such as, but not limited to, age, gender, height, weight, medical history, diagnosis, etc.) and the software downloaded to the separate computing-device 4803 may in combination be used for providing skin health information, such as, but not limited to, skin moisture levels, skin's visible age, face mask product absorption state, effectiveness of treatment, amount of makeup applied, percentage of makeup removed after cleaning, combinations thereof, and/or the like.

In some embodiments, the plurality of electronic components of a given skincare device may comprise at least one motion measuring means that may be operatively linked and powered by the at least one power-source 4705. In some embodiments, when the given skincare device may be used by its outer exterior portion being physically pressed against a region of human skin, the at least one motion measuring means may map a topographical contour of that region of human skin. In some embodiments, the at least one motion measuring means may be selected from one or more of: an accelerometer, a gyroscope, a GPS module, combinations thereof, and/or the like.

Continuing discussing FIG. 47, in some embodiments, a given skincare device 100/800/1500/2200/2900/3600 may comprise input/output (I/O) means 4715. In some embodiments, input/output (I/O) means 4715 may be operatively linked to and controlled by controller 4701. In some embodiments, input/output (I/O) means 4715 may be powered by power-source 4705. In some embodiments, input/output (I/O) means 4715 may comprise one or more of: touch-point 110, touch-point 115, control 120, control 125, control 130, indicator 135, first-electrode 1001, second-electrode 1003, smooth-plate 1501, motors 4707, heater/cooler 4709, sensors 4711, controls, buttons, switches, slides, dials, power button, levers, pulls, toggles, interfaces, screen/display, touchscreen, lights, LEDs (light emitting diodes), light rings, speakers, microphones, cameras, GPS modules, accelerometers, gyroscopes, electrodes, sensors, radios, antennas, combinations thereof, and/or the like.

In some embodiments, the plurality of electronic components of a given skincare device may comprise first-electrode 1001 and a second-electrode 1003, wherein the at least one power-source 4705 may be operatively linked to both the first-electrode 1001 and the second-electrode 1003, wherein at least a portion of the first-electrode 1001 and at least a portion of the second-electrode 1003 may be located on an exterior surface of the given skincare device.

In some embodiments, first-electrode 1001 and second-electrode 1003 may be configured to emit an electrical pulse for stimulating the region of human skin. In some embodiments, first-electrode 1001 and second-electrode 1003 may be configured to emit a micro-electrical current pulse for stimulating the region of human skin. In some embodiments, first-electrode 1001 and second-electrode 1003 may be configured to operate as "e-stem" components. The characteristics of the delivered electrical pulses may be predetermined and adjustable within a predetermined range. In such embodiments, first-electrode 1001 and second-electrode 1003 may be types of input/output (I/O) means 4715.

In some embodiments, first-electrode 1001 and second-electrode 1003 may be configured to act as sensors for sensing at least one characteristic of the region of human skin. In some embodiments, the at least one characteristic of the region of human skin may comprise at least one of: skin temperature, skin moisture, skin resistance, skin conductivity, combinations thereof, and/or the like. In some embodiments, data from measuring/sensing the at least one characteristic of the region of human skin may be used to determine: how clean or how dirty that region of human skin may be; if makeup removal is complete; skin health; skin age; combinations thereof, and/or the like. In such embodiments, first-electrode 1001 and second-electrode 1003 may be types of sensors 4711.

In some embodiments, the plurality of electronic components of a given skincare device may additionally comprise one or more of: at least one processor 4701, at least one memory 4703, at least one heater/cooler 4709, at least one sensor 4711, at least one communication module 4713, at least one input/output means 4715, other circuitry 4717, combination thereof, and/or the like (that may be in addition to at least one power-source 4705 and at least one motor 4707). In some embodiments, at least one power-source 4705 may be operatively linked to the plurality of electronic components for electrically powering the plurality of electronic components. In some embodiments, at least one processor 4701 may be operatively linked to: at least one memory 4703, at least one power-source 4705, at least one motor 4707, heater/cooler 4709, at least one sensor 4711, at least one communication module 4713, at least one input/output means 4715, other circuitry 4717, combinations thereof, and/or the like. In some embodiments, other circuitry 4717 may form the operative linkages between the electronic components selected from the plurality of electronic components. In some embodiments, instructions non-transitorily stored in at least one memory 4703 may govern how at least one processor 4701 controls and/or operates one or more of the following: at least one memory 4703, at least one power-source 4705, at least one motor 4707, heater/cooler 4709, at least one sensor 4711, at least one communication module 4713, at least one input/output means 4715, other circuitry 4717, combinations thereof, and/or the like. In some embodiments, at least one communication module 4713 may comprise means for electronic communications with other computing devices, such as, but not limited to, computing-device 4803.

In some embodiments, other circuitry 4717 may comprise electrical and/or electronic components for facilitating operations of the various elements of the given skincare device 100/800/1500/2200/2900/3600, such as, but not limited, for facilitating operations of: controller 4701, memory 4703, power-source 4705, motor(s) 4707, heater/cooler 4709, sensor 4711, communication module 4713, input/output (I/O) means 4715, combinations thereof, and/or the like. In some embodiments, other circuitry 4717 may comprise wires, wiring, fiber optics, electrical connections, circuit boards, printed circuit boards (PCB), integrated circuits, micro-chips, semiconductors, processors, cables, cabling, bus, switches, transistors, resistors, capacitors, inductors, receivers, transducers, LEDs (light emitting diodes), transformers, converters, combinations thereof, and/or the like.

In some embodiments, other circuitry 4717 may comprise a surface electronic circuit for producing microcurrent. In some embodiments, such circuitry may be configured for sending weak electrical signals into the skin for skin tightening, muscle stimulation, cell stimulation, and to trigger the body's natural skin enhancement chemicals at a cellular level. In some embodiments, such circuitry may be operatively linked to first-electrode 1001 and/or to second-electrode 1003.

Figure 48:
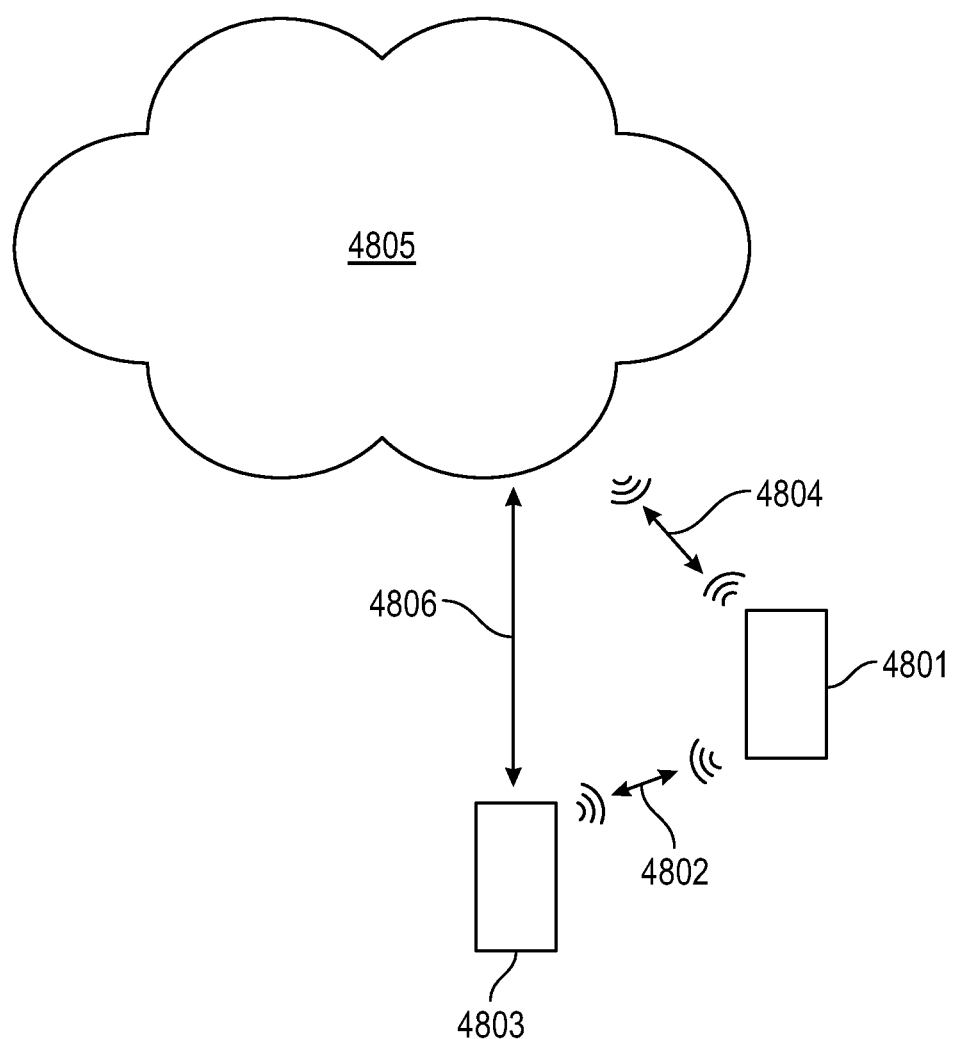
FIG. 48 shows possible communication pathways that a given skincare device may engage in, as a schematic block diagram.

FIG. 48 may show a schematic block diagram for possible communications of a given skincare device 4801 and other devices that may be separate and distinct from the given skincare device 4801. In some embodiments, skincare device 4801 may any of the previously discussed skincare devices (such as, 100/800/1500/2200/2900/3600).

Continuing discussing FIG. 48, computing-device 4803 may a computer that may be separate and distinct from skincare device 4801. For example, computing-device 4803 may be selected from a smartphone, a smart watch, a tablet computer, a laptop, a desktop, a tower computer, a server, a microcomputer, a workstation, a mainframe, combinations thereof, and/or the like. A given computing-device 4803 may be associated with a user/consumer, and in such scenarios, computing-device 4803 may most often be selected from a smartphone, a tablet computer, or a laptop. A given computing-device 4803 may be associated with a technician, and in such scenarios, computing-device 4803 may most often be selected from a smartphone, a tablet computer, or a laptop. A given computing-device 4803 may be associated with a back-end operations, such as, but not limited to customer service, and in such scenarios, computing-device 4803 may most often be selected from a laptop, a desktop, a tower computer, a server, a microcomputer, or a workstation.

Continuing discussing FIG. 48, reference numeral "4805" may refer generically to the Internet, a WAN (wide area network), a LAN (local area network), a computer network, combinations thereof, and/or the like. Internet/WAN/LAN/network 4805 may further comprise electronics and hardware to facilitate the given WAN (wide area network), LAN (local area network), and/or computer network, such as various computers, switching and/or routing equipment, hubs, switches, gateways, routers, modems, cabling, combinations thereof, and/or the like.

Continuing discussing FIG. 48, reference numerals "4802," "4804," and "4806" refer to specific communication pathways, that may be via wired communications, wireless communications, combinations thereof, and/or the like. Communication pathway 4802 may be between skincare device 4801 and computing-device 4803. Communication pathway 4804 may be between skincare device 4801 and Internet/WAN/LAN/network 4805. Communication pathway 4806 may be between computing-device 4803 and Internet/WAN/LAN/network 4805. In some embodiments, communication pathways 4802 and/or 4804 may be facilitated by communication module 4713 of skincare device 4801.

Continuing discussing FIG. 48, in some embodiments, skincare device 4801 may be in direct communication with computing-device 4803 via communication-pathway 4802. In some embodiments, communication pathway 4802 may be via wired communications, wireless communications, combinations thereof, and/or the like.

Continuing discussing FIG. 48, in some embodiments, skincare device 4801 may be in indirect communication with computing-device 4803 via communication-pathway 4804 to Internet/WAN/LAN/network 4805, and via communication pathway 4806 between Inter-net/WAN/LAN/network 4805 and computing-device 4803. That is, communications between skincare device 4801 and computing-device 4803 may be routed through Inter-net/WAN/LAN/network 4805 in some embodiments (e.g., when skincare device 4801 and computing-device 4803 may not be local to each other).

Figure 49:
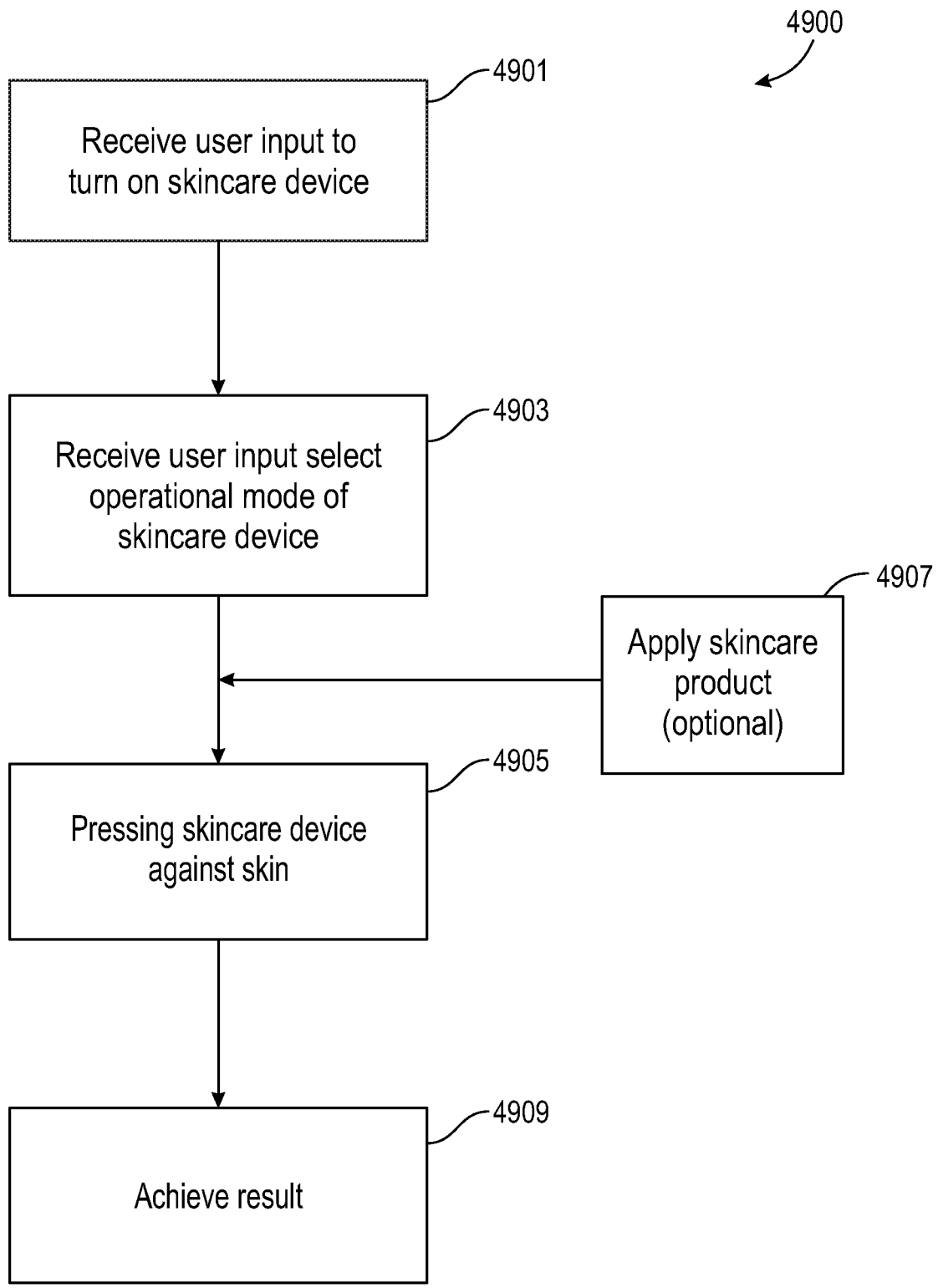
FIG. 49 may show a flow diagram of at least some steps in a method for physically engaging at least one region of human skin using at least an exterior portion of a given skincare device.

FIG. 49 may show a flow diagram of at least some steps in a method 4900. In some embodiments, method 4900 may be a method for physically engaging at least one region of human skin using at least an exterior portion of a given skincare device (e.g., 100/800/1500/2200/2900/3600/4801) to achieve a result with respect to the at least one region of human skin that was physically engaged. In some embodiments, method 4900 may comprise steps 4901, 4903, 4905, and 4909. In some embodiments, method 4900 may comprise steps 4901, 4903, 4907, 4905, and 4909. In some embodiments, step 4907 may be optional.

Continuing discussing FIG. 49, in some embodiments, step 4901 may be a step of receiving a user input at the skincare device for turning on the skincare device. In some embodiments, successful completion of step 4901 may result in the given skincare device being turn on and/or being powered up and ready for use. In some embodiments, in step 4901 the received user input for turning on the given skincare device may be received at control 120/125/130 located on an exterior region of the given skincare device. In some embodiments, in step 4901 the received user input for turning on the skincare device may be received from computing-device 4803 that may be in communication with the given skincare device. In some embodiments, the communication between the computing-device 4803 and the given skincare device may be wireless communication (see e.g., FIG. 48). In some embodiments, step 4901 may progress into step 4903.

Continuing discussing FIG. 49, in some embodiments, step 4903 may be a step of receiving a user input at the given skincare device of selecting an operational mode for that given skincare device and then activating that operational mode for that given skincare device. In some embodiments, the operational modes of step 4903 may be selected from one or more of: cleaning, makeup removal, massaging, relaxation, soothing, skincare product application, skincare product removal, pulsating at a predetermined waveform, heating, cooling, sensing a characteristic of skin, mapping topographical contour of the at least one region of human skin, wrinkle reduction, lymphatic massage, lymphatic drainage, combinations thereof, and/or the like. In some embodiments, the selected operational mode of the given skincare device may run for a predetermined interval of time. In some embodiments, in step 4903 the received user input for selecting the operational mode of the given skincare device may be received at control 120/125/130 located on an exterior region of the given skincare device. In some embodiments, in step 4903 the received user input for selecting the operational mode of the given skincare device may be received from computing-device 4803 that may be in communication with the given skincare device. In some embodiments, the communication between the computing-device 4803 and the given skincare device may be wireless communication (see e.g., FIG. 48). In some embodiments, step 4903 may progress into step 4905.

Continuing discussing FIG. 49, in some embodiments, step 4905 may be a step of pressing the at least exterior portion of the given skincare device against the at least one region of human skin while that given skincare device may be operating in the selected operational mode. In some embodiments, step 4905 may progress into step 4909.

Continuing discussing FIG. 49, in some embodiments, in between steps 4903 and 4905, method 4900 may comprise step 4907 of applying at least one skincare product to the at least one region of human skin. In such embodiments, step 4905 may also be modified, such that the pressing also includes pressing the at least one skincare product against the at least one region of human skin using the at least exterior portion of the given skincare device. In some embodiments, the at least one skincare product may be selected from one or more of: ointments, lotions, creams, serums, gels, medicines, pharmaceuticals, medicaments, soaps, surfactants, vitamins, supplements, herbs, plants, vegetables, meats, cleansers, cleaners, de-oilers, de-greasers, masks, makeup, cosmetics, face paint, skin paint, body paint, combinations thereof, and/or the like. In some embodiments, step 4907 may progress into step 4905.

Continuing discussing FIG. 49, in some embodiments, step 4909 may be a step of achieving the result at the region of human skin that was engaged by the given skincare device. In some embodiments, the result of method 3900 may be selected from one or more of: cleaned skin, cleaned skin pores, massaged skin, soothed skin, relaxed skin, loosening of sinus pressure, application of at least one skincare product to the at least one region of skin, removal of skincare products from the at least one region of skin, opening of skin pores, closing of skin pores, heated skin, cooled skin, wrinkle reduction, massaged lymphatic tissue, drained lymphatic tissue, combinations thereof, and/or the like.

Note each such skincare device disclosed herein (e.g., 100/800/1500/2200/2900/3600/4801) may comprise at least a main-body portion (e.g., 203/903/3703). In some embodiments, main-body 203 may be of skincare device 100. In some embodiments, main-body 903 may be of skincare device 800, 1500, 2200, and/or 2900. In some embodiments, main-body 3703 may be of skincare device 3600. Each such main-body portion may comprise at least two opposing major-sides (e.g., first-major-side 103/803/3603 and second-major-side 153/853/3653) and at least one pad (e.g., first-pad 107/807/3607 and/or second-pad 157/857/3657) with a plurality of touch-points (e.g., touch-point 110/115) extending from that at least one pad. In some embodiments, first-major-side 103 and second-major-side 153 may be of skincare device 100. In some embodiments, first-major-side 803 and second-major-side 853 may be of skincare device 800 and/or 2200. In some embodiments, first-major-side 803 may also be of skincare device 1500 and/or 2900. In some embodiments, first-major-side 3603 and second-major-side 3653 may be of skincare device 3600. In some embodiments, first-pad 107 and second-pad 157 may be of skincare device 100. In some embodiments, first-pad 807 and second-pad 857 may be of skincare device 800 and/or 2200. In some embodiments, first-pad 807 may also be of skincare device 1500 and/or 2900. In some embodiments, first-pad 3607 and second-pad 3657 may be of skincare device 3600. Each such main-body portion may further comprise at least one connector 301. Each such main-body portion may further comprise at least one control (e.g., 120/125/130).

In some embodiments, a given skincare device (e.g., 100/800/1500/2200/2900/3600/4801) may comprise at least a main-body (e.g., 203/903/3703) that may be a closed three-dimensional shape, enclosing a volume, wherein the main-body may comprises two opposing major-sides, a first-major-side (e.g., 103/803/3603) and a second-major-side (e.g., 153/853/3653), respectively. In some embodiments, the first-major-side may be joined to the secondmajor-side along a shared boundary (e.g., 140/840/3640) that runs along an outer peripheral edge of the given main-body such that the volume may be substantially enclosed by the first-major-side joined to the second-major-side. In some embodiments, disposed at least partially between the first-major-side and the second-major-side and at least partially inside the volume of the main-body may be a plurality of electronic components, such as shown in FIG. 47. In some embodiments, the first-major-side may comprise a given first-pad (e.g., 107/807/3607) on an upper portion of that given first-major-side and the second-major-side may comprise a given second-pad (e.g., 157/807/1501/3657) on an upper portion of that given second-major-side. In some embodiments, the first-pad and the second-pad may each have their own respective outer exterior portion that may be configured for physically pressing against a region of human skin. In some embodiments, the plurality of electronic components may comprise at least one motor (e.g., 4707) and at least one power-source (e.g., 4705). In some embodiments, the at least one power-source may be operatively linked to the at least one motor so as to provide electrical power to the at least one motor. In some embodiments, the at least one motor may be operatively linked to at least the first-pad, such that when the at least one motor is activated vibrations are transmitted to the first-pad.

In some embodiments, the at least one motor 4707 of the given main-body 203/903/3703 may be deemed at least one first motor 4707; wherein the base 105/805 may comprise at least one second motor 4707; wherein the at least one second motor 4707 may be housed within the base 105/805; wherein the at least one second motor 4707 may be operatively linked to the at least one power-source 4705. In some embodiments, the at least one second motor 4707 may be operatively linked to the exterior region of the base 105/805 such that when the at least one second motor 4707 may be activated, vibrations are transmitted to the exterior region of the base 105/805 from the at least one second motor 4707, such these vibrations may be transmitted to the region of human skin.

In some embodiments, base 105/805 may comprise at least one heater/cooler circuit 4709 that may be operatively linked to the at least one power-source 4705. In some embodiments, the at least one heater/cooler circuit 4709 of base 105/805 may be operatively linked to the exterior region of the base 105/805, such that when the at least one heater/cooler circuit 4709 of base 105/805 may be activated, heating and/or cooling may be provided to at least a portion of the exterior region of the base 105/805; wherein this heating and/or cooling may then be transmitted to the region of human skin.

In some embodiments, base 105/805 may comprise first-electrode 1001 and second-electrode 1003. In some embodiments, the at least one power-source 4705 may be operatively linked to both first-electrode 1001 and second-electrode 1003. In some embodiments, at least a portion of first-electrode 1001 and at least a portion of second-electrode 1003 may be located on the exterior region of base 105/805.

In some embodiments, the at least one power-source 4705 of the given main-body 203/903/3703 may be deemed at least one first power-source 4705; wherein the base 105/805 may comprise at least one second power-source 4705. In some embodiments, either the at least one first power-source 4705 and/or the at least one second power-source 4705 may be one or more of: batteries, rechargeable batteries, capacitors, lithium based batteries, graphene based batteries, dry cell batteries, combinations thereof, and/or the like.

In some embodiments, at least an exterior region of base 105/805 may be substantially constructed from at least one of: a metal, a precious metal, a stone, a natural stone, a precious stone, glass, a gemstone, a gem, a crystal, a salt crystal, a mineral, a ceramic, a wood, laminates thereof, veneers thereof, combinations thereof, and/or the like.

The figures and the foregoing description give examples of embodiments of skincare devices. Those skilled in the art will appreciate that one or more of the described elements may well be combined into a single functional element. Alternatively, certain elements may be split into multiple functional elements. Elements from one embodiment may be added to another embodiment. For example, orders of processes described herein may be changed and are not limited to the manner described herein. Moreover, the actions of any flow diagram need not be implemented in the order shown; nor do all of the acts necessarily need to be performed. Also, those acts that are not dependent on other acts may be performed in parallel with the other acts. The scope of embodiments is by no means limited by these specific exam-pies. Numerous variations, whether explicitly given in the specification or not, such as differences in structure, dimension, and us of material, are possible.

Various embodiment of portable handheld electronic skincare devices have been described. The foregoing description of the various embodiments of the invention has been presented for the purposes of illustration and disclosure. It is not intended to be exhaustive or to limit the invention to the precise form disclosed. Many modifications and variations are possible in light of the above teaching without departing from the spirit of the invention.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

What is claimed is:
1. A skincare device comprising:
a main-body that is a closed three-dimensional shape, enclosing a volume, wherein the main-body comprises two opposing major-sides, a first-major-side and a second-major-side, respectively;
wherein the first-major-side is joined to the second-major-side along a shared boundary that runs along an outer peripheral edge of the main-body such that the volume is enclosed by the first-major-side joined to the second-major-side and by a bottom of the main-body;
wherein disposed at least partially between the first-major-side and the second-major-side and at least partially inside the volume of the main-body are a plurality of electronic components; and
a base that is a separate component from the main-body, wherein the base is configured to be attached to the bottom of the main-body, wherein a bottom surface of the base is curved such that a distance from a top of the main-body to the base is greatest at a middle bottom of the base when the base is attached to the main-body, wherein the base is weighted such that the skincare device stands vertically upright when the skincare device is resting on top of a horizontal surface when the base is attached to the main-body, wherein the bottom surface of the base that is curved is configured for physically pressing against a region of human skin;

wherein the first-major-side comprises a first-pad on an upper portion of the first-major-side and the second-major-side comprises a second-pad on an upper portion of the second-major-side;

wherein the first-pad and the second-pad each have their own respective outer exterior portions that face away from each other and that is configured for physically pressing against the region of human skin;

wherein the plurality of electronic components comprises at least one motor and at least one power-source;

wherein the at least one power-source is operatively linked to the at least one motor so as to provide electrical power to the at least one motor;

wherein the at least one motor is operatively linked to at least the first-pad, such that when the at least one motor is activated vibrations are transmitted to the first-pad; and wherein the base comprises at least one heater/cooler circuit that is operatively linked to the at least one power-source;

wherein the at least one heater/cooler circuit is part of the base;

wherein the at least one heater/cooler circuit is operatively linked to the bottom surface of the base, such that when the at least one heater/cooler circuit is activated, heating or cooling is provided to at least a portion of the bottom surface of the base.

2. The skincare device according to claim 1, wherein the first-pad comprises a plurality of touch-points, wherein each touch-point selected from the plurality of touch-points is a cylindrical elongate member extending outwards from the first-pad that terminates in a terminal end, wherein the plurality of such terminal ends forms at least a portion of the outer exterior portion of the first-pad that is configured to physically press against the region of human skin.

3. The skincare device according to claim 2, wherein each touch-point selected from the plurality of touch-points has a same, fixed, and predetermined diameter and length.

4. The skincare device according to claim 2, wherein the plurality of touch-points are arranged in a pattern so as to have a single consistent texture.

5. The skincare device according to claim 2, wherein the plurality of touch-points of the first-pad are deemed a first plurality of touch-points, wherein the second-pad comprises a second plurality of touch-points, wherein each touch-point selected from the second plurality of touch-points is a cylindrical elongate member extending outwards from the second-pad that terminates in a terminal end, wherein the terminal ends selected from the second plurality of touch-points forms at least a portion of the outer exterior portion of the second-pad that is configured to physically press against the region of human skin.

6. The skincare device according to claim 5, wherein the first plurality of touch-points are all of a same first single type; wherein the second plurality of touch-points are all of a same second single type, such that each pad, selected from the first-pad and the second-pad, only has one type of touch-points that differs from the touch-points of the other pad.

7. The skincare device according to claim 5, wherein the at least one motor is operatively linked to the second-pad, such that when the at least one motor is activated, vibrations are transmitted to the second-pad.

8. The skincare device according to claim 5, wherein the plurality of electronic components further comprises a second motor that is operatively linked to the at least one power-source and to the second-pad, such that when the second motor is activated, vibrations are transmitted to the second-pad.

9. The skincare device according to claim 2, wherein the outer exterior portion of the second-pad is a smooth-plate that is free of touch-points, that is rigid, that is curved, and that is at least partially made of at least one thermally conductive metal;

wherein the at least one heater/cooler circuit includes a first and a second heater/cooler circuits, wherein the first heater/cooler circuit is operatively linked to said base, and wherein said second heater/cooler circuit is operatively linked to the at least one power-source and to the smooth-plate so as to heat or to cool at least a region of the smooth-plate, such that the smooth-plate heats or cools the region of human skin when the smooth plate is pressed against the region of human skin.

10. The skincare device according to claim 9, wherein the at least one heater/cooler circuit is a Peltier thermal circuit.

11. The skincare device according to claim 9, wherein the smooth-plate is triangle with rounded corners with respect to an orthogonal projection of a hack view of the skincare device.

12. The skincare device according to claim 1, wherein the plurality of electronic components further comprises a first-electrode and a second-electrode, wherein the at least one power-source is operatively linked to both the first-electrode and the second-electrode, wherein at least a portion of the first-electrode and at least a portion of the second-electrode are located on an exterior surface of the skincare device, and wherein the first-electrode and the second-electrode are both configured to directly physically contact the region of human skin.

13. The skincare device according to claim 12, wherein the first-electrode or the second-electrode are configured to emit electrical current into the region of human skin for stimulating the region of human skin.

14. The skincare device according to claim 12, wherein the first-electrode and the second-electrode are configured to act as sensors for sensing at least one characteristic of the region of human skin.

15. The skincare device according to claim 14, wherein the at least one characteristic of the region of human skin comprises at least one of: skin temperature, skin moisture, skin resistance, or skin conductivity.

16. The skincare device according to claim 1, wherein the attachment between the base and the main-body is a removable attachment.

17. The skincare device according to claim 1, wherein the at least one motor of the main-body is deemed at least one first motor; wherein the base comprises at least one second motor; wherein the at least one second motor is housed within the base; wherein the at least one second motor is operatively linked to the at least one power-source; wherein the at least one second motor is operatively linked to the bottom surface of the base such that when the at least one second motor is activated, vibrations are transmitted to the bottom surface of the base from the at least one second motor.

18. The skincare device according to claim 1, wherein the base further comprises a first-electrode and a second-electrode, wherein the at least one power-source is operatively linked to both the first-electrode and the second-electrode, wherein at least a portion of the first-electrode and at least a portion of the second-electrode are located on an exterior of the bottom surface of the base.

19. The skincare device according to claim 1, wherein the at least one power-source of the main-body is deemed at least one first power-source; wherein the base further comprises at least one second power-source, wherein the at least one second power-source is housed within the base.

20. The skincare device according to claim 1, wherein the bottom of the main-body comprises a first connector, wherein a top of the base comprises a second connector, wherein when the base is attached to the main-body, the first connector removably attaches to the second connector, wherein the first connector and the second connector are configured to permit electronic communication between the plurality of electronic components of the main-body and electronics of the base.

21. The skincare device according to claim 1, wherein the main-body comprises a band that circumscribes an exterior of the main-body above and is distinct from the base, wherein the band is configured to emit visible light.

* * * * *